(12) United States Patent
Verdier et al.

(10) Patent No.: US 9,121,031 B2
(45) Date of Patent: Sep. 1, 2015

(54) METHODS AND COMPOSITIONS FOR REGULATING PRODUCTION OF PROANTHOCYANIDINS

(75) Inventors: Jerome A. Verdier, Ardnore, OK (US); Jian Zhao, Ardmore, OK (US); Richard A. Dixon, Sulphur, OK (US); Michael K. Udvardi, Ardmore, OK (US)

(73) Assignee: The Samuel Roberts Noble Foundation, Inc., Ardmore, OK (US)

( * ) Notice: Subject to any disclaimer, the term of this patent is extended or adjusted under 35 U.S.C. 154(b) by 560 days.

(21) Appl. No.: 13/444,507

(22) Filed: Apr. 11, 2012

(65) Prior Publication Data

US 2012/0278914 A1     Nov. 1, 2012

Related U.S. Application Data

(60) Provisional application No. 61/474,224, filed on Apr. 11, 2011.

(51) Int. Cl.
*C12N 15/82*     (2006.01)
*C07K 14/415*    (2006.01)

(52) U.S. Cl.
CPC ............ *C12N 15/825* (2013.01); *C07K 14/415* (2013.01)

(58) Field of Classification Search
None
See application file for complete search history.

(56) References Cited

U.S. PATENT DOCUMENTS

| 7,709,701 B2 | 5/2010 | Dixon et al. |
| 2005/0203033 A1 | 9/2005 | Connors et al. |

OTHER PUBLICATIONS

Payne et al. (1999), Development 126:671-682.*
Quattrocchio F. et al. The Plant Journal; 1998, vol. 13, No. 4 pp. 475-488.*
Heppel et al. Plant Mol. Biol. (2013) vol. 82:457-471.*
Aasland et al., "The SANT domain: putative DNA-binding domain in the SWI-SNF and ADA complexes, the transcriptional co-repressor N-CoR and TFIIIB," *Trends Biochem Sci* 21:87-88, 1996.
Baudry et al., "TT2, TT8, and TTGI synergistically specify the expression of *BANYULS* and proanthocyanidin biosynthesis in *Arabidopsis thaliana*," *Plant J* 39:366-380, 2004.
Bateman et al., "The Pfam Protein Families Database," *Nucleic Acids Research* 30:276-280, 2002.
Benedito at al., "A gene expression atlas of the model legume *Medicago truncatula*," *Plant J* 55:504-513, 2008.
Callis et al., "Introns increase gene expression in cultured maize cells," *Genes Dev* 1:1183-1200, 1987.
Cheng et al., "Reverse genetics in *Medicago truncatula* using *Tnt1* insertion mutants," *Methods in Mol Biol* 678:179-190, 2011.
DeBeaujon et al., "Seed Coat Development and Dormancy," *Seed Development, Dormancy and Germination*, eds. K. Bradford and H. Nonogaki, Blackwell, 2007.
Gallie et al., "Visualizing mRNA Expression in Plant Protoplasts: Factors Influencing Efficient mRNA Uptake and Translation," *Plant Cell* 1:301-311, Mar. 1989.
Goffard et al., "GeneBins: a database for classifying gene expression data, with application to plant genome arrays," *BMC Bioinformatics* 8:87, Mar. 12, 2007.
He et al., "The *Medicago truncatula* gene expression atlas web server," *BMC Bioinformatics* 10:441, Dec. 22, 2009.
Jefferson et al., "GUS fusions: β-glucuronidase as a sensitive and versatile gene fusion marker in higher plants," *EMBO J* 6:3901-3907, 1987.
Johnson et al., "Transparent Testa GLABRA2, a Trichome and Seed Coat Development Gene of *Arabidopsis*, Encodes a WRKY Transcription Factor," *Plant Cell* 14:1359-1375, Jun. 2002.
Koupai-Abyazani et al., "Purification and characterization of a proanthocyanidin polymer from seed of alfalfa (*Medicago sativa*)," *J Agric Food Chem* 41:565-569, 1993.
Lepiniec et al., "Genetics and Biochemistry of Seed Flavonoids," *Annual Review Plant Biol* 57:405-30, 2006.
Nesi et al., "The *TT8* Gene Encodes a Basic Helix-Loop-Helix Domain Protein Required for Expression of *DFR* and *BAN* Genes in *Arabidopsis* Siliques," *Plant Cell* 12:1863-1878, Oct. 2000.
Nesi et al., "The *Arabidopsis* TT2 Gene Encodes an RcR3 MYB Domain Protein that Acts as a Key Determinant for Proanthocyanidin Accumulation in Developing Seed," *Plant Cell* 13:2099-2114, Sep. 2001.
Nesi et al., "The Transparent TEXTA16 locus encodes the *Arabidopsis* Bsister MADS domain protein and is required for proper development and pigmentation of the seed coat," *Plant Cell* 14:2463-2479, 2002.
Pang et al., "Early Steps in Proanthocyanidin Biosynthesis in the Model Legume *Medicago truncatula*," *Plant Physiol* 145:601-615, 2007.
Pang et al., "A WD40 repeat protein from *Medicago truncatula* is necessary for tissue-specific anthocyanin and proanthocyanidin biosynthesis but not for trichome development" *Plant Physiol* 151:1114-1129, 2009.
Peel et al, "The LAP1 MYB transcription factor orchestrates anthocyanidin biosynthesis and glycosylation in *Medicago*," *Plant J* 59(1):136-149, 2009.
Quandt et al., "Transgenic Root Nodules of *Vicia hirsuta*: a fast and efficient system for the study of gene expression in indeterminate-type nodules," *Molelcular Plant-Microbe Interactions*, 6:699-706, 1993.

(Continued)

*Primary Examiner* — Russell Kallis
(74) *Attorney, Agent, or Firm* — Dentons US LLP

(57) ABSTRACT

The invention provides methods and compositions for the modulation of proanthocynidin ("PA;" condensed tannin) production in plants. The methods of the invention allow creation of plants having novel phenotypes, such as alterations in levels of PA or in the types of tissues in which PAs are produced. Altered expression of PA in plants may be achieved, for instance without significantly affecting anthocyanin content or overall secondary metabolite profiles. Alternatively, expression of PA in plants may be achieved while also affecting anthocyanin content.

34 Claims, 12 Drawing Sheets

(56) References Cited

OTHER PUBLICATIONS

Appelhagen et al., "Transparent Testa 1 interacts with R2R3-MYB factors and affects early and late steps of flavonoid biosynthesis in the endothelium of *Arabidopsis thaliana* seeds," *The Plant J* 67(3):406-19, 2011.

Sagasser et al., "*A. thaliana* Transparent Testa 1 is involved in seed coat development and defines the WIP subfamily of plant zinc finger proteins," *Genes & Dev* 16:138-149, 2002.

Skadhauge et al., "Leucocyanidin reductase activity and accumulation of Proanthocyanidins in developing legume tissues," *Am J Bot* 84:494-503, 1997.

Stracke et al., "The R2R3-MYB gene family in *Arabidopsis thaliana*," *Curr Opinion Pl Biol* (5):447-456, 2001.

Tadege et al., "Large-scale insertional mutagenesis using the Tnt1 retrotransposon in the model legume *M. truncatula*," *Plant J* 54:335-347, 2008.

Terrier et al., "Ectopic expression of VvMybPA2 promotes proanthocyanidin biosynthesis in grapevine and suggests additional targets in the pathway," *Plant Physiol* 149:1028-1041, 2009.

Vasil et al., "Increased Gene Expression by the First Intron of Maize *Shrunken-1* Locus in Grass Species," *Plant Physiol* 91:1575-1579, 1989.

Verdier et al., "Functional genomics of *M. truncatula* seed development," Presentation at the 10th International Conference on Seed Science, Costa do Sauipe, Brazil, Apr. 11, 2011.

Walker et al., "The Transparent Testa Glabrai Locus, which regulates trichome differentiation and anthocyanin biosynthesis in *Arabidopsis*, encodes a WD40 repeat protein," *Plant Cell* 11:1337-1349, 1999.

Xie et al., "Metabolic engineering of proanthocyanidins through co-expression of anthocyanidin reductase and the PAP1 MYB transcription factor," *Plant J* 45:895-907, 2004.

Zhao et al., "The 'ins' and 'outs' of flavonoid transport," *Trends Plant Sci* 15:72-80, 2010.

GenBank Accession No. EU040206, "*Medicago truncatula* WD40-1 protein mRNA, complete cds,", Nov. 6, 2009.

GenBank Accession No. AJ299452, "*Arabidopsis thaliana* TT2 gene for transparent testa 2 protein, exons 1-3," Nov. 14, 2006.

GenBank Accession No. Q0PJG9, protein sequence, "MYB transcription factor MYB115," Nov. 28, 2006.

Hancock et al., Expression of the R2R3-MYB Transcription Factor TaMYB14 from *Trifolium arvense* Activates Proanthocyanidin Biosynthesis in the Legumes *Trifolium repens* and *Medicago sativa; Plant Physiology*; vol. 159; pp. 1204-1220; 2012.

Liu et al., MYB5 and MYB14 Play Pivotal Roles in Seed Coat Polymer Biosynthesis in *Medicago truncatula; Plant Physiology*; vol. 165; pp. 1-16; 2014.

Pang et al.,"A transcript profiling approach reveals an epicatechin-specific glucosyltransferase expressed in the seed coat of *Medicago truncatula*," *PNAS*; vol. 105, No. 37; pp. 14210-14215; 2008.

Verdier et al, .MtPAR MYB transcription factor acts as an on switch for proanthocyanidin biosynthesis in *Medicago truncatula; PNAS*; Early Edition; pp. 1-6; 2011.

\* cited by examiner

FIG. 6
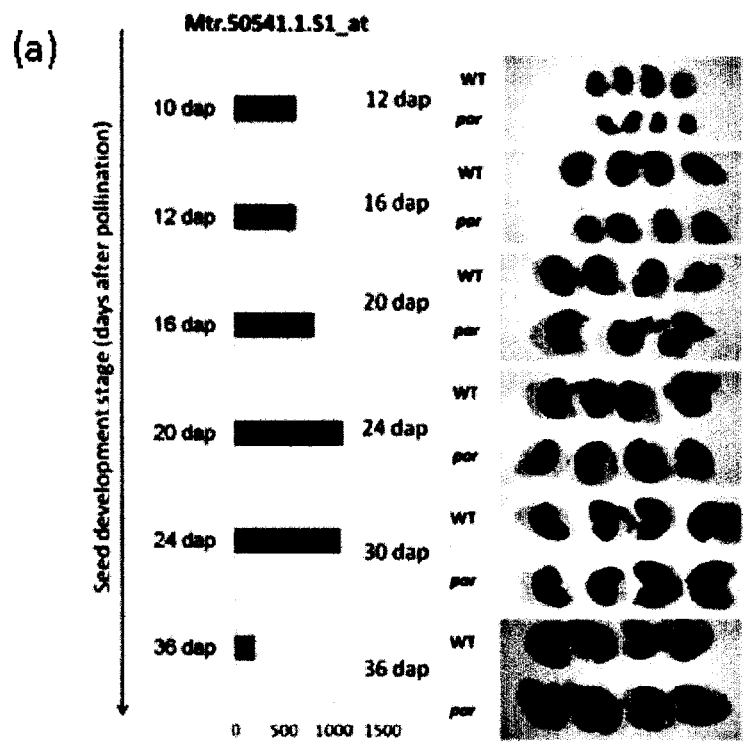
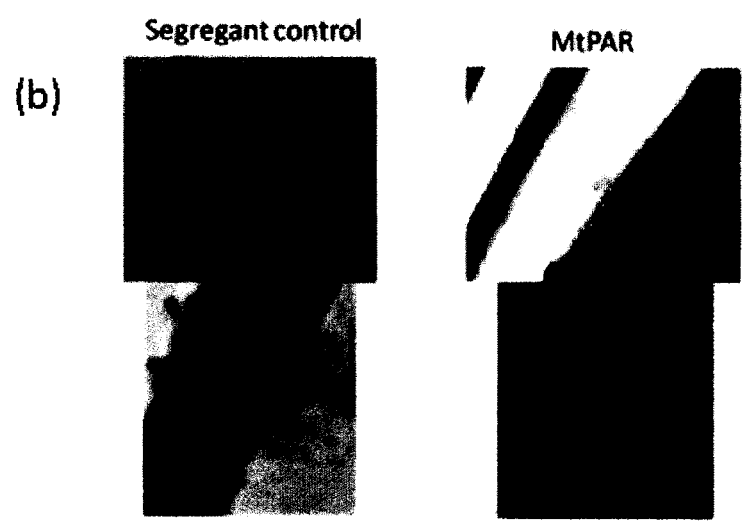

FIG. 9

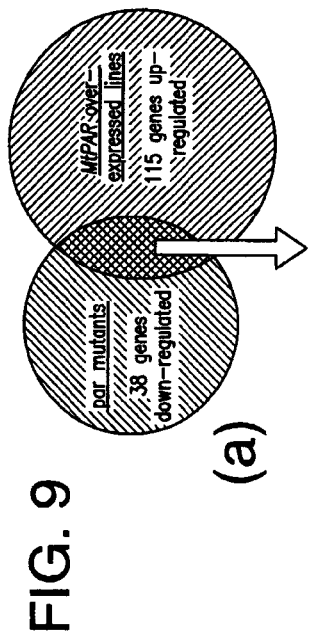

(a)

| Probesets | Target Description | Representative Public ID | Tnt1 mutant lines ||| Hairy root transformants |||
|---|---|---|---|---|---|---|---|---|
| | | | Ratio par/Ck | p-value | q-value | Ratio PAR/GUS | p-value | q-value |
| Mtr.20567.1.S1_at | Type III polyketide sythase; Naringenin-chalcone synthase | 1115.m00010 | 0.006838 | 0.025969 | 0 | 4.701298 | 0.019352 | 0 |
| Mtr.36333.1.S1_at | similar to UP|Q84JJ4 (Q84JJ4) Flavonoid 3'-hydroxylase (Fragment), partial (21%) | BE248436 | 0.027408 | 0.008888 | 0 | 2.295895 | 0.088535 | 9.24E-13 |
| Mtr.6517.1.S1_at | similar to UP|Q84J865 (Q84J65) Gray pubescence flavonoid 3'-hydroxylase, partial (49%) | BQ147749 | 0.049162 | 0.005737 | 0 | 2.637451 | 0.00151 | 0 |
| Mtr.14017.1S1_at | weakly similar to UP|LDOX_ARATH (Q96323) Leucoanthocyanidin dioxygenase (LDOX) Anthocyanidin synthase (ANS), partial (19%) | TC99980 | 0.062597 | 0.030434 | 0 | 3.857393 | 0.000634 | 0 |
| Mtr.39897.1S1_at | simmilar to UP|P93697 (P93697) CPRD12 protein, partial (61%) | TC105988 | 0.079569 | 0.016543 | 1E-231 | 2.06289 | 0.044517 | 3.63E-22 |
| Mtr.14428.1S1_at | Naringenin-chalcone synthase; Type III polyketide synthase | 1115.m00011 | 0.11897 | 0.101612 | 0 | 2.235309 | 0.009315 | 2.14E-70 |
| Mtr.44985.1S1_at | Anthocyanidin reductase, complete | TC98546 | 0.165667 | 0.027887 | 4.22E-28 | 2.333918 | 0.371479 | 2.5E-54 |
| Mtr.50541.1S1_at | MtPAR gene, Myb, DNA-binding; Homeodomain-like | 1054.m00009 | 0.196626 | 0.078708 | 9.26E-16 | 104.6917 | 0.000461 | 0 |
| Mtr.28714.1S1_at | homologue to PRF|1609233A|226868|1609233A chalcone synthase 3, {Sinapis alba;}, partial (12%) | B1311259 | 0.214729 | 0.028186 | 4.16E-73 | 2.332891 | 0.096372 | 5.3E-181 |
| Mtr.109917.1S1_at | similar to UP|C773_SOYBN (Q48929) Cytochrome P450 77A3, partial (95%) | TC108343 | 0.367035 | 0.011932 | 3E-109 | 4.242139 | 0.111589 | 0 |
| Mtr.26465.1.S1_s_at | similar to UP|PEAM_SPIOL (Q9M571) Phosphoethanolamine N-methyltransferase | 1520.m0027 | 0.420515 | 0.000341 | 0 | 2.180135 | 0.106376 | 0.000483 |
| Mtr.37221.1S1_at | homoigue to UP|Q43437 (Q43437) Photosystem II type I chlorophyll a/b-binding protein precursor, complete | TC100154 | 0.476583 | 0.038178 | 5.7E-07 | 3.032651 | 0.370587 | 6.1E-150 |

(b)

METHODS AND COMPOSITIONS FOR REGULATING PRODUCTION OF PROANTHOCYANIDINS

This application claims the priority of U.S. Provisional Appl. Ser. No. 61/474,224, filed Apr. 11, 2011, the entire disclosure of which is incorporated herein by reference.

STATEMENT REGARDING FEDERALLY SPONSORED RESEARCH OR DEVELOPMENT

The disclosed subject matter was developed in part with funding from United States Department of Agriculture grant USDA\CSREES-NRI plant genome project 2006-35300-17143. The government may have certain rights in the invention.

INCORPORATION OF SEQUENCE LISTING

The sequence listing contained in the file named "NBLE080US_ST25.txt", which is 12.1 kilobytes (size as measured in Microsoft Windows®) and was created on Apr. 11, 2012, is filed herewith by electronic submission and is incorporated by reference herein.

BACKGROUND OF THE INVENTION

1. Field of the Invention

The present invention generally relates to plant genetics. More specifically, the invention relates to genes and enzymes involved in the biosynthesis of anthocyanins, proanthocyanidins, and tannins, and methods for use thereof.

2. Description of the Related Art

Proanthocyanidins ("PAs," also called condensed tannins ("CTs")) are oligomers of flavan-3-ol units and are prominent, colored compounds in seed coats, leaves, fruits, flowers and bark of many plant species. PAs and their monomeric building blocks such as catechin and epicatechin are potent antioxidants with beneficial effects on human health, including cardio-protective, anticancer and anti-inflammatory activities. In addition, PAs from various plants have beneficial effects on cardiac health and immune responses. PAs can therefore affect the nutritional quality of human and animal food.

SUMMARY OF THE INVENTION

In one aspect, the invention provides a DNA nucleic acid comprising a DNA sequence selected from the group consisting of: (a) a nucleic acid sequence encoding the polypeptide sequence of SEQ ID NO:1; (b) a nucleic acid sequence comprising the sequence of SEQ ID NO:2; (c) a nucleic acid sequence that hybridizes to SEQ ID NO:2 under conditions of 1×SSC, and 65° C. and encodes a polypeptide which regulates flavonoid synthesis; (d) a nucleic acid sequence encoding a polypeptide with at least 85% amino acid identity to SEQ ID NO:1 and encodes a polypeptide which regulates flavonoid synthesis; (e) a nucleic acid sequence with at least 85% identity to SEQ ID NO:2 and encodes a polypeptide which regulates flavonoid synthesis; and (f) a complement of a sequence of (a)-(e) or a fragment thereof wherein the nucleic acid sequence regulates flavonoid synthesis; wherein the DNA sequence is operably linked to a heterologous promoter. In certain embodiments, the sequence may have at least 90%, at least 95%, at least 98%, or at least 99% sequence identity with SEQ ID NO:1 or SEQ ID NO:2.

The invention further provides a recombinant vector comprising a DNA sequence as provided herein. The recombinant vector may further comprise at least one additional sequence chosen from the group consisting of: a regulatory sequence, a selectable marker, a leader sequence and a terminator. In particular embodiments, the polypeptide that activates anthocyanin or proanthocyanidin biosynthesis is selected from the group consisting of: phenylalanine ammonia-lyase (PAL), cinnamate 4-hydroxylase (C4H), 4-coumarate:CoA ligase (4CL), chalcone synthase (CHS), chalcone isomerase (CHI), flavanone 3-hydroxylase (F3H), dihydroflavonol reductase (DFR), anthocyanidin synthase (ANS), leucoanthocyanidin reductase (LAR), anthocyanidin reductase (ANR), a proanthocyanidin or anthocyanidin glucosyltransferase (GT), LAP1, LAP2, LAP3, LAP4, or AtPAP1 (production of anthocyanin pigment). The recombinant vector may further be defined as comprising a promoter, wherein the promoter is a plant developmentally-regulated, organelle-specific, inducible, tissue-specific, constitutive, or cell-specific promoter. The recombinant vector may, in certain embodiments, be defined as an isolated expression cassette.

Another aspect of the invention comprises an isolated polypeptide having at least 85% amino acid identity to the amino acid sequence of SEQ ID NO:1, or a fragment thereof, which regulates flavonoid synthesis. In certain embodiments, the flavonoid is an anthocyanin or a proanthocyanidin.

Yet another aspect of the invention comprises a transgenic plant transformed with a DNA molecule comprising a DNA sequence selected from the group consisting of: (a) a nucleic acid sequence encoding the polypeptide sequence of SEQ ID NO:1, (b) a nucleic acid sequence comprising SEQ ID NO:2; (c) a nucleic acid sequence that hybridizes to SEQ ID NO:2 under conditions of 1×SSC, and 65° C. and encodes a polypeptide which regulates flavonoid synthesis; (d) a nucleic acid sequence encoding a polypeptide with at least 85% amino acid identity to SEQ ID NO:1 and which regulates flavonoid synthesis; (e) a nucleic acid sequence with at least 85% identity to SEQ ID NO:2 and that encodes a polypeptide which regulates flavonoid synthesis; and (f) a complement of a sequence of (a)-(e), or a fragment thereof, wherein the nucleic acid sequence is operably linked to a heterologous promoter. Seed of such a plant, and progeny of such a plant of any subsequent generation, each comprising the selected DNA, are another aspect of the invention. In certain embodiments the invention provides such a transgenic plant, wherein the plant is a forage crop. In particular embodiments the plant is a legume. In more particular embodiments, the plant is a *Medicago* plant, such as an alfalfa plant. A plant that expresses the DNA molecule and exhibits altered flavonoid (e.g. proanthocyanidin and/or anthocyanin) biosynthesis in selected tissues relative to those tissues in a second plant that differs from the transgenic plant only in that the selected DNA is absent is also provided. In certain embodiments, proanthocyanidin and/or anthocyanin biosynthesis is increased. In other embodiments, proanthocyanidin and/or anthocyanin biosynthesis is decreased.

The transgenic plant may further be defined, in certain embodiments, as one that is transformed with a selected DNA which regulates flavonoid synthesis, selected from the group consisting of SEQ ID NO:1 or a fragment thereof. In other embodiments, the transgenic plant may further be defined as transformed with a selected DNA sequence complementary to a sequence which regulates flavonoid synthesis, e.g. proanthocyanidin and/or anthocyanin biosynthesis. In particular embodiments, the transgenic plant is further defined as transformed with and comprising a DNA sequence complementary to the MtPAR sequence of SEQ ID NOs:2-3, or a fragment thereof, such as a sequence comprising 17 or more, 19 or more, or 21-24 or more contiguous nucleotides complementary to SEQ ID NO:2 or SEQ ID NO:3. In other embodiments, the transgenic plant is further defined as transformed with a DNA sequence encoding the polypeptide of SEQ ID NO:1. The invention also provides such a transgenic plant, wherein the plant is a forage legume. In particular embodiments, the plant is a *Medicago* plant. In particular embodiments, the plant is alfalfa (*Medicago sativa*).

In some embodiments, the transgenic plant is further defined as comprising proanthocyanidins in tissues other than seeds. In certain embodiments the tissues are selected from the group consisting of leaves, stems, and roots. In other embodiments, the tissues are defined as tissues destined for animal consumption.

In other embodiments, the transgenic plant comprises a nucleic acid selected from the group consisting of: (a) a nucleic acid sequence encoding the polypeptide sequence of SEQ ID NO:1; (b) a nucleic acid sequence comprising the sequence of SEQ ID NO:2; (c) a nucleic acid sequence that hybridizes to SEQ ID NO:2 under conditions of 1×SSC, and 65° C. and encodes a polypeptide which regulates flavonoid synthesis; (d) a nucleic acid sequence encoding a polypeptide with at least 85% amino acid identity to SEQ ID NO:1 and encodes a polypeptide which regulates flavonoid synthesis; (e) a nucleic acid sequence with at least 85% identity to SEQ ID NO:2 and encodes a polypeptide which regulates flavonoid synthesis; and (f) a complement of a sequence of (a)-(e), or a fragment thereof wherein the nucleic acid sequence is operably linked to a heterologous promoter, is further defined as comprising at least one additional transgenic coding sequence chosen from the group consisting of: a regulatory sequence, a sequence that encodes a polypeptide that activates anthocyanin or proanthocyanidin biosynthesis, a selectable marker, a leader sequence and a terminator.

In still further embodiments, the polypeptide that activates anthocyanin or proanthocyanidin biosynthesis is selected from the group consisting of: phenylalanine ammonia-lyase (PAL), cinnamate 4-hydroxylase (C4H), 4-coumarate:CoA ligase (4CL), chalcone synthase (CHS), chalcone isomerase (CHI), flavanone 3-hydroxylase (F3H), dihydroflavonol reductase (DFR), anthocyanidin synthase (ANS), leucoanthocyanidin reductase (LAR), anthocyanidin reductase (ANR), a proanthocyanidin or anthocyanidin glucosyltransferase (GT), LAP1, LAP2, LAP3, LAP4, or AtPAP1 (production of anthocyanin pigment). The transgenic plant may further be defined as a fertile $R_0$ transgenic plant, or as a progeny plant of any generation of a fertile $R_0$ transgenic plant, wherein the transgenic plant comprises the selected DNA.

Also provided by the invention is a cell transformed with a DNA molecule as provided herein. In certain embodiments, the cell is a plant cell. In other embodiments, the cell is a bacterial cell.

The invention also provides a method of producing a plant with increased proanthocyanidin biosynthesis, comprising expressing in the plant an isolated nucleic acid sequence selected from the group consisting of: (a) a nucleic acid sequence encoding the polypeptide sequence of SEQ ID NO:1; (b) a DNA sequence comprising SEQ ID NO:2; (c) a nucleic acid sequence that hybridizes to SEQ ID NO:2 under conditions of 1×SSC, and 65° C. and encodes a polypeptide which regulates flavonoid synthesis; (d) a nucleic acid sequence encoding a polypeptide with at least 85% amino acid identity to SEQ ID NO:1, and encodes a polypeptide which regulates flavonoid synthesis; (e) a nucleic acid sequence with at least 85% identity to SEQ ID NO:2 and encodes a polypeptide which regulates flavonoid synthesis; and (f) a complement of a sequence of (a)-(e), or a fragment thereof, wherein the DNA sequence regulates flavonoid synthesis and is operably linked to a heterologous promoter.

In some embodiments of the invention, the plant further comprises a recombinant vector, wherein the polypeptide that activates anthocyanin or proanthocyanidin biosynthesis is selected from the group consisting of: phenylalanine ammonia-lyase (PAL), cinnamate 4-hydroxylase (C4H), 4-coumarate:CoA ligase (4CL), chalcone synthase (CHS), chalcone isomerase (CHI), flavanone 3-hydroxylase (F3H), dihydroflavonol reductase (DFR), anthocyanidin synthase (ANS), leucoanthocyanidin reductase (LAR), anthocyanidin reductase (ANR), a proanthocyanidin or anthocyanidin glucosyltransferase (GT), LAP1, LAP2, LAPS, LAP4, or AtPAP1 (production of anthocyanin pigment). In certain embodiments, the nucleic acid sequence is introduced into the plant by plant breeding. In other embodiments, the nucleic acid sequence is introduced into the plant by genetic transformation of the plant. Further, in other embodiments the recombinant vector comprises a promoter which is a constitutive or tissue specific promoter. In some embodiments, the plant is further defined as a forage crop. In particular embodiments the plant is a forage legume. In even more particular embodiments the plant is alfalfa.

The invention also provides a method further defined as comprising the preparation of a transgenic progeny plant of any generation of a plant provided herein, wherein the progeny plant comprises the selected nucleic acid sequence. A plant or plant part prepared by this method is also provided.

Yet another aspect of the invention is a method of making food or feed for human or animal consumption comprising: (a) obtaining the plant comprising the DNA molecule; (b) growing the plant under plant growth conditions to produce plant tissue from the plant; and (c) preparing food or feed for human or animal consumption from the plant tissue. In certain embodiments, preparing food or feed comprises harvesting the plant tissue. In some embodiments, the plant tissue is leaf or stem tissue. In particular embodiments, the food or feed is hay, silage, starch, protein, meal, flour or grain.

BRIEF DESCRIPTION OF THE DRAWINGS

The following drawings form part of the present specification and are included to further demonstrate certain aspects of the invention. The invention may be better understood by reference to one or more of these drawings in combination with the detailed description of specific embodiments presented herein:

FIG. 6: (a) Development of PA accumulation through seed development between mutant and WT lines using DMACA staining. (b) Cross sections of WT and mutant seeds.

FIG. 9: (a) Venn diagram for genes down-regulated in loss of function par mutants and up-regulated following ectopic expression of MtPAR in hairy roots; (b) Table representing the 11 common genes which are down-regulated in loss of function mutant lines and up-regulated in ectopic expression transformant lines. Affymetrix ID, putative annotation, TC, expression ratio between mutant vs WT or over-expressing lines vs control with their respective p and q-value are indicated. Significant p-value are indicated in grey.

DETAILED DESCRIPTION OF THE INVENTION

The invention provides methods and compositions for the modification of proanthocyanidin (PA) metabolism in plants. In one embodiment, a MYB family transcription factor ("TF") was identified that regulates PA biosynthesis in seeds. Ectopic expression of the gene in transformed hairy-roots surprisingly led to PA biosynthesis and accumulation. The sequence was identified as a MYB transcription factor and designated as *Medicago truncatula* ProAnthocyanidin Regulator (MtPAR). In accordance with the invention MtPAR will find use in, for example, increasing tannin levels for forage improvement in plants including legumes such as *Medicago* spp. The sequence of the predicted MtPAR polypeptide is given in SEQ ID NO:1 and the mRNA gene sequence is given in SEQ ID NO:2. The genomic MtPAR gene sequence is given in SEQ ID NO:3. This seed coat specific gene acts as a positive regulator of PA biosynthesis.

Importantly, transcription profiling and other studies showed that MtPAR regulates expression of a distinct set of genes, including genes involved in flavonoid biosynthesis, relative to other MYB TFs, such as tt2 and ttg1. For instance, the inventors show herein that heterologous expression of MtPAR affects expression of CHS, F3H, ANS, and AHR enzymes, among tested-for activities. The effects of MtPAR over-expression (or under-expression) on proanthocyanidin accumulation as well as on gene expression profiles in *Medicago* could thus not have been predicted based on studies of effects of other known MYB TFs from *Medicago Glycine*, or *Arabidopsis*.

Transcriptional regulation of flavonoid biosynthesis is not yet well understood in legumes. In the non-legume *Arabidopsis*, six loci are known to have regulatory functions in PA biosynthesis, TT1, TT2, TT8, TT16, TTG1 and TTG2 (for review, see Lepiniec et al., 2006). TT1 and TT16 encode a zinc finger and a MADS box protein, respectively, and are essential for seed pigmentation (Nesi et al., 2002; Sagasser et al., 2002). TTG2 encodes a WRKY transcription factor, which acts downstream of TTG1 (Johnson et al., 2002). TT2, TT8 and TTG1 encode a MYB (Nesi et al., 2001), a bHLH (Nesi et al., 2000) and a WD40 protein (Walker et al., 1999), respectively, which interact to form a ternary TF complex. Mutation in any one of these TFs affects both anthocyanin and PA content in seeds via down-regulation of flavonoid biosynthetic genes (for review Debeaujon et al., 2007). In the *Medicago* par mutants, down-regulation of key genes of the flavonoid pathway was observed. However, in contrast to the *Arabidopsis* mutants, mutations in MtPAR affect soluble and insoluble PA content but not anthocyanin content (FIG. 2b, 2e).

Figure 1:
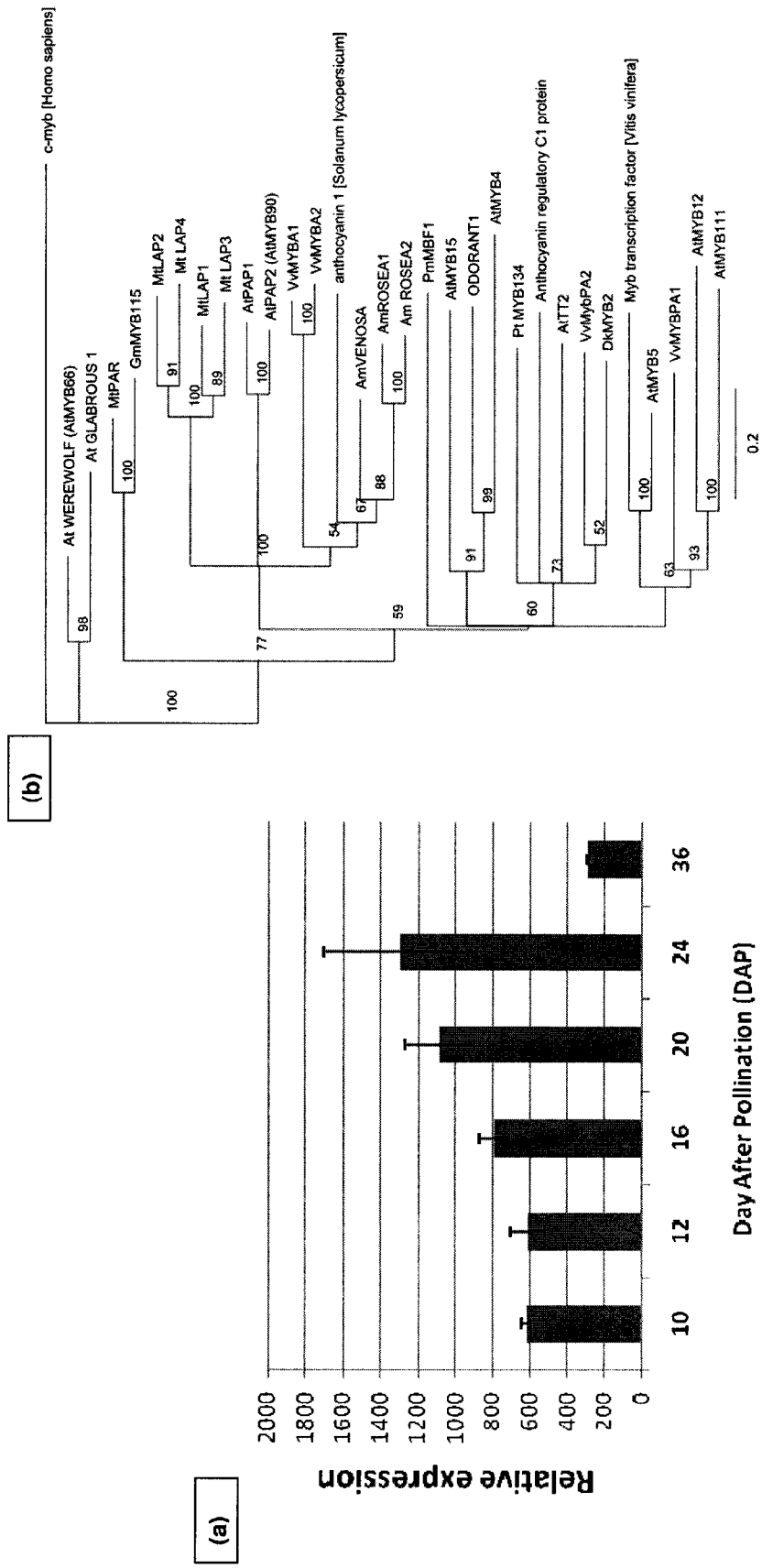
FIG. 1: (a) Expression profile of MtPAR through seed development (10 to 36 DAP) according to the *Medicago* gene expression atlas and in seed tissues (SC, seed coat; E/Eo, embryo and endosperm) according to qRT-PCR data. (b) Phylogenetic analysis of putative flavonoid regulatory proteins containing a R2R3 MYB domain from different species. Alignment was done using ClustalW algorithm and the tree was generated using NJ method. GeneBank accession numbers of amino acid sequences used to prepare this alignment are provided in Table 1.
Figure 2:
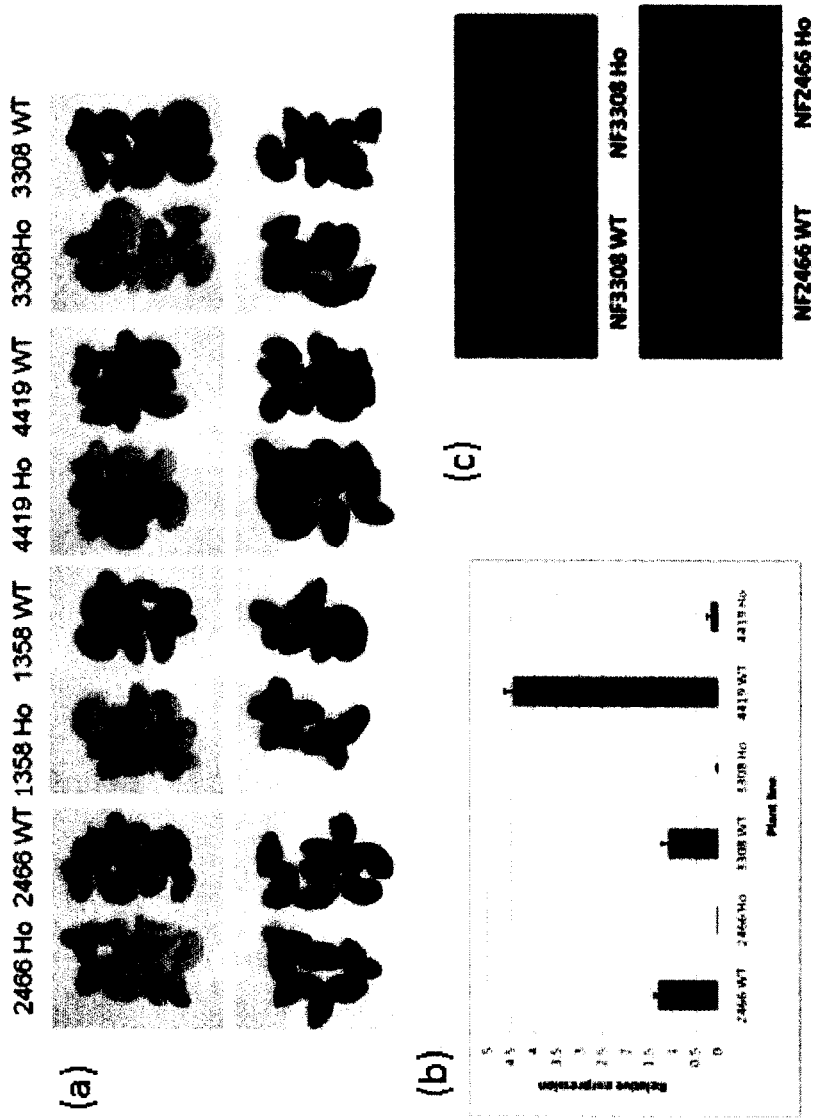
FIG. 2: (a) Effect of mutation on mature seed pigmentation for all mutant lines. DMACA staining of mature seeds from all mutant lines. (b) MtPAR transcript levels between WT and mutant lines. Relative expression is given with respect to MSC27 and PDF2 housekeeping genes. (c) Vanillin staining on mature seeds from two mutant lines and their siblings.
Figure 3:
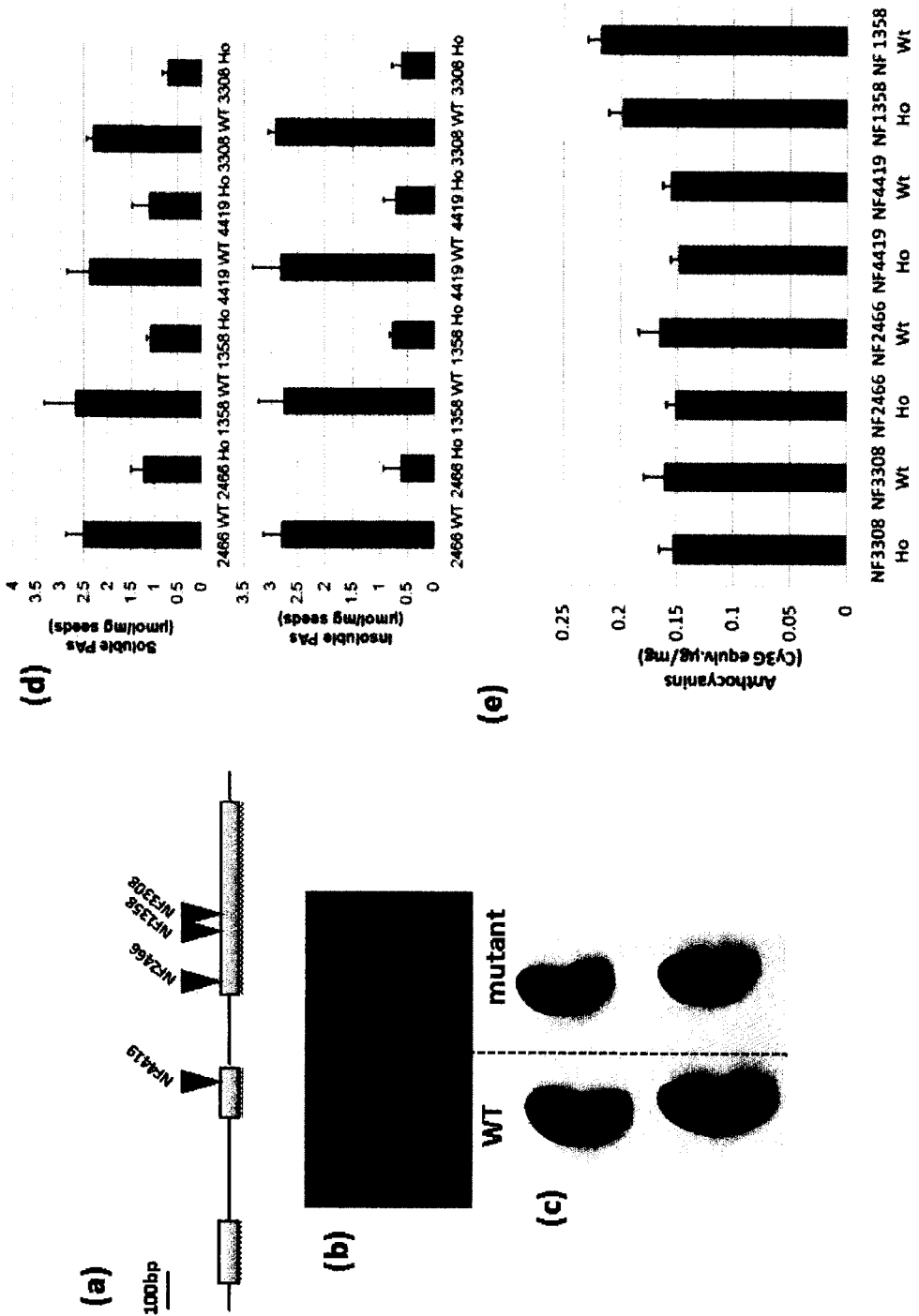
FIG. 3: (a) MtPAR gene model with position of different Tnt1 insertions and the names of the corresponding independent mutant lines. Introns are represented using a line and exons using a rectangular shape; (b) Effect of mutation on mature seed pigmentation for the NF3308 mutant line. A similar phenotype was observed in other mutant lines; (c) DMACA staining of mature seeds from NF3308 mutant line; (d) Levels of extractable PAs (soluble and insoluble); and (e) anthocyanins with respect to their null segregant controls. Values are mean and standard deviations from three biological replicates.
Figure 4:
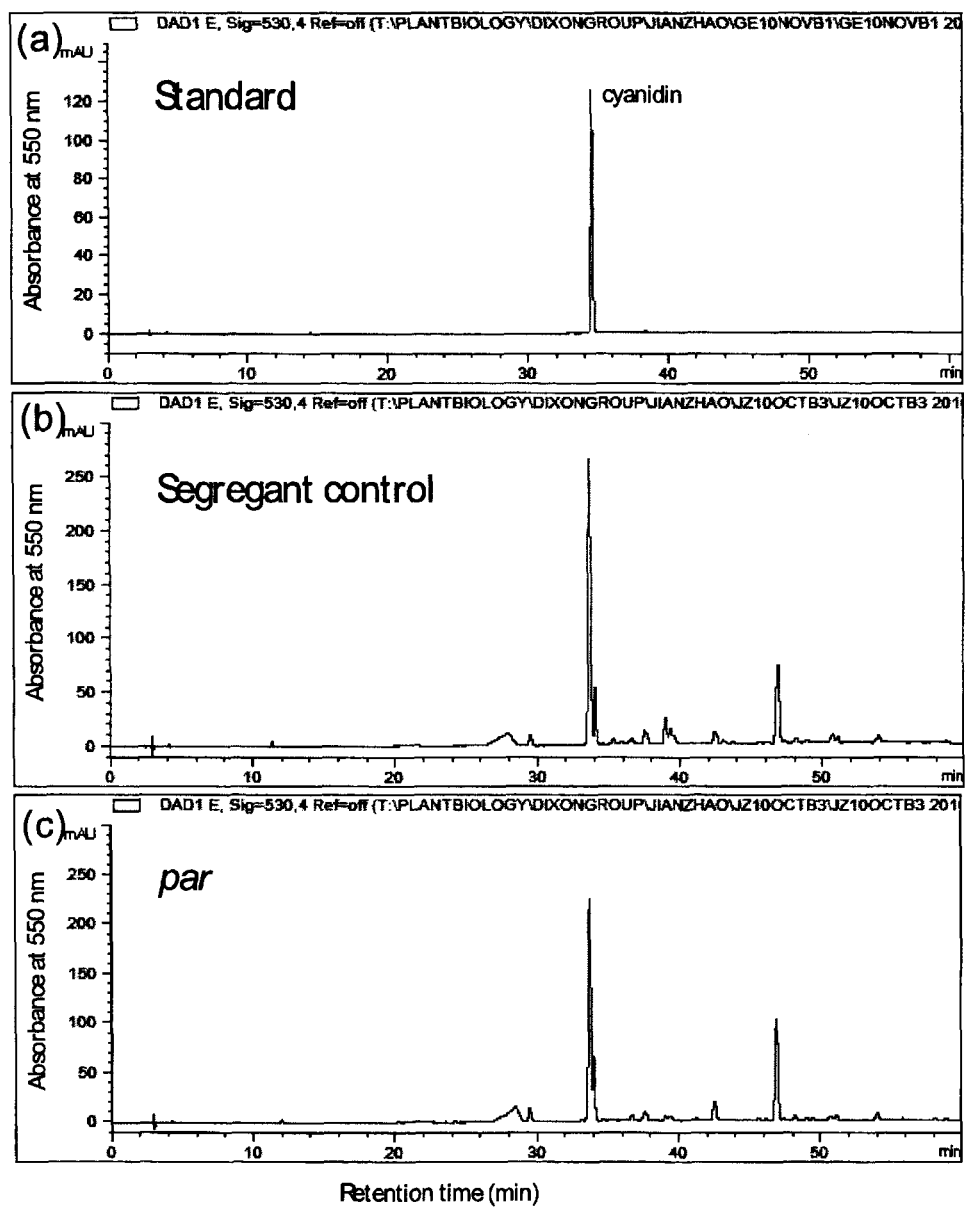
FIG. 4: HPLC chromatograph of anthocyanidins released by hydrolysis of insoluble PAs in butanol-HCl. (a) HPLC chromatogram of hydrolyzate of procyanidin B1 standard. Cyanidin is released. (b) HPLC chromatogram of hydrolyzate of insoluble PA from MtPAR segregant control *M. truncatula* seeds. (c) HPLC chromatogram of hydrolyzate from insoluble PA from MtPAR mutant seeds.
Figure 5:
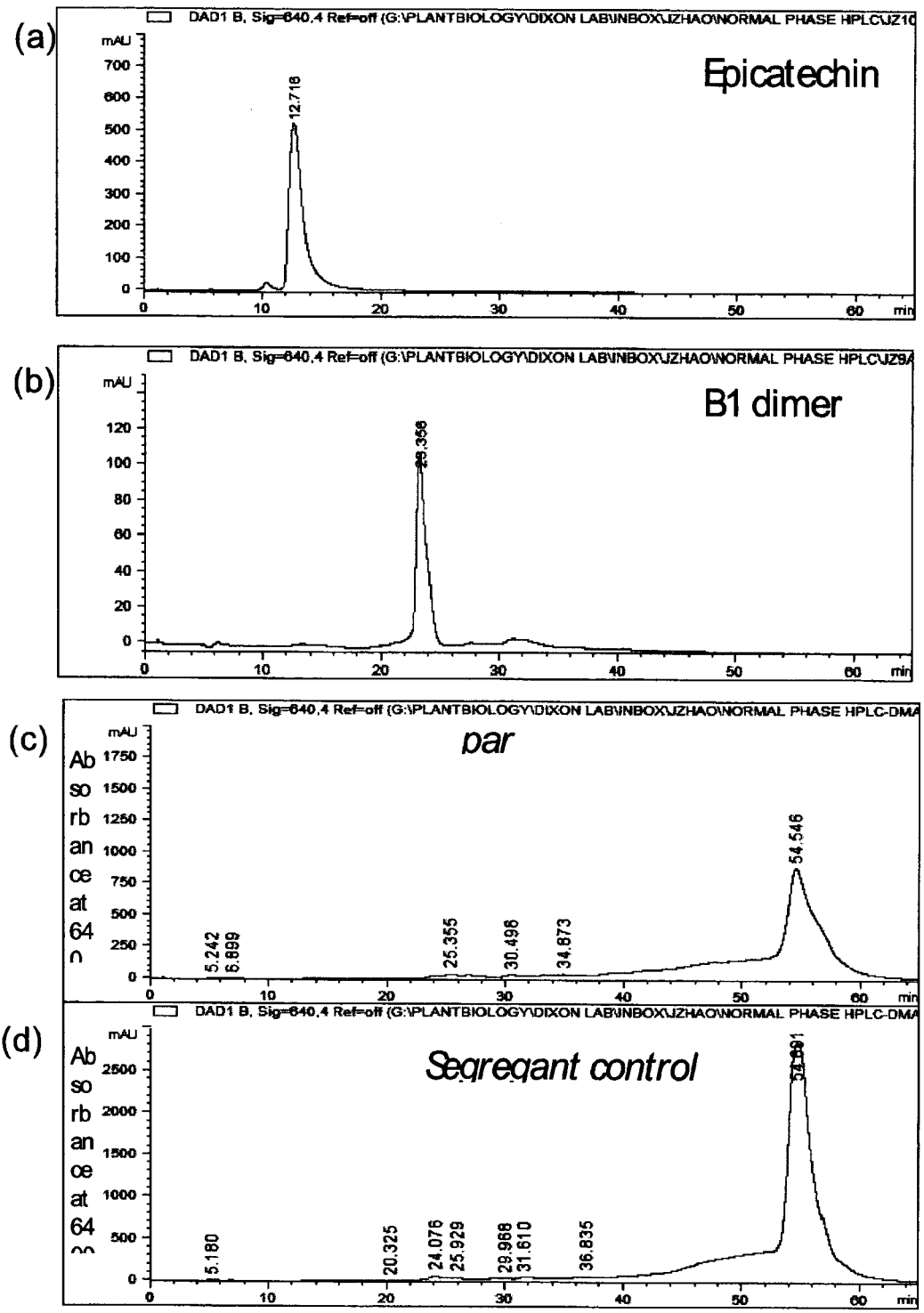
FIG. 5: Analysis of size distribution of PAs in *Medicago* lines (a-d) and hairy root lines (e-f). For (a-d), soluble PAs were resolved by normal phase HPLC with post-column derivatization DMACA reagent and monitoring at 640 nm. Standards of monomer (epicatechin) (a) and dimer (procyanidin B1) (b). (c) Soluble PAs from *M. truncatula* MtPAR Tnt1 mutant seeds. (d) PAs from *M. truncatula* null segregant control seeds. (e) Soluble PAs from *M. truncatula* hairy roots expressing GUS (control). (f) PAs from *M. truncatula* hairy root lines expressing MtPAR.
Figure 5:
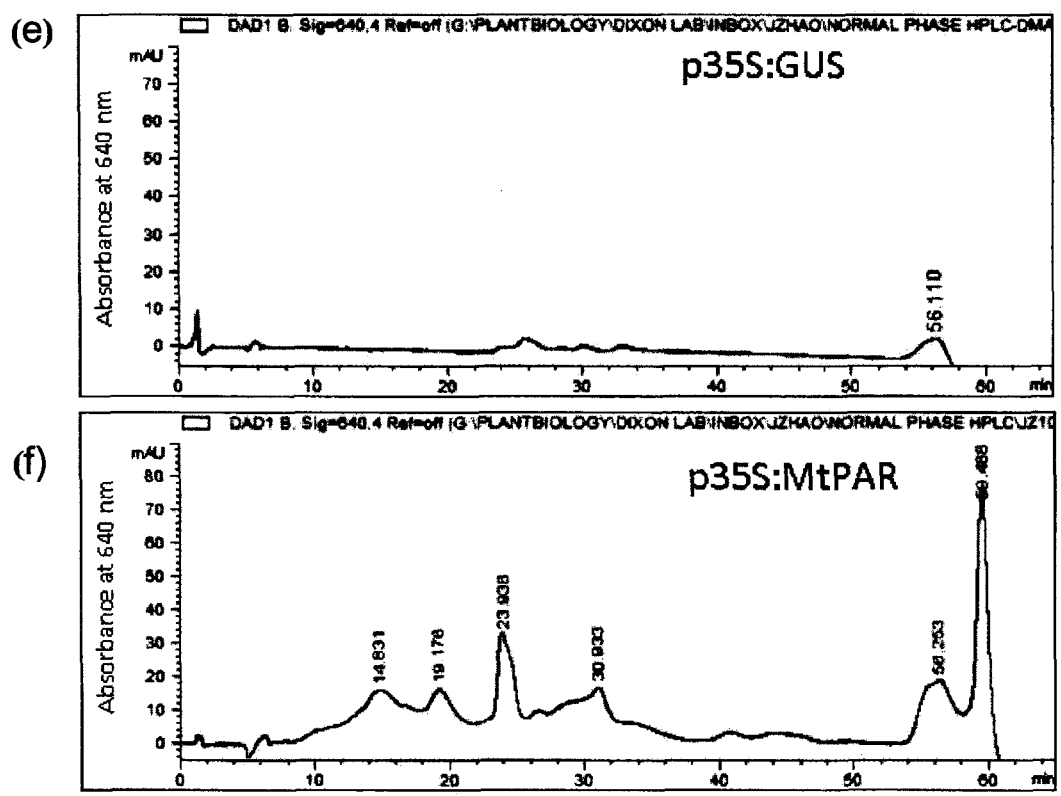

MtPAR plays a specific role in the regulation of PA biosynthesis in *Medicago* seeds. First, MtPAR1 gene expression was confined to the seed coat, the site of PA accumulation in developing seed (FIG. 1). Second, loss-of-function (Tnt1-insertion) par mutants accumulated substantially less PA in the seed coat than did wild-type controls (FIG. 2). Third, anthocyanin levels remained normal in par mutant seed (FIG. 2) despite the existence of a common pathway that generates precursors for PA and anthocyanin biosynthesis (see FIG. 5). Fourth, no aberrant phenotype apart from pale seed color was evident in any organ of par mutants. Fifth, ectopic overexpression of MtPAR1 in roots led to production of PA in an organ that normally does not accumulate PAs (FIG. 3). Sixth, genes that exhibited decreased expression (relative to wild-type) in the seed of par mutants and were expressed at a higher level in MtPAR over-expressing roots are largely involved in flavonoid and PA biosynthesis (FIGS. 4-5). These putative target genes of MtPAR protein activity include three CHS, two F3H, and the ANS genes, which are required for both PA and anthocyanin production, as well as the ANR gene, which is required for PA production alone (FIG. 4b, FIG. 5).

It was surprising that anthocyanin levels were unaffected while PA levels were substantially reduced in par mutant seed compared to the wild-type, given that many of the genes required for both PA and anthocyanin biosynthesis showed decreased expression in the mutant. Without being bound to any given theory, it may be that metabolic channeling explains these results. For example, if ANS and ANR were physically-coupled, the product of ANS activity, 3-OH-anthocyanidin, would be converted preferentially to epicatechin (and ultimately PA) by ANR, rather than being glycosylated for anthocyanin production (FIG. 5). In addition to the decrease in PA levels, an increase in flavonol glycosides was noted in par mutants (FIG. 5c), which coincided with an increase of 31.8% in transcript levels of FLS genes FLS genes may be regulated directly (negatively) by MtPAR, or regulation may be indirect, via a change in flavonoid pathway activity or metabolite levels for instance. Flavonoid content changes are indicated for instance in Table 7.

Some of the key genes/enzymes involved in *M. truncatula* PA biosynthesis have been characterized, including ANR, ANS and LAR (Xie et al., 2004; Pang et al., 2007). However, little is known about regulation of PA biosynthetic genes in *Medicago*. A single WD40-repeat TF, MtWD-40-1, orthologous to *Arabidopsis* AtTTG1, was identified as a positive regulator of PA biosynthesis in *M. truncatula* seeds (Pang et al., 2009). The action of MtWD-40-1 was compared with that of MtPAR in *M. truncatula* (e.g. see FIG. 6), and it appears that both genes may belong to the same regulatory network. For instance, both mutants exhibit a substantial decrease of PA levels in seed (FIG. 2d; Pang et al., 2009). Furthermore, transcriptomic analysis revealed that a common set of genes was down-regulated in mutants defective in these genes. Gene expression analysis also revealed a decrease of MtWD40-1 gene expression in par mutant lines (FIG. 6c), suggesting that MtPAR regulates MtWD40-1 expression. The converse was not the case, as MtPAR expression was not affected in wd40-1 mutants (Pang et al., 2009). This may explain why ectopic expression of MtPAR, but not of MtWD-40-1, resulted in PA biosynthesis in roots (FIG. 3). If a complex of TFs, including MtPAR and MtWD-40-1 is required to induce flavonoid biosynthesis genes, as is the case in *Arabidopsis* (Baudry et al., 2004), then ectopic expression of MtPAR, and consequent induction of MtWD-40-1 may have provided the requisite TFs for PA biosynthesis in roots. In contrast, ectopic expression of MtWD-40-1 would not induce MtPAR expression and would, therefore, fail to induce PA biosynthesis.

Many forage crops are low in PA, including *Medicago* spp. such as alfalfa and annual medics, white clover, ball clover, Persian clover, red clover, crimson clover, berseem clover, arrowleaf clover, alsike clover, subterranean clovers, fenugreek, and sweetclover (*Melilotus* spp.). Consumption of forage tissues low in PA can lead to "bloat." Similarly, bloat can be caused by grazing of wheat pastures and other lush foliage, such as fast-growing monocots. "Feedlot bloat" also occurs in cattle fed high-grain rations that may or may not contain legume forage, green-chopped legumes, or other finely ground feed. In these cases, direct engineering of PA accumulation in the forage plant may be used in accordance with the invention to prevent bloat. Further, PA modification could be engineered into feed components that are blended or added to bloat-causing components to reduce the bloat incidence in animals consuming the mixed feed. Specifically contemplated by the invention, is therefore the modification of any species that may be used in feed provided to animals, including monocot species such as corn, wheat, sorghum, and various grasses, among others.

One application of the invention is the modification of PA biosynthesis in plants with low PA content. Alfalfa is one such plant. Proanthocyanidins are made in alfalfa (*Medicago sativa*), as in *Arabidopsis*, in the seed coat, but do not accumulate in the leaves (Koupai-Abyazani et al., 1993; Skadhauge et al., 1997). Nonetheless, alfalfa is the world's major forage legume. Therefore, enhancing PA biosynthesis for instance in the leaves or other tissues of alfalfa or other low PA plants would substantially improve the utility of this crop for feed by reduction of its potential for causing pasture bloat. Forage crops that accumulate PAs in leaves have low bloating potential; these include *Lotus corniculatus, Leucaena leucocephala, Hedysarum sulfurescens* and *Robinia* spp.

Technology that could result in constitutive expression of PAs in high protein forage crops would also greatly improve the agronomic value of crops in addition to alfalfa. In addition, the potential importance of PAs in human health makes methods for their facile production in plants necessary for the full development of their therapeutic potential.

The present invention provides methods and compositions for increasing PAs comprising introducing transgenic MtPAR coding sequences. In certain aspects, this may be provided in combination with another coding sequence which functions to enhance PA biosynthesis in a plant.

I. Application of the Invention

As indicated above, one application of the invention is the introduction or increase of PA biosynthesis in plants. Such applications may result in forage improvement and nutritional improvement of foods. In accordance with the invention this may be carried out by introduction of MtPAR alone or in combination with other PA biosynthesis genes, regulatory or structural, such as described herein. The invention may thus be used to improve the nutritional quality of plants. Catechins and similar flavonoids have been reported to behave as strong antioxidants and have other properties which may make their consumption beneficial to human and animal health. Also, such compounds are generally antimicrobial, and their presence may improve food quality by preventing pre- and post-harvest damage. Accordingly, increases in PA biosynthesis may be used to achieve the associated health benefits.

In addition to providing the MtPAR gene alone, other genes may be used to enhance the accumulation of condensed tannins, especially in combination with MtWD40-1, ANS, ANR, or BAN/LAR expression. For example, MtPAR may be provided with MtWD40-1 (Pang et al., 2009; GenBank accession EU040206; SEQ ID NO:4). These sequences may find use with the invention as is described herein.

As indicated above, a modulation of the phenotype of a gene may be obtained in accordance with the invention by introduction of recombinant nucleic acids comprising a MtPAR coding sequence. Such a nucleic acid may be in the sense and/or antisense orientation. Also provided by the invention are MtPAR sequences that hybridize to the coding sequences provided herein under high stringency conditions. As used herein, "hybridization" or "hybridizes" is understood to mean the forming of a double or triple stranded molecule or a molecule with partial double or triple stranded nature. As used herein "stringent condition(s)" or "high stringency" are those conditions that allow hybridization between or within one or more nucleic acid strand(s) containing complementary sequence(s), but precludes hybridization of random sequences.

Stringent conditions tolerate little mismatch between a nucleic acid and a target strand. Such conditions are well known to those of ordinary skill in the art, and are preferred for applications requiring high selectivity. Medium stringent conditions may comprise relatively low salt and/or relatively high temperature conditions, such as provided by about 5×SSC, 50% formamide and 42° C.; or alternatively, 5×SSC, 50% formamide and 55° C. High stringency may be defined as 0.02M to 0.10M NaCl and 50° C. to 70° C. Specific examples of such conditions include 0.02M NaCl and 50° C.; 0.02M NaCl and 60° C.; and 0.02M NaCL and 70° C. Other examples of such conditions are 1×SSC, and 65° C.; or 0.2×-0.5×SSC and 65° C.

It is understood that the temperature and ionic strength of a desired stringency are determined in part by the length of the particular nucleic acid(s), the length and nucleobase content of the target sequence(s), the charge composition of the nucleic acid(s), and to the presence or concentration of formamide, tetramethylammonium chloride or other solvent(s) in a hybridization mixture. It is also understood that compositions and conditions for hybridization are mentioned by way of non-limiting examples only, and that the desired stringency for a particular hybridization reaction in a plant cell is often determined empirically by comparison to one or more positive or negative controls. Depending on the application envisioned it is preferred to employ varying conditions of hybridization to achieve varying degrees of selectivity of a nucleic acid towards a target sequence.

II. Plant Transformation Constructs

Certain embodiments of the current invention concern plant transformation constructs. For example, one aspect of the current invention is a plant transformation vector comprising a MtPAR coding sequence alone or in combination with one or more other flavonoid or PA biosynthesis gene(s). Examples of PA biosynthesis genes include BAN, PAP-1, TTG1 TTG2, TT1, and/or TT8 among others. Exemplary coding sequences of such genes for use with the invention are well known in the art.

In certain embodiments of the invention, coding sequences are provided operably linked to a heterologous promoter, in either sense or antisense orientation. Expression constructs are also provided comprising these sequences, as are plants and plant cells transformed with the sequences.

The construction of vectors which may be employed in conjunction with plant transformation techniques using these or other sequences according to the invention will be known to those of skill of the art in light of the present disclosure (see, for example, Sambrook et al., 1989; Gelvin et al., 1990). The techniques of the current invention are thus not limited to any particular nucleic acid sequences.

One beneficial use of the sequences provided by the invention will be in the alteration of plant phenotypes by genetic transformation with sense or antisense PA biosynthesis genes. The PA biosynthesis gene such as MtPAR may be provided with other sequences. Where an expressible coding region that is not necessarily a marker coding region is employed in combination with a marker coding region, one may employ the separate coding regions on either the same or different DNA segments for transformation. In the latter case, the different vectors are delivered concurrently to recipient cells to maximize cotransformation.

The choice of any additional elements used in conjunction with the PA biosynthesis coding sequences will often depend on the purpose of the transformation. One of the major purposes of transformation of crop plants is to add commercially desirable, agronomically important traits to the plant. As PAs are known to confer many beneficial effects on health, one such trait is increased biosynthesis of tannins. Alternatively, plants may be engineered to decrease synthesis of PA.

Vectors used for plant transformation may include, for example, plasmids, cosmids, YACs (yeast artificial chromosomes), BACs (bacterial artificial chromosomes) or any other suitable cloning system, as well as fragments of DNA therefrom. Thus when the term "vector" or "expression vector" is used, all of the foregoing types of vectors, as well as nucleic acid sequences isolated therefrom, are included. It is contemplated that utilization of cloning systems with large insert capacities will allow introduction of large DNA sequences comprising more than one selected gene. In accordance with the invention, this could be used to introduce genes corresponding to the entire PA biosynthetic pathway into a plant. Introduction of such sequences may be facilitated by use of bacterial or yeast artificial chromosomes (BACs or YACs, respectively), or even plant artificial chromosomes. For example, the use of BACs for *Agrobacterium*-mediated transformation was disclosed by Hamilton et al., (1996).

Particularly useful for transformation are expression cassettes which have been isolated from such vectors. DNA segments used for transforming plant cells will, of course, generally comprise the cDNA, gene or genes which one desires to introduce into and have expressed in the host cells. These DNA segments can further include structures such as promoters, enhancers, polylinkers, or even regulatory genes as desired. The DNA segment or gene chosen for cellular introduction will often encode a protein which will be expressed in the resultant recombinant cells resulting in a screenable or selectable trait and/or which will impart an improved phenotype to the resulting transgenic plant. However, this may not always be the case, and the present invention also encompasses transgenic plants incorporating non-expressed transgenes. Preferred components likely to be included with vectors used in the current invention are as follows.

A. Regulatory Elements

Exemplary promoters for expression of a nucleic acid sequence include plant promoter such as the CaMV 35S promoter (Odell et al., 1985), or others such as CaMV 19S (Lawton et al., 1987), nos (Ebert et al., 1987), Adh (Walker et al., 1987), sucrose synthase (Yang and Russell, 1990), a-tubulin, actin (Wang et al., 1992), cab (Sullivan et al., 1989), PEPCase (Hudspeth and Grula, 1989) or those associated with the R gene complex (Chandler et al., 1989). Tissue specific promoters such as root cell promoters (Conkling et al., 1990) and tissue specific enhancers (Fromm et al., 1986) are also contemplated to be particularly useful, as are inducible promoters such as ABA- and turgor-inducible promoters. In one embodiment of the invention, the native promoter of a PA biosynthesis gene is used.

The DNA sequence between the transcription initiation site and the start of the coding sequence, i.e., the untranslated leader sequence, can also influence gene expression. One may thus wish to employ a particular leader sequence with a transformation construct of the invention. Preferred leader sequences are contemplated to include those which comprise sequences predicted to direct optimum expression of the attached gene, i.e., to include a preferred consensus leader sequence which may increase or maintain mRNA stability and prevent inappropriate initiation of translation. The choice of such sequences will be known to those of skill in the art in light of the present disclosure. Sequences that are derived from genes that are highly expressed in plants will typically be preferred.

It is specifically envisioned that PA biosynthesis coding sequences may be introduced under the control of novel promoters or enhancers, etc., or homologous or tissue specific promoters or control elements. Vectors for use in tissue-specific targeting of genes in transgenic plants will typically include tissue-specific promoters and may also include other tissue-specific control elements such as enhancer sequences. Promoters which direct specific or enhanced expression in certain plant tissues will be known to those of skill in the art in light of the present disclosure. These include, for example, the rbcS promoter, specific for green tissue; the ocs, nos and mas promoters which have higher activity in roots or wounded leaf tissue; a truncated (−90 to +8) 35S promoter which directs enhanced expression in roots, and an α-tubulin gene that also directs expression in roots.

B. Terminators

Transformation constructs prepared in accordance with the invention will typically include a 3' end DNA sequence that acts as a signal to terminate transcription and allow for the poly-adenylation of the mRNA produced by coding sequences operably linked to a PA biosynthesis gene. In one embodiment of the invention, the native terminator of a PA biosynthesis gene is used. Alternatively, a heterologous 3' end may enhance the expression of sense or antisense PA biosynthesis genes. Terminators which are deemed to be particularly useful in this context include those from the nopaline synthase gene of *Agrobacterium tumefaciens* (nos 3' end) (Bevan et al., 1983), the terminator for the T7 transcript from the octopine synthase gene of *Agrobacterium tumefaciens*, and the 3' end of the protease inhibitor I or II genes from potato or tomato. Regulatory elements such as an Adh intron (Callis et al., 1987), sucrose synthase intron (Vasil et al., 1989) or TMV omega element (Gallie et al., 1989), may further be included where desired.

C. Transit or Signal Peptides

Sequences that are joined to the coding sequence of an expressed gene, which are removed post-translationally from the initial translation product and which facilitate the transport of the protein into or through intracellular or extracellular membranes, are termed transit (usually into vacuoles, vesicles, plastids and other intracellular organelles) and signal sequences (usually to the endoplasmic reticulum, golgi apparatus and outside of the cellular membrane). By facilitating the transport of the protein into compartments inside and outside the cell, these sequences may increase the accumulation of gene product protecting them from proteolytic degradation. These sequences also allow for additional mRNA sequences from highly expressed genes to be attached to the coding sequence of the genes. Since mRNA being translated by ribosomes is more stable than naked mRNA, the presence of translatable mRNA in front of the gene may increase the overall stability of the mRNA transcript from the gene and thereby increase synthesis of the gene product. Since transit and signal sequences are usually post-translationally removed from the initial translation product, the use of these sequences allows for the addition of extra translated sequences that may not appear on the final polypeptide. It further is contemplated that targeting of certain proteins may be desirable in order to enhance the stability of the protein (U.S. Pat. No. 5,545,818, incorporated herein by reference in its entirety).

Additionally, vectors may be constructed and employed in the intracellular targeting of a specific gene product within the cells of a transgenic plant or in directing a protein to the extracellular environment. This generally will be achieved by joining a DNA sequence encoding a transit or signal peptide sequence to the coding sequence of a particular gene. The resultant transit, or signal, peptide will transport the protein to a particular intracellular, or extracellular destination, respectively, and will then be post-translationally removed.

D. Marker Genes

By employing a selectable or screenable marker protein, one can provide or enhance the ability to identify transformants. "Marker genes" are genes that impart a distinct phenotype to cells expressing the marker protein and thus allow such transformed cells to be distinguished from cells that do not have the marker. Such genes may encode either a selectable or screenable marker, depending on whether the marker confers a trait which one can "select" for by chemical means, i.e., through the use of a selective agent (e.g., a herbicide, antibiotic, or the like), or whether it is simply a trait that one can identify through observation or testing, i.e., by "screening" (e.g., the green fluorescent protein). Of course, many examples of suitable marker proteins are known to the art and can be employed in the practice of the invention.

Included within the terms selectable or screenable markers also are genes which encode a "secretable marker" whose secretion can be detected as a means of identifying or selecting for transformed cells. Examples include markers which are secretable antigens that can be identified by antibody interaction, or even secretable enzymes which can be detected by their catalytic activity. Secretable proteins fall into a number of classes, including small, diffusible proteins detectable, e.g., by ELISA; small active enzymes detectable in extracellular solution (e.g., α-amylase, β-lactamase, phosphinothricin acetyltransferase); and proteins that are inserted or trapped in the cell wall (e.g., proteins that include a leader sequence such as that found in the expression unit of extensin or tobacco PR-S).

Many selectable marker coding regions are known and could be used with the present invention including, but not limited to, neo (Potrykus et al., 1985), which provides kanamycin resistance and can be selected for using kanamycin, G418, paromomycin, etc.; bar, which confers bialaphos or phosphinothricin resistance; a mutant EPSP synthase protein (Hinchee et al., 1988) conferring glyphosate resistance; other such selectable marker coding regions are well known in the art.

III. Antisense and RNAi Constructs

Antisense and RNAi treatments represent one way of altering PA biosynthesis in accordance with the invention. In particular, constructs comprising a PA biosynthesis gene and/or a promoter thereof in antisense orientation may be used to decrease or effectively eliminate the expression of PA in a plant. Accordingly, this may alternatively be used to increase anthocyanin accumulation in a plant or given plant tissue. As such, antisense technology may be used to "knock-out" the function of a PA biosynthesis gene or homologous sequences thereof.

Antisense methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

RNA interference (RNAi) is a process utilizing endogenous cellular pathways whereby a double stranded RNA (dsRNA) specific target gene results in the degradation of the mRNA of interest. In recent years, RNAi has been used to perform gene "knockdown" in a number of species and experimental systems, from the nematode C. elegans, to plants, to insect embryos and cells in tissue culture (Fire et al., 1998; Martinez et al., 2002; McManus and Sharp, 2002). RNAi works through an endogenous pathway including the Dicer protein complex that generates ~21-nucleotide small interfering RNAs (siRNAs) from the original dsRNA and the RNA-induced silencing complex (RISC) that uses siRNA guides to recognize and degrade the corresponding mRNAs. Only transcripts complementary to the siRNA are cleaved and degraded, and thus the knock-down of mRNA expression is usually sequence specific. One of skill in the art would routinely be able to identify portions of, for instance, MtPAR sequence, as targets for RNAi-mediated gene suppression.

Targeting double-stranded (ds) DNA with polynucleotides may lead to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription or translation or both within a host cell.

Antisense or RNAi constructs may be targeted to promoter and other control regions, exons, introns or even exon-intron boundaries of a gene. It is contemplated that the certain effective constructs will include regions complementary to intron/exon splice junctions. Thus, one example of a construct may comprise complementarity to regions within 50-200 bases of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an antisense construct which has limited regions of high homology, but also contains a non-homologous region (e.g., ribozyme; see above) could be designed. These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

IV. Tissue Cultures

Tissue cultures may be used in certain transformation techniques for the preparation of cells for transformation and for the regeneration of plants therefrom. Maintenance of tissue cultures requires use of media and controlled environments. "Media" refers to the numerous nutrient mixtures that are used to grow cells in vitro, that is, outside of the intact living organism. The medium usually is a suspension of various categories of ingredients (salts, amino acids, growth regulators, sugars, buffers) that are required for growth of most cell types.

Methods for plant cell culture, including preparing and using nutrient media, such as a liquid medium or a solid medium, are well known in the art. Manual selection of recipient cells, e.g., by selecting embryogenic cells from the surface of a callus, is one means that may be used in an attempt to enrich for particular cells prior to culturing (whether cultured on solid media or in suspension). Where employed, cultured cells may be grown either on solid supports or in the form of liquid suspensions. In either instance, nutrients may be provided to the cells in the form of media, and environmental conditions controlled. There are many types of tissue culture media comprised of various amino acids, salts, sugars, growth regulators and vitamins. Most of the media employed in the practice of the invention will have some similar components, but may differ in the composition and proportions of their ingredients depending on the particular application envisioned. Various types of media suitable for culture of plant cells previously have been described. Examples of these media include, but are not limited to, the N6 medium described by Chu et al., (1975) and MS media (Murashige and Skoog, 1962).

V. Methods for Genetic Transformation

Suitable methods for transformation of plant or other cells for use with the current invention are well known, and are believed to include virtually any method by which DNA can be introduced into a cell, such as by Agrobacterium-mediated transformation (U.S. Pat. No. 5,591,616 and U.S. Pat. No. 5,563,055; both specifically incorporated herein by reference) and by acceleration of DNA coated particles. Through the application of techniques such as these, the cells of virtually any plant species may be stably transformed, and these cells developed into transgenic plants. In those plant strains where *Agrobacterium*-mediated transformation is efficient, it is often the method of choice because of the facile and defined nature of the gene transfer.

VI. Production and Characterization of Stably Transformed Plants

After effecting delivery of exogenous DNA to recipient cells, the next steps generally concern identifying the transformed cells for further culturing and plant regeneration. In order to improve the ability to identify transformants, one may desire to employ a selectable or screenable marker gene with a transformation vector prepared in accordance with the invention. In this case, one would then generally assay the potentially transformed cell population by exposing the cells to a selective agent or agents, or one would screen the cells for the desired marker gene trait.

It is contemplated that using the techniques of dot or slot blot hybridization which are modifications of Southern hybridization techniques one could obtain the same information that is derived from PCR™, e.g., the presence of a gene. Both PCR™ and Southern hybridization techniques can be used to demonstrate transmission of a transgene to progeny. In most instances the characteristic Southern hybridization pattern for a given transformant will segregate in progeny as one or more Mendelian genes (Spencer et al., 1992) indicating stable inheritance of the transgene.

Whereas DNA analysis techniques may be conducted using DNA isolated from any part of a plant, RNA will only be expressed in particular cells or tissue types and hence it will be necessary to prepare RNA for analysis from these tissues. PCR™ techniques also may be used for detection and quantitation of RNA produced from introduced genes. In this application of PCR™ it is first necessary to reverse transcribe RNA into DNA, using enzymes such as reverse transcriptase, and then through the use of conventional PCR™ techniques amplify the DNA. In most instances PCR™ techniques, while useful, will not demonstrate integrity of the RNA product. Further information about the nature of the RNA product may be obtained by Northern blotting. This technique will demonstrate the presence of an RNA species and give information about the integrity of that RNA. The presence or absence of an RNA species also can be determined using dot or slot blot Northern hybridizations. These techniques are modifications of Northern blotting and will only demonstrate the presence or absence of an RNA species.

While Southern blotting and PCR™ may be used to detect the gene(s) in question, they do not provide information as to whether the corresponding protein is being expressed. Expression may be evaluated by specifically identifying the protein products of the introduced genes or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as western blotting in which antibodies are used to locate individual gene products that have been separated by electrophoretic techniques. Additional techniques may be employed to absolutely confirm the identity of the product of interest such as evaluation by amino acid sequencing following purification. Although these are among the most commonly employed, other procedures may be additionally used.

Assay procedures also may be used to identify the expression of proteins by their functionality, especially the ability of enzymes to catalyze specific chemical reactions involving specific substrates and products. These reactions may be followed by providing and quantifying the loss of substrates or the generation of products of the reactions by physical or chemical procedures. Examples are as varied as the enzyme to be analyzed and may include assays for PAT enzymatic activity by following production of radiolabeled acetylated phosphinothricin from phosphinothricin and $^{14}$C-acetyl CoA or for anthranilate synthase activity by following loss of fluorescence of anthranilate, to name two.

Very frequently the expression of a gene product is determined by evaluating the phenotypic results of its expression. These assays also may take many forms including but not limited to analyzing changes in the chemical composition, morphology, or physiological properties of the plant. Chemical composition may be altered by expression of genes encoding enzymes or storage proteins which change amino acid composition and may be detected by amino acid analysis, or by enzymes which change starch quantity which may be analyzed by near infrared reflectance spectrometry. Morphological changes may include greater stature or thicker stalks. Most often changes in response of plants or plant parts to imposed treatments are evaluated under carefully controlled conditions termed bioassays.

VII. Breeding Plants of the Invention

In addition to direct transformation of a particular plant genotype with a construct prepared according to the current invention, transgenic plants may be made by crossing a plant having a selected DNA of the invention to a second plant lacking the construct. For example, a selected PA biosynthesis gene can be introduced into a particular plant variety by crossing, without the need for ever directly transforming a plant of that given variety. Therefore, the current invention not only encompasses a plant directly transformed or regenerated from cells which have been transformed in accordance with the current invention, but also the progeny of such plants. As used herein the term "progeny" denotes the offspring of any generation of a parent plant prepared in accordance with the instant invention, wherein the progeny comprises a selected DNA construct prepared in accordance with the invention. "Crossing" a plant to provide a plant line having one or more added transgenes relative to a starting plant line, as disclosed herein, is defined as the techniques that result in a transgene of the invention being introduced into a plant line by crossing a starting line with a donor plant line that comprises a transgene of the invention. To achieve this one could, for example, perform the following steps:

(a) plant seeds of the first (starting line) and second (donor plant line that comprises a transgene of the invention) parent plants;

(b) grow the seeds of the first and second parent plants into plants that bear flowers;

(c) pollinate a flower from the first parent plant with pollen from the second parent plant; and (d) harvest seeds produced on the parent plant bearing the fertilized flower.

Backcrossing is herein defined as the process including the steps of:

(a) crossing a plant of a first genotype containing a desired gene, DNA sequence or element to a plant of a second genotype lacking the desired gene, DNA sequence or element;

(b) selecting one or more progeny plant containing the desired gene, DNA sequence or element;

(c) crossing the progeny plant to a plant of the second genotype; and (d) repeating steps (b) and (c) for the purpose of transferring a desired DNA sequence from a plant of a first genotype to a plant of a second genotype.

Introgression of a DNA element into a plant genotype is defined as the result of the process of backcross conversion. A plant genotype into which a DNA sequence has been introgressed may be referred to as a backcross converted genotype, line, inbred, or hybrid. Similarly a plant genotype lacking the desired DNA sequence may be referred to as an unconverted genotype, line, inbred, or hybrid.

VIII. Definitions

Proanthocyanidin (PA) biosynthesis gene: A gene encoding a polypeptide that catalyzes one or more steps in the biosynthesis of proanthocyanidins (condensed tannins), or regulates expression or activity of such a gene.

Expression: The combination of intracellular processes, including transcription and translation undergone by a coding DNA molecule such as a structural gene to produce a polypeptide.

Genetic Transformation: A process of introducing a DNA sequence or construct (e.g., a vector or expression cassette) into a cell or protoplast in which that exogenous DNA is incorporated into a chromosome or is capable of autonomous replication.

Heterologous: A sequence which is not normally present in a given host genome in the genetic context in which the sequence is currently found In this respect, the sequence may be native to the host genome, but be rearranged with respect to other genetic sequences within the host sequence. For example, a regulatory sequence may be heterologous in that it is linked to a different coding sequence relative to the native regulatory sequence.

Obtaining: When used in conjunction with a transgenic plant cell or transgenic plant, obtaining means either transforming a non-transgenic plant cell or plant to create the transgenic plant cell or plant, or planting transgenic plant seed to produce the transgenic plant cell or plant. Such a transgenic plant seed may be from an $R_0$ transgenic plant or may be from a progeny of any generation thereof that inherits a given transgenic sequence from a starting transgenic parent plant.

Promoter: A recognition site on a DNA sequence or group of DNA sequences that provides an expression control element for a structural gene and to which RNA polymerase specifically binds and initiates RNA synthesis (transcription) of that gene.

$R_0$ transgenic plant: A plant that has been genetically transformed or has been regenerated from a plant cell or cells that have been genetically transformed.

Regeneration: The process of growing a plant from a plant cell (e.g., plant protoplast, callus or explant).

Selected DNA: A DNA segment which one desires to introduce into a plant genome by genetic transformation.

Transformation construct: A chimeric DNA molecule which is designed for introduction into a host genome by genetic transformation. Preferred transformation constructs will comprise all of the genetic elements necessary to direct the expression of one or more exogenous genes. In particular embodiments of the instant invention, it may be desirable to introduce a transformation construct into a host cell in the form of an expression cassette.

Transformed cell: A cell the DNA complement of which has been altered by the introduction of an exogenous DNA molecule into that cell.

Transgene: A segment of DNA which has been incorporated into a host genome or is capable of autonomous replication in a host cell and is capable of causing the expression of one or more coding sequences. Exemplary transgenes will provide the host cell, or plants regenerated therefrom, with a novel phenotype relative to the corresponding non-transformed cell or plant. Transgenes may be directly introduced into a plant by genetic transformation, or may be inherited from a plant of any previous generation which was transformed with the DNA segment.

Transgenic plant: A plant or progeny plant of any subsequent generation derived therefrom, wherein the DNA of the plant or progeny thereof contains an introduced exogenous DNA segment not naturally present in a non-transgenic plant of the same strain. The transgenic plant may additionally contain sequences which are native to the plant being transformed, but wherein the "exogenous" gene has been altered in order to alter the level or pattern of expression of the gene, for example, by use of one or more heterologous regulatory or other elements.

Vector: A DNA molecule capable of replication in a host cell and/or to which another DNA segment can be operatively linked so as to bring about replication of the attached segment. A plasmid is an exemplary vector.

IX. Examples

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

MtPAR Encodes a MYB Transcription Factor with Seed Coat-Specific Expression

The *M. truncatula* Gene Expression Atlas ("MtGEA") was used to select seed-induced transcription factor ("TF") genes for genetic characterization. The MtPAR gene was identified by its seed-specific expression profile (probeset ID Mtr.50541.1.S1_at), using the *Medicago truncatula* Gene Expression Atlas webserver (www.mtgea.noble.org; Benedito et al., 2008; He et al., 2009). Alignment of the deduced amino acid sequences of MtPAR and other proteins of the MYB R2R3 family was carried out using ClustalW in the Geneious software suite (www.Biomatters.com; Biomatters, Auckland, NZ). The phylogenetic tree was built using a Neighbor-Joining algorithm with 100 bootstrap replicates. The R2R3 domain of each MYB factor was identified using the PFAM protein family database (Bateman et al., 2002). GeneBank accession numbers of all amino acid sequences are provided in Table 1.

TABLE 1

GeneBank accession numbers of amino acid sequences used for preparing alignments of FIG. 1c.

| Annotation | Name | Length |
|---|---|---|
| Q9ZTC3.1 | MYB90 Protein | 340 |
| PmMBF1 | MYB-like transcriptional factor MBF1 Protein | 409 |
| P27900.2 | GL1 Protein | 316 |
| NP_199744.1 | AtMYB111 (myb domain protein 111); DNA binding/transcription factor | 388 |
| NP_196979.1 | ATMYB66 (MYB DOMAIIN PROTEIN 66); DNA binding/protein binding/transcription factor/transcription regulator | 316 |
| NP_188966.1 | MYB15 (MYB DOMAIN PROTEIN 15); DNA binding/transcription factor | 395 |
| NP_182268.1 | MYB12 (MYB DOMAIN PROTEIN 12); DNA binding/transcription activator/transcription factor | 388 |
| NP_176057.1 | PAP1 (PRODUCTION OF ANTHOCYANIN PIGMENT 1); DNA binding/transcription factor protein | 340 |
| CAJ90831.1 | MYBPA1 protein | 388 |
| BAI49719.1 | Putative MYB transcription factor Protein | 351 |
| BAD18978.1 | myb-related transcription factor VvMYBA2 Protein | 360 |
| BAD18977.1 | Myb-related transcription factor VvMYBA1 Protein | 354 |
| BAA21619.1 | ATMYB4 Protein | 394 |
| ACN79542.1 | MYB transcription factor LAP3 Protein | 358 |
| ACN79541.1 | MYB transcription factor LAP1 Protein | 359 |
| ACN79540.1 | MYB transcription factor LAP4 Protein | 361 |
| ACN79539.1 | MYB transcription factor LAP2 Protein | 355 |
| ABB83828.1 | VENOSA Protein | 300 |
| ABB83827.1 | ROSEA2 Protein | 327 |
| ABB83826.1 | ROSEA1 Protein | 317 |
| AAV98200.1 | MYB-like protein ODORANT1 | 390 |
| AAS68190.1 | Myb transcription factor Protein | 404 |
| AAQ55181.1 | anthocyanin 1 Protein | 363 |
| AAB49039.1 | c-myb Protein | 643 |

The gene for one of these MYB TFs, termed MtPAR, encodes a putative MYB TF of the R2R3 class based on the presence of highly-conserved R2 and R3 MYB DNA-binding domains at the N-terminal end of the protein (FIG. 1b) (Stracke et al. 2001). MtPAR was expressed in a seed-specific manner, with maximal expression at 24 days after pollination (DAP; FIG. 1a). We used quantitative reverse-transcription polymerase chain reaction (qRT-PCR) to measure MtPAR transcript levels in dissected seed tissues and found that the gene was expressed in the seed coat but not in the embryo or endosperm (FIG. 1d). Phylogenetic analysis revealed no close relationship between MtPAR and MYB TFs involved in the regulation of anthocyanin (e.g. LAP proteins from *M. truncatula* or ANTHOCYANIN1 from *S. lycopersicum*; Peel et al., 2009; U.S. Patent Appl. Publ. 2005/0203033) or proanthocyanidin biosynthesis (e.g. TRANSPARENT TESTA2 from *A. thaliana* (GenBank Accession AJ299452); or U.S. Pat. No. 7,709,701) or MYBPA1 and MYBPA2 from *V. vinifera*; FIG. 1c; Nesi et al., 2001; Tether et al., 2009). The closest homolog of MtPAR was a MYB protein (Gm-MYB115, GenBank Accession QOPJG9) from *G. max* (soybean) of unknown function.

Example 2

Par Mutants are Defective in Seed Coat PA Accumulation

Four independent mutants with retrotransposon-insertions in the MtPAR gene were isolated via a PCR-screen of DNA from a Tnt1-insertion mutant population (Tadege et al. 2008). Generation of the *Medicago truncatula* Tnt1 insertional mutant population and growth of $R_1$ seeds were as described previously (Tadege et al. 2008). Reverse genetic screening for Tnt1 retrotransposon insertions in MtPAR was performed using a nested PCR approach (Cheng et al., 2011). PCR products from target mutant lines were purified with QIAquick™ PCR purification kit (Qiagen) and sequenced using Tnt1 primers to confirm insertions in MtPAR. The primers used were:

```
F1:
                                    (SEQ ID NO: 5)
     TGAGTGGCAGTGGAGTGTTT;

F2:
                                    (SEQ ID NO: 6)
     TAAAGGTGCTTGGTCTCGTGAA,

R1:
                                    (SEQ ID NO: 7)
     GGTCTCTAATTTTCCGTCAC,
and R2:
                                    (SEQ ID NO: 8)
     GGTCCCCTCATTGGAATAAATC.
```

Tnt1 insertions were found in the second exon of MtPAR1 in mutant line NF4419 and in the third exon in lines NF2466, NF1358, NF3308 (FIG. 3a). Homozygous insertion mutants of all four lines exhibited the same phenotype, namely a reduction in pigmentation of mature seed compared to the wild-type control (FIG. 2b and FIG. 2a). MtPAR transcript levels in developing seed of the four mutants were less than 5% of the wild-type level, as determined by qRT-PCR (FIG. 2b).

4-Dimethylaminocinnamaldehyde (DMACA) and vanillin staining was performed to evaluate qualitative changes in PA and anthocyanin contents of mature seeds. Seeds were stained overnight and destained in ethanol for observation.

Mature seeds (about 200 mg) of par homozygous mutants and their corresponding null segregant controls, or hairy roots (about 150 mg fresh weight) expressing MtPAR or GUS (as control). For analysis of anthocyanins in mature seeds or hairy roots (16d after subculture), about 200 mg mature seeds or 150 mg fresh hairy roots were ground into powder in liquid nitrogen and extracted three times with 300 µl of methanol containing 0.1% HCl by sonicating for 40 min each time. Pooled extracts were further extracted with an equal volume of chloroform, and the aqueous portion was used for spectrophotometer analysis of anthocyanin at 530 nm absorbance with a spectrophotometer with cyanidin 3-O-glucoside as standard. Epicatechin was used as standard for soluble PA quantification, and the PA dimer procyanidin B1 was used as standard for insoluble PAs. Reverse-phase HPLC for analysis of cyanidin products of butanol-HCl hydrolysis of insoluble PAs and normal phase HPLC coupled to post-column DMACA-derivatization for analysis of composition of soluble PAs in plant samples were conducted as described previously (Zhao and Dixon, 2010). Results of extraction and analysis of flavonoids from seeds and hairy roots of *M. trun-*

*catula* by UV spectroscopy; DMACA staining; and reverse phase or normal phase HPLC coupled to post-column DMACA-derivatization, UV diode array detection, or mass spectrometry are shown in FIGS. 4-5.

For measurement of flavonoid content, metabolites were extracted from 10.0±0.1 mg of dried mature seeds with 2 ml of 80% methanol containing 18 µg/ml of umbelliferone as internal standard, for 2 h at room temperature. After centrifugation, the supernatants were analyzed using a Waters Acquity HPLC system fitted with a quadrupole time of flight (Q-TOF) Premier mass spectrometer, according to Sumner et al. (2007). Masses of eluted compounds were detected in the negative ESI mode (Sumner et al., 2007). Metabolites were identified based on mass and retention time relative to authentic standards. Relative abundances were calculated using MET-IDEA (Broeckling et al., 2006) and peaks were normalized by dividing each peak area by the value of the internal standard peak area.

The staining indicated a decrease in the proanthocyanidin (PA) content of mature mutant seeds compared to the wild-type (FIG. 2c), whereas vanillin staining revealed no apparent difference in the anthocyanin content between mutant and wild-type seeds (FIG. 2c). DMACA staining of developing seed revealed gradual accumulation of PA from 10 to 16 DAP in both mutant and wild-type. Differences between mutant and wild-type in DMACA-staining of seed first became apparent around 20-24 DAP (FIG. 6a), which coincided with maximal MtPAR expression in the wild-type. DMACA staining was confined largely to seed coats, mirroring the tissue-specificity of MtPAR expression (FIG. 6b).

To confirm that the different seed color between par and sibling wild-type was caused by PA levels, we quantified seed PA content in par mutants and their segregant controls. Both soluble and insoluble PA levels in par seeds were significantly reduced as compared to their segregant controls. Soluble PA content was about 50% lower, and insoluble PA content up to 80% lower in the mutants than in the sibling wild-types (FIG. 3d). We also subjected samples to high performance liquid chromatography (HPLC) followed by post-column DMACA-derivatisation to fractionate soluble PAs. Levels of insoluble PAs were detected by measurement of cyanidines revealed after butanol-HCl hydrolysis. Mutant and wild-type seed exhibited a similar spectrum of PAs (FIG. 4). However, the PA content of seeds was much lower in the par mutants. In contrast, spectrophotometer analysis of anthocyanin content was not significantly different between par mutant and wild-type seeds (FIG. 3e). These results indicate that MtPAR regulates proanthocyanidin but not anthocyanin biosynthesis in seeds.

Example 3

Ectopic Expression of MtPAR Induces Pa Biosynthesis

MtPAR Regulates Expression of Pa Biosynthesis Genes

To demonstrate a role for MtPAR in PA biosynthesis, *M. truncatula* roots were transformed with the MtPAR cDNA coupled to the constitutively-active CaMV-35S promoter (Odell et al., 1985).

The open reading frame (ORF) of MtPAR was amplified from cDNA synthesized from developing pods of ecotype R108 using the Trizol® RNA extraction method (Invitrogen) and Superscript III reverse transcriptase (Invitrogen). The primer sequences used for amplification were forward primer: ATGGTTAGAAGTCCTAAGGAGGTT (SEQ ID NO:9); and reverse primer: TCAATCATTTTCAAGTC-CAAGAAAG (SEQ ID NO:10). PCR products were cloned into the entry vector pENTR/D/TOPO (Invitrogen). After sequencing to validate the sequence of MtPAR in the entry vector, the ORF was recombined into a destination vector, pB7WG2D using the LR clonase reaction (Invitrogen). The GUS gene was also recombined into pB7WG2D vector, which was then used as a control for the hairy root transformation.

pB7WG2D vectors harboring MtPAR or GUS sequences were transformed into *Agrobacterium rhizogenes* strain ARqua 1 by electroporation (Quandt et al., 1993). Transformed colonies were grown on LB-agar medium at 28° C., with spectinomycin and streptomycin for vector selection. After confirmation by PCR, transformed Agrobacteria were used to transform leaves of *M. truncatula* (cv. Jemalong A17). The resulting hairy roots were maintained on B5 agar media in Petri dishes supplied with 7.5 mg/l phosphinothricin under fluorescent light (140 µE/m$^2$·s$^1$) with a 16-h photoperiod, and were sub-cultured every 20 days onto fresh media. Screening of hairy root clones was done by observation under UV light for GFP signal, by staining with DMACA reagent for presence of PAs, and by qRT-PCR analysis to detect and quantify the MtPAR transcript level.

Figure 7:
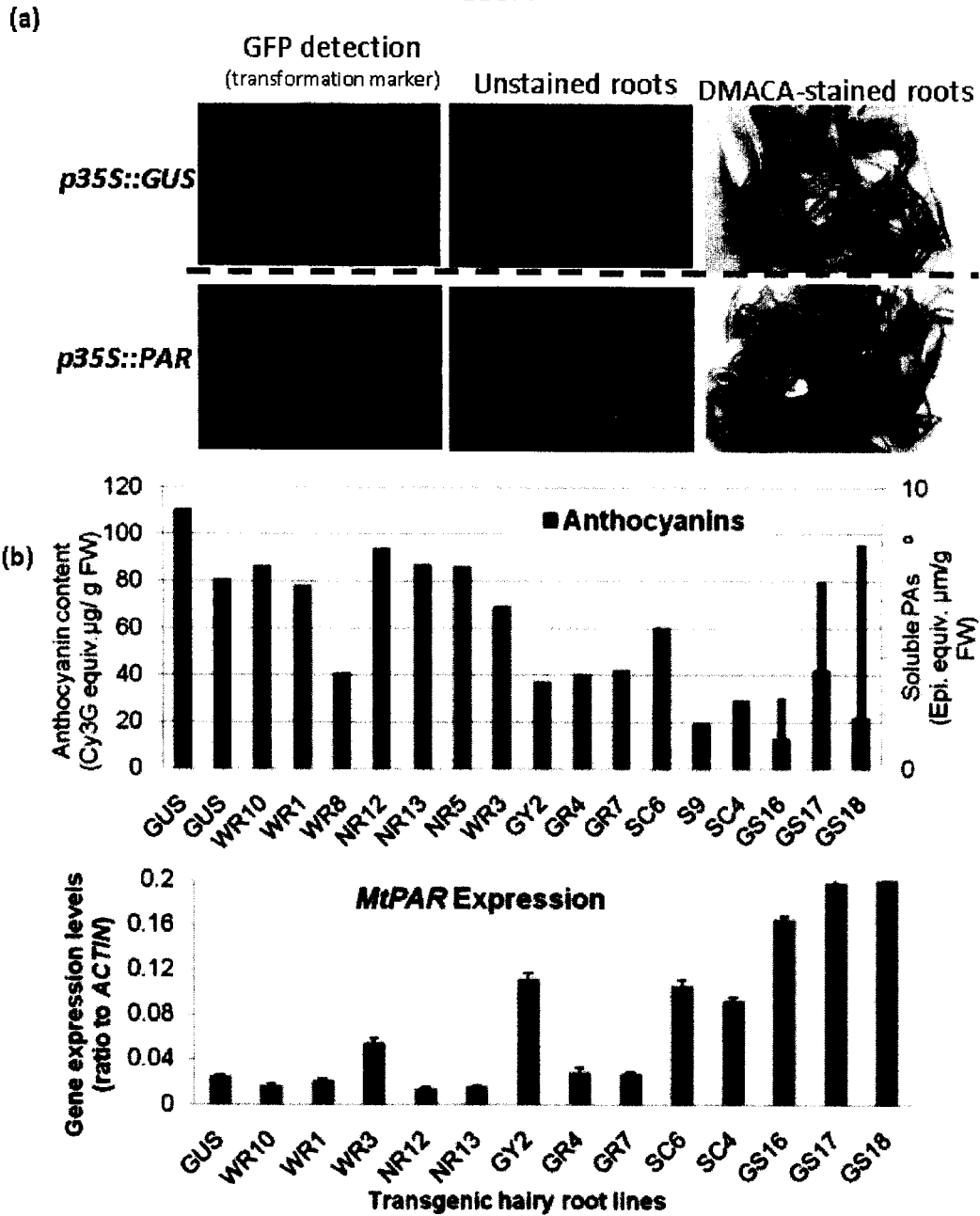
FIG. 7: (a) Phenotype of MtPAR ectopic expression transformants in Hairy roots: GFP detection as a transformation marker; Unstained and DMACA-stained hairy roots; (b) Levels of extractable soluble Pas and anthocyanins from hairy roots over-expressing MtPAR or GUS. Values are mean and standard deviations from three biological replicates.
Figure 8:
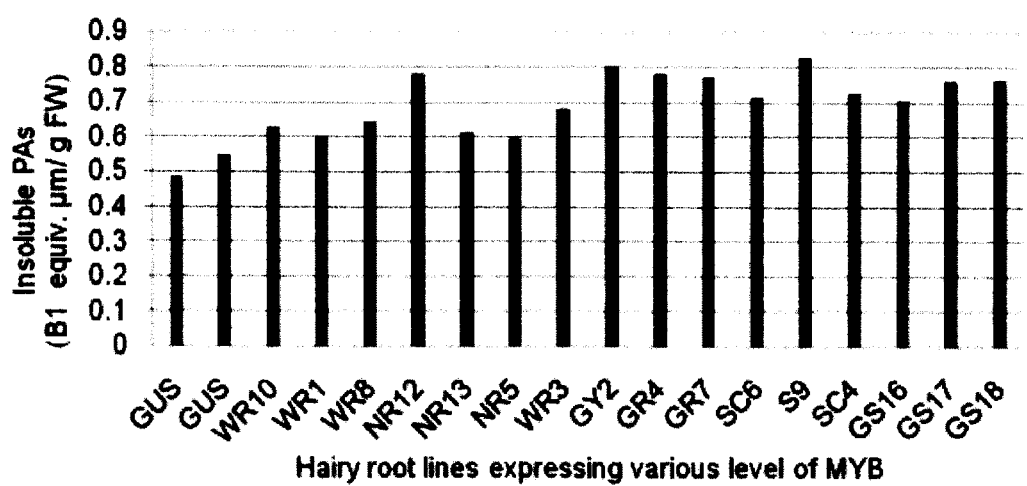
FIG. 8: Insoluble PA content in different hairy roots lines over-expressing MtPAR.

*Agrobacterium rhizogenes* (strain ARqua 1, Quandt et al., 1993) was used to transfer the p35S::MtPAR construct into *M. truncatula* together with a Green Fluorescent Protein (GFP) gene that enabled identification of transformed hairy roots (FIG. 7a). Ectopic expression of MtPAR in *Medicago* hairy roots was checked by qRT-PCR (FIG. 8). Initial observations of unstained hairy roots revealed an increase in red pigmentation in transgenic roots containing the p35S::MtPAR construct compared to control transformed roots containing a p35S::GUS (β-glucuronidase; Jefferson et al., 1987) construct (FIG. 7a). No differences in root growth or other morphological features were observed between p35S::MtPAR-containing and control plants. Subsequent staining of hairy roots with DMACA revealed a dramatic difference between p35S::MtPAR- and p35S::GUS-transformed roots. The former stained dark green with DMACA, whereas the latter (control) did not (FIG. 3a

Quantitative analysis of PA content confirmed that ectopic expression of MtPAR induced PA biosynthesis in hairy roots. Soluble PA levels were low in hairy roots of control transformed plants (p35S:: GUS) but were up to 100-fold higher in some p35S::MtPAR lines (FIG. 7b). A positive correlation was observed between soluble PA content and MtPAR transcript levels in the different transgenic lines (FIG. 7b). However, no significant difference in levels of insoluble PA was found between control and p35S::MtPAR lines (FIG. 8). Anthocyanin content was relatively high in hairy roots of control plants but decreased with increasing soluble PA levels in p35S::MtPAR lines.

To determine the mechanism by which MtPAR triggers PA biosynthesis, transcriptome analysis of mutant and wild-type seeds and of p35S::MtPAR- and p35S::GUS-transformed roots was performed, using Affymetrix *Medicago* GENE-CHIPs. Total RNA was isolated from developing seeds using a modified CTAB method (Verdier et al., 2008) and from hairy roots using Trizol reagent, according to the manufacturer's instructions (Invitrogen). Ten µg of total RNA from each sample were DNAse treated (Turbo DNAse, Ambion, Austin, Tex.) and partially purified (RNeasy MinElute Cleanup kit, Qiagen), according to manufacturer's instructions. Five hundred ng of purified RNA for each of the three biological replicates was used for probe synthesis using a GeneChip 3' IVT express kit, according to manufacturer's instructions (Affymetrix, Santa Clara, Calif.). Hybridization of probes to Affymetrix GeneChip® *Medicago* genome arrays and scanning of arrays was carried out as described previously (Benedito et al., 2008). Raw data were normalized by robust multichip averaging (RMA), as described in Irizarry et al. (2003). Presence and absence calls for probesets were obtained using the dCHIP algorithm (Li and Wong, 2001). Differentially-expressed genes in mutant and over-expressing lines were identified using the associative analysis described in Dozmorov and Centola (2003). Type I family-wise error rate was reduced by using a Bonferroni corrected p-value (threshold 0.05). False discovery rate was controlled by calculating the q-value using extraction of differential gene expression (EDGE, Biostat, Leek et al., 2005). To identify differentially regulated probesets, we used a p-value threshold of 5% and at least a 2-fold difference between transformant/mutant lines and their respective controls.

qRT-PCR analysis was performed using cDNA synthesized by SuperScript III from 2 µg of DNAse treated RNA, according to manufacturer's instructions (Invitrogen). Amplification reactions were performed in 5 µl final volume containing 2.5 µl of Power SYBR mastermix (Applied Biosystems), 1 µl of primers (0.5 µM of each primers) and 1.5 µl of 1:30 diluted cDNA. qRT-PCR data were generated using an Applied Biosystems 7900HT instrument and analyzed using SDS software (Applied Biosystems). PCR efficiencies were calculated using the LinReg software (Ramakers et al., 2003). Transcript levels were normalized using the geometric average of two housekeeping genes, MSC27 (TC85211) and PDF2 (TC107161) (Verdier et al., 2008). Primer sequences used were: primer pair for MSC27: GTTGAAGTAGACAT-TGGTGCTAACG (SEQ ID NO:11) and AGCTGAGTCAT-CAACACCCTCAT (SEQ ID NO:12); and primer pair for PDF2: GTGTTTTGCTTCCGCCGTT (SEQ ID NO:13), and CCAAATCTTGCTCCCTCATCTG (SEQ ID NO:14). Additional primers for qRT-PCR were:

```
WD40 qPCR Forward primer:
                                 (SEQ ID NO: 15)
ACCAACTACACCGGTCGCGG, WD40 qPCR Reverse primer:
                                 (SEQ ID NO: 16)
GCTACAGCCGGCAACTCCCA;

MtTT2like qPCR Forward primer:
                                 (SEQ ID NO: 17)
CGTCCATCCGTCAAACGCGG, MtTT2like qPCR Reverse primer:
                                 (SEQ ID NO: 18)
ACGGTGGAGGCGGAGGATGA;

MtANRqPCR Forward primer:
                                 (SEQ ID NO: 19)
GCAAAGCCACCCACTTGGGGTT, MtANRqPCR Reverse primer:
                                 (SEQ ID NO: 20)
TCAGCAAATTTCCACGCAGCCT;

MtTT2like qPCR Forward primer #2:
                                 (SEQ ID NO: 21)
ACGACGATGCATTTGCTGCACAC;

MttTT2like qPCR Reverse primer #2:
                                 (SEQ ID NO: 22)
GGCGGCGATTCCCACAGAGC;

MtPARqPCR Forward primer:
                                 (SEQ ID NO: 23)
AGCCAACATCATCATCATCATTGCCA, MtPARqPCRCR Rerse primer:
                                 (SEQ ID NO: 24)
AGGCTTTGGAGCTTCTGGTGCT.
```

Comparisons of transcript levels in seed at 20 DAP identified 49 genes that were differentially-expressed (transcript ratio <0.5 or >2; p-value <0.05) between par mutants (lines NF2466, NF3308 and NF4419) and their wild-type siblings. Of these, 38 genes exhibited lower- and 11 genes exhibited higher transcript levels in the mutants (Table 2). According to GeneBins ontology (Goffard and Weiller, 2007), 14 of the genes that were 'repressed' in the mutants encode enzymes involved in flavonoid biosynthesis. Some of these genes/enzymes are required for both PA and anthocyanin synthesis (e.g. chalcone synthase, CHS; flavonoid 3'-hydroxylase, F3H; and leucoanthocyanidin dioxygenase (LDOX; also termed ANS)), while others act downstream in metabolism and are specific to PA biosynthesis (e.g. anthocyanidin reductase ANR, glucosyltransferase UGT72L1). Genes that were more highly expressed in the mutants were mostly of unknown function (Table 2).

TABLE 2

List of probesets down- and up-regulated in par mutants by more than two-fold and also at a statistically significant level (p-value <5%). Probesets are found at *Medicago truncatula* Gene Expression Atlas ("MtGEA;" Benedito et al., 2008; He et al., 2009).

| Probesets | Target Description | Ave WT | SD WT | Ave par |
|---|---|---|---|---|
| Mtr.20567.1.S1_at | IMGAG\|1115.m00010 /FEA = mRNA /DEF = Type III polyketide synthase; Naringenin-chalcone synthase AC146683.9.91 50180 48876 mth2-179n10 Jan. 13, 2005 | 859.643182 | 428.177702 | 5.878338 |
| Mtr.36333.1.S1_at | BE248436 /FEA = mRNA /DEF = similar to UP\|Q84JJ4 (Q84JJ4) Flavonoid 3'-hydroxylase (Fragment), partial (21%) | 1671.23062 | 589.880834 | 45.80479 |
| Mtr.6517.1.S1_at | BQ147749 /FEA = mRNA /DEF = similar to UP\|Q84J65 (Q84J65) Gray pubescence flavonoid 3'-hydroxylase, partial (49%) | 233.108836 | 71.1217427 | 11.46001 |
| Mtr.49572.1.S1_s_at | IMGAG\|1104.m00016 /FEA = mRNA /DEF = Naringenin-chalcone synthase; Type III polyketide synthase AC146575.3.161 92557 91179 mth2-145m4 Jan. 13, 2005 | 598.355904 | 174.894912 | 29.87211 |

TABLE 2-continued

List of probesets down- and up-regulated in par mutants by more than two-fold and also at a statistically significant level (p-value <5%). Probesets are found at *Medicago truncatula* Gene Expression Atlas ("MtGEA;" Benedito et al., 2008; He et al., 2009).

| | | | | |
|---|---|---|---|---|
| Mtr.20187.1.S1_x_at | IMGAG\|1104.m00017 /FEA = mRNA /DEF = Naringenin-chalcone synthase; Type III polyketide synthase AC146575.3.171 96668 95373 mth2-145m4 Jan. 13, 2005 | 1463.82328 | 192.448074 | 80.56568 |
| Mtr.20187.1.S1_at | IMGAG\|1104.m00017 /FEA = mRNA /DEF = Naringenin-chalcone synthase; Type III polyketide synthase AC146575.3.171 96668 95373 mth2-145m4 Jan. 13, 2005 | 3779.97877 | 423.949372 | 220.1103 |
| Mtr.14017.1.S1_at | TC99980 /FEA = mRNA /DEF = weakly similar to UP\|LDOX_ARATH (Q96323) Leucoanthocyanidin dioxygenase (LDOX) (Leucocyanidin oxygenase) (Leucoanthocyanidin hydroxylase) (Anthocyanidin synthase) (ANS), partial (19%) | 320.922409 | 158.721654 | 20.08867 |
| Mtr.39897.1.S1_at | TC105988 /FEA = mRNA /DEF = similar to UP\|P93697 (P93697) CPRD12 protein, partial (61%) | 1916.82201 | 764.031111 | 152.5205 |
| Mtr.49572.1.S1_x_at | IMGAG\|1104.m00016 /FEA = mRNA /DEF = Naringenin-chalcone synthase; Type III polyketide synthase AC146575.3.161 92557 91179 mth2-145m4 Jan. 13, 2005 | 97.5854467 | 18.8400876 | 12.78775 |
| Mtr.21996.1.S1_x_at | 1578.m00031 /FEA = mRNA /DEF = AC124966.27 4823 6271 mth2-8i15 weakly similar to UP\|Q8S996 (Q8S996) Glucosyltransferase-13 (Fragment) | 492.816558 | 117.195381 | 73.31215 |
| Mtr.44985.1.S1_at | TC98546 /FEA = mRNA /DEF = UP\|Q84XT1 (Q84XT1) Anthocyanidin reductase, complete | 659.987412 | 268.830912 | 109.3382 |
| Mtr.50541.1.S1_at | IMGAG\|1054.m00009 /FEA = mRNA /DEF = Myb, DNA-binding; Homeodomain-like AC144645.17.81 55517 54273 mth2-11e15 Jan. 13, 2005 | 124.145527 | 46.9606818 | 24.41019 |
| Mtr.28714.1.S1_at | BI311259 /FEA = mRNA /DEF = homologue to PRF\|1609233A\|226868\|1609233A chalcone synthase 3. {*Sinapis alba*;}, partial (12%) | 47.8662293 | 19.0123022 | 10.27827 |
| Mtr.16432.1.S1_at | IMGAG\|824.m00011 /FEA = mRNA /DEF = Myb, DNA-binding; Homeodomain-like AC129092.13.101 59248 60901 mth2-17n16 Jan. 13, 2005 | 194.699929 | 80.1064012 | 44.75606 |
| Mtr.44170.1.S1_at | TC96829 /FEA = mRNA /DEF= | 51.9129817 | 20.5943212 | 12.56979 |
| Mtr.41031.1.S1_at | TC108579 /FEA = mRNA /DEF = homologue to PIR\|PQ0772\|PQ0772 4-coumarate-CoA ligase (clone GM4CL1B) - soybean (fragment) {*Glycine max*;}, partial (62%) | 652.108309 | 255.535998 | 158.1682 |
| Mtr.42595.1.S1_at | TC111920 /FEA = mRNA /DEF = similar to UP\|Q94EH4 (Q94EH4) At1g48100/F21D18_17, partial (52%) | 85.8797083 | 16.2812939 | 22.91909 |
| Mtr.9864.1.S1_at | TC104661 /FEA = mRNA /DEF = similar to PIR\|T51355\|T51355 membrane protein [imported] - *Arabidopsis thaliana* (fragment) {*Arabidopsis thaliana*;}, partial (37%) | 43.612151 | 10.5148258 | 13.76203 |
| Mtr.13370.1.S1_at | TC97820 /FEA = mRNA /DEF = similar to UP\|O24623 (O24623) Gibberellin 3 beta-hydroxylase, partial (55%) | 79.8549723 | 23.4285299 | 27.89866 |
| Mtr.10917.1.S1_at | TC108343 /FEA = mRNA /DEF = similar to UP\|C773_SOYBN (O48928) Cytochrome P450 77A3, partial (95%) | 199.850989 | 49.111823 | 73.35225 |
| Mtr.2632.1.S1_at | BI311277 /FEA = mRNA /DEF = homologue to UP\|Q8LJQ5 (Q8LJQ5) LEC1-like protein, partial (58%) | 1280.85869 | 362.827026 | 506.9417 |
| Mtr.38379.1.S1_at | TC102674 /FEA = mRNA /DEF = weakly similar to UP\|Q6GQH4 (Q6GQH4) Egr1 protein, partial (8%) | 43.109902 | 10.9364836 | 17.33879 |

TABLE 2-continued

List of probesets down- and up-regulated in par mutants by more than two-fold and also at a statistically
significant level (p-value <5%). Probesets are found at *Medicago truncatula* Gene Expression Atlas
("MtGEA;" Benedito et al., 2008; He et al., 2009).

| | | | | |
|---|---|---|---|---|
| Mtr.50478.1.S1_at | IMGAG\|968.m00002 /FEA = mRNA /DEF = Phenylalanine/histidine ammonia-lyase; L-Aspartase-like; Phenylalanine ammonia-lyase AC140028.21.21 6624 2477 mth2-7e24 Jan. 13, 2005 | 200.937703 | 46.7852944 | 81.43143 |
| Mtr.5901.1.S1_at | BG451575 /FEA = mRNA /DEF = similar to UP\|ST14_SOLTU (Q41495) STS14 protein precursor, partial (49%) | 536.655108 | 87.7948319 | 218.503 |
| Mtr.26465.1.S1_s_at | 1520.m00027 /FEA = mRNA /DEF = AC138199.22 70888 78437 mth2-15g10 similar to UP\|PEAM_SPIOL (Q9M571) Phosphoethanolamine N-methyltransferase (EC 2.1.1.103) | 10.399725 | 0.89274666 | 4.373235 |
| Mtr.38932.1.S1_at | TC103858 /FEA = mRNA /DEF = similar to UP\|MASY_SOYBN (P45458) Malate synthase, glyoxysomal (MS) (Fragment), partial (39%) | 215.131423 | 16.8692609 | 94.76488 |
| Mtr.10989.1.S1_at | TC108525 /FEA = mRNA /DEF= | 20.541302 | 3.52727699 | 9.278425 |
| Mtr.48911.1.S1_at | IMGAG\|754.m00021 /FEA = mRNA /DEF = Short-chain dehydrogenase/reductase SDR; Glucose/ribitol dehydrogenase AC123572.15.211 87481 89526 mth2-2b2 Jan. 13, 2005 | 49.8156177 | 6.93616061 | 22.8149 |
| Mtr.27388.1.S1_s_at | AW775333 /FEA = mRNA /DEF = UP\|Q8GTY4 (Q8GTY4) Rubisco activase (Fragment), partial (81%) | 120.199138 | 12.1398853 | 55.87101 |
| Mtr.35526.1.S1_at | TC105231 /FEA = mRNA /DEF= | 147.897155 | 46.015984 | 69.77271 |
| Mtr.37221.1.S1_at | TC100154 /FEA = mRNA /DEF = homologue to UP\|Q43437 (Q43437) Photosystem II type I chlorophyll a/b-binding protein precursor, complete | 489.390869 | 115.52534 | 233.2353 |
| Mtr.10393.1.S1_at | TC106621 /FEA = mRNA /DEF = similar to UP\|Q9SLR8 (Q9SLR8) Thiamin biosynthetic enzyme, partial (91%) | 1563.74757 | 459.862458 | 753.3561 |
| Mtr.37657.1.S1_at | TC101144 /FEA = mRNA /DEF = similar to UP\|Q96400 (Q96400) Nitrite transporter, partial (88%) | 143.541663 | 29.9639896 | 70.27863 |
| Msa.1297.1.S1_at | iMsa.1297 /TID = Msa.1297.1 /CNT = 1 /FEA = mRNA /TIER = ConsEnd /STK = 0 /NOTE = sequence(s) not in UniGene /DEF= | 1109.9202 | 59.2233123 | 543.7646 |
| Mtr.9046.1.S1_at | TC102211 /FEA = mRNA /DEF = similar to UP\|GST1_LYCES (P27057) GAST1 protein precursor, partial (60%) | 732.975163 | 157.254025 | 360.5397 |
| Mtr.12246.1.S1_at | TC94105 /FEA = mRNA /DEF = UP\|O24099 (O24099) MtN12 protein (Fragment), complete | 30.3397733 | 5.37213744 | 14.93328 |
| Mtr.12374.1.S1_at | TC94561 /FEA = mRNA /DEF = homologue to PIR\|S20941\|S20941 protochlorophyllide reductase precursor - garden pea {*Pisum sativum*;}, complete | 4453.53702 | 711.490929 | 2208.304 |
| Mtr.37215.1.S1_at | TC100145 /FEA = mRNA /DEF = homologue to UP\|Q43437 (Q43437) Photosystem II type I chlorophyll a/b-binding protein precursor, complete | 85.5805213 | 20.0459827 | 42.55927 |
| Mtr.25647.1.S1_at | 1444.m00049 /FEA = mRNA /DEF = AC146630.25 121131 117741 mth2-7f22 weakly similar to UP\|O64548 (O64548) YUP8H12R.38 protein | 68.1816447 | 16.1134736 | 137.2836 |
| Mtr.40882.1.S1_at | TC108249 /FEA = mRNA /DEF = weakly similar to UP\|Q8W033 (Q8W033) Aldehyde dehydrogenase, partial (84%) | 86.9470197 | 7.1879305 | 176.0712 |
| Mtr.44363.1.S1_at | TC97216 /FEA = mRNA /DEF = similar to UP\|Q93ZQ5 (Q93ZQ5) AT4g22990/F7H19_170, partial (29%) | 51.907178 | 12.684616 | 108.9426 |

TABLE 2-continued

List of probesets down- and up-regulated in par mutants by more than two-fold and also at a statistically significant level (p-value <5%). Probesets are found at *Medicago truncatula* Gene Expression Atlas ("MtGEA;" Benedito et al., 2008; He et al., 2009).

| | | | | |
|---|---|---|---|---|
| Mtr.43455.1.S1_at | TC95369 /FEA = mRNA /DEF = weakly similar to GB\|AAL15368.1\|16323268\|AY057738 At1g15670/F7H2_1 {*Arabidopsis thaliana*;}, partial (49%) | 59.199118 | 18.553866 | 135.8152 |
| Mtr.40913.1.S1_at | TC108317 /FEA = mRNA /DEF = similar to UP\|Q6CXP0 (Q6CXP0) *Kluyveromyces lactis* strain NRRL Y-1140 chromosome A of strain NRRL Y-1140 of *Kluyveromyces lactis*, partial (4%) | 54.0917987 | 14.8964758 | 129.4808 |
| Mtr.48521.1.S1_at | IMGAG\|1169.m00022 /FEA = mRNA /DEF = putative low-molecular-weight cysteine-rich protein lcr19 precursor, putative AC147407.10.221 75050 75673 mth2-159b14 Jan. 13, 2005 | 42.7850667 | 4.79186431 | 104.0712 |
| Mtr.38412.1.S1_at | TC102743 /FEA = mRNA /DEF = UP\|Q5WET6 (Q5WET6) Phosphate ABC transporter permease, partial (5%) | 62.7663617 | 8.53194602 | 171.3022 |
| Mtr.43887.1.S1_at | TC96246 /FEA = mRNA /DEF = similar to GB\|AAP88343.1\|32815917\|BT009709 At3g13310 {*Arabidopsis thaliana*;}, partial (31%) | 419.161484 | 112.701881 | 1167.374 |
| Mtr.39929.1.S1_at | TC106102 /FEA = mRNA /DEF = homologue to UP\|O24082 (O24082) 17 kD heat shock protein, partial (76%) | 43.2521373 | 7.45366017 | 144.1983 |
| Mtr.21943.1.S1_s_at | 1575.m00026 /FEA = mRNA /DEF = AC124216.19 211 2394 mth2-34o22 weakly similar to UP\|O48924 (O48924) CYP83D1p (Fragment) | 24.0987247 | 3.23843614 | 88.50047 |
| Mtr.21943.1.S1_x_at | 1575.m00026 /FEA = mRNA /DEF = AC124216.19 211 2394 mth2-34o22 weakly similar to UP\|O48924 (O48924) CYP83D1p (Fragment) | 54.040693 | 27.3305952 | 207.9964 |

| Probesets | SD par | Pts | Pta | Ratio(par/WT) |
|---|---|---|---|---|
| Mtr.20567.1.S1_at | 0.921726 | 0.025969 | 0 | 0.006838114 |
| Mtr.36333.1.S1_at | 38.48854 | 0.008888 | 0 | 0.027407824 |
| Mtr.6517.1.S1_at | 3.963385 | 0.005732 | 0 | 0.049161643 |
| Mtr.49572.1.S1_s_at | 8.198254 | 0.004916 | 0 | 0.04992365 |
| Mtr.20187.1.S1_x_at | 38.15873 | 0.000258 | 0 | 0.055037848 |
| Mtr.20187.1.S1_at | 100.2211 | 0.000145 | 0 | 0.058230557 |
| Mtr.14017.1.S1_at | 2.819671 | 0.030434 | 0 | 0.062596644 |
| Mtr.39897.1.S1_at | 94.02205 | 0.016543 | 1.015E−231 | 0.079569453 |
| Mtr.49572.1.S1_x_at | 3.465614 | 0.001556 | 0 | 0.131041565 |
| Mtr.21996.1.S1_x_at | 7.812866 | 0.00347 | 0 | 0.148761539 |
| Mtr.44985.1.S1_at | 86.77618 | 0.027882 | 4.2247E−28 | 0.165667143 |
| Mtr.50541.1.S1_at | 21.49587 | 0.028708 | 9.2613E−16 | 0.196625637 |
| Mtr.28714.1.S1_at | 3.599841 | 0.028186 | 4.163E−73 | 0.214729135 |
| Mtr.16432.1.S1_at | 9.913184 | 0.032357 | 2.766E−151 | 0.229871984 |
| Mtr.44170.1.S1_at | 4.820915 | 0.032225 | 2.3066E−45 | 0.242131973 |
| Mtr.41031.1.S1_at | 53.71319 | 0.030605 | 4.0683E−57 | 0.242548922 |
| Mtr.42595.1.S1_at | 10.58873 | 0.004944 | 7.1366E−25 | 0.266874288 |
| Mtr.9864.1.S1_at | 2.61025 | 0.008826 | 2.5807E−87 | 0.315554878 |
| Mtr.13370.1.S1_at | 17.10545 | 0.036143 | 1.4331E−07 | 0.349366589 |
| Mtr.10917.1.S1_at | 9.86689 | 0.011932 | 3.019E−109 | 0.367034687 |
| Mtr.2632.1.S1_at | 153.77 | 0.027237 | 2.8485E−18 | 0.395782719 |
| Mtr.38379.1.S1_at | 2.320878 | 0.01623 | 1.9724E−82 | 0.402199662 |
| Mtr.50478.1.S1_at | 37.24986 | 0.025789 | 2.7473E−08 | 0.405257109 |
| Mtr.5901.1.S1_at | 35.32962 | 0.004332 | 7.5638E−55 | 0.407157245 |
| Mtr.26465.1.S1_s_at | 0.212616 | 0.000341 | 0 | 0.420514517 |
| Mtr.38932.1.S1_at | 34.44285 | 0.005558 | 0 | 0.44049762 |
| Mtr.10989.1.S1_at | 2.38271 | 0.010161 | 2.6732E−16 | 0.451696067 |
| Mtr.48911.1.S1_at | 6.415001 | 0.007761 | 3.0952E−13 | 0.457986934 |
| Mtr.27388.1.S1_s_at | 18.17099 | 0.00699 | 0 | 0.464820358 |
| Mtr.35526.1.S1_at | 13.27917 | 0.04757 | 2.1964E−24 | 0.471765032 |
| Mtr.37221.1.S1_at | 88.71524 | 0.038178 | 5.7002E−07 | 0.476582784 |
| Mtr.10393.1.S1_at | 204.4556 | 0.049359 | 6.6375E−12 | 0.481763243 |
| Mtr.37657.1.S1_at | 16.2329 | 0.02041 | 5.4025E−15 | 0.489604419 |
| Msa.1297.1.S1_at | 92.8636 | 0.00088 | 0 | 0.489913204 |
| Mtr.9046.1.S1_at | 117.02 | 0.030189 | 3.5369E−08 | 0.491885269 |
| Mtr.12246.1.S1_at | 4.840689 | 0.021016 | 3.5356E−08 | 0.492201425 |
| Mtr.12374.1.S1_at | 448.7319 | 0.009858 | 4.4629E−18 | 0.495854053 |
| Mtr.37215.1.S1_at | 11.79179 | 0.032776 | 2.6288E−10 | 0.497300873 |

TABLE 2-continued

List of probesets down- and up-regulated in par mutants by more than two-fold and also at a statistically significant level (p-value <5%). Probesets are found at *Medicago truncatula* Gene Expression Atlas ("MtGEA;" Benedito et al., 2008; He et al., 2009).

| | | | | |
|---|---|---|---|---|
| Mtr.25647.1.S1_at | 18.84132 | 0.008475 | 1.104E−13 | 2.013497826 |
| Mtr.40882.1.S1_at | 36.82668 | 0.014683 | 2.615E−102 | 2.025039509 |
| Mtr.44363.1.S1_at | 7.173214 | 0.002471 | 0 | 2.098795732 |
| Mtr.43455.1.S1_at | 0 | 0.002022 | 0 | 2.294209468 |
| Mtr.40913.1.S1_at | 33.92323 | 0.024354 | 1.8567E−18 | 2.393723809 |
| Mtr.48521.1.S1_at | 19.671 | 0.006327 | 9.921E−109 | 2.43241952 |
| Mtr.38412.1.S1_at | 63.87284 | 0.043361 | 1.372E−107 | 2.729203697 |
| Mtr.43887.1.S1_at | 201.8901 | 0.004976 | 1.3369E−30 | 2.7850214 |
| Mtr.39929.1.S1_at | 60.96489 | 0.046549 | 1.11E−121 | 3.333900686 |
| Mtr.21943.1.S1_s_at | 27.47733 | 0.015711 | 5.414E−260 | 3.672413176 |
| Mtr.21943.1.S1_x_at | 27.87122 | 0.002402 | 0 | 3.848884118 |

Genes corresponding to 171 probe-sets were significantly altered (transcript ratio <0.5 or >2; p-value <0.05) in expression in *M. truncatula* hairy roots transformed with p35S::MtPAR compared to p35S:: GUS-transformed controls (Table 3). One hundred and fifteen of these exhibited higher transcript levels in p35S::MtPAR roots. Eleven of the 115 genes code for putative enzymes of flavonoid biosynthesis (e.g. CHS, F3H, and ANS).

TABLE 3

List of probesets down- and up-regulated in transformed hairy roots by more than two-fold and also at a statistically significant level (p-value <5%). Probesets are found at *Medicago truncatula* Gene Expression Atlas ("MtGEA;" Benedito et al., 2008; He et al., 2009).

| Probesets | Transcript ID(Array Design) | Target Description | Representative Public ID | Ave OE-GUS | SD OE-GUS | Ave OE-PAR | SD OE-PAR | PTS | PTA | Ratio (OE-PAR:OE-GUS) |
|---|---|---|---|---|---|---|---|---|---|---|
| Mtr.50541.1.S1_at | Mtr.50541.1 | IMGAG|1054.m00009 /FEA = mRNA /DEF = Myb, DNA-binding; Homeodomain-like AC144645.17.81 55517 54273 mth2-11e15 Jan. 13, 2005 | IMGAG|1054.m00009 | 9.982159 | 2.410535 | 1045.049 | 170.3748 | 0.000461 | 0 | 104.6917 |
| Mtr.31745.1.S1_at | Mtr.31745.1 | AL378024 /FEA = mRNA /DEF = UP|Q635K2 (Q635K2) Possible acetoin transport permease, partial (2%) | AL378024 | 5.652491 | 1.040688 | 496.1846 | 87.22061 | 0.000622 | 0 | 87.78158 |
| Mtr.15215.1.S1_at | Mtr.15215.1 | IMGAG|732.m00014 /FEA = mRNA /DEF = unnamed protein product; contains similarity to unknown protein gb|AAB70446.1 gene_id: K24M7.6 AC121244.13.131 60816 57747 mth2-31b9 Jan. 13, 2005 | IMGAG|732.m00014 | 9.69528 | 1.563699 | 810.6132 | 185.9664 | 0.001726 | 0 | 83.60905 |
| Mtr.9657.1.S1_at | Mtr.9657.1 | TC103993 /FEA = mRNA /DEF = similar to UP|O04197 (O04197) Coronatine-insensitive 1 (COI1), AtFBL2 (At2g39940/T28M21.10) (LRR-containing F-box protein), partial (53%) | TC103993 | 7.059164 | 0.754961 | 170.0771 | 13.77901 | 3.37E-05 | 0 | 24.09309 |
| Mtr.3831.1.S1_at | Mtr.3831.1 | BI265054 /FEA = mRNA /DEF = | BI265054 | 21.38637 | 6.771167 | 238.3361 | 100.6331 | 0.020375 | 0 | 11.1443 |
| Mtr.39028.1.S1_at | Mtr.39028.1 | TC104048 /FEA = mRNA /DEF = similar to GB|AAS09999.1|41618996|AY519529 MYB transcription factor {*Arabidopsis thaliana*;}, partial (43%) | TC104048 | 14.71274 | 1.652201 | 152.5719 | 19.95448 | 0.000283 | 0 | 10.37005 |
| Mtr.42658.1.S1_at | Mtr.42658.1 | TC112097 /FEA = mRNA /DEF = similar to UP|Q8K0R3 (Q8K0R3) Ski protein (Fragment), partial (6%) | TC112097 | 18.72994 | 4.976025 | 153.4187 | 36.96635 | 0.003333 | 0 | 8.191094 |
| Mtr.47022.1.S1_s_at | Mtr.47022.1 | 1705.m00036 /FEA = mRNA /DEF = AC148359.19 17939 18394 mth2-22k1 weakly similar to TAIR|gene: 2181071-GOpep. 168412.m00083 expressed protein wound-inducible protein wun1 protein - *Solanum* | 1705.m00036 | 29.80183 | 3.491729 | 175.7989 | 71.83741 | 0.02454 | 0 | 5.898927 |
| Mtr.17550.1.S1_at | Mtr.17550.1 | IMGAG|1003.m00011 /FEA = mRNA /DEF = Plant lipid transfer protein/Par allergen; Plant lipid transfer/seed storage/trypsin-alpha amylase inhibitor AC141322.24.111 47012 45856 mth2-8e1 Jan. 13, 2005 | IMGAG|1003.m00011 | 61.13021 | 21.97928 | 350.3567 | 162.9343 | 0.038141 | 5.5E-115 | 5.731319 |
| Mtr.2667.1.S1_at | Mtr.2667.1 | BM779752 /FEA = mRNA /DEF = | BM779752 | 17.98985 | 5.494132 | 98.90028 | 18.50033 | 0.00191 | 1.6E-143 | 5.49561 |
| Mtr.2174.1.S1_at | Mtr.2174.1 | BG448288 /FEA = mRNA /DEF = | BG448288 | 32.79162 | 8.562886 | 177.3127 | 39.25415 | 0.00338 | 7.4E-188 | 5.407256 |

TABLE 3-continued

List of probesets down- and up-regulated in transformed hairy roots by more than two-fold and also at a statistically significant level (p-value <5%). Probesets are found at *Medicago truncatula* Gene Expression Atlas ("MtGEA;" Benedito et al. 2008; He et al. 2009).

| Probesets | Transcript ID (Array Design) | Target Description | Representative Public ID | Ave OE-GUS | SD OE-GUS | Ave OE-PAR | SD OE-PAR | PTS | PTA | Ratio (OE-PAR:OE-GUS) |
|---|---|---|---|---|---|---|---|---|---|---|
| Mtr.40380.1.S1_at | Mtr.40380.1 | TC10167 /FEA = mRNA /DEF = weakly similar to UP|Q9SB32 (Q9SB32) SRG1-like protein (At4g25310), partial (44%) | TC10167 | 55.38911 | 51.94652 | 293.7718 | 47.75451 | 0.004255 | 0 | 5.303782 |
| Mtr.1872.1.S1_at | Mtr.1872.1 | BE239373 /FEA = mRNA /DEF = weakly similar to GB|CAA66109.3|4842629|CANST2PRO specific tissue protein 2 {*Cicer arietinum*;}, partial (27%) | BE239373 | 85.49441 | 51.09398 | 449.4508 | 141.4529 | 0.01379 | 5.66E-35 | 5.257078 |
| Mtr.31025.1.S1_at | Mtr.31025.1 | TC96845 /FEA = mRNA /DEF= | TC96845 | 102.841 | 112.6199 | 507.1613 | 20.85026 | 0.003622 | 0 | 4.931511 |
| Mtr.20567.1.S1_at | Mtr.20567.1 | IMGAG|1115.m00010 /FEA = mRNA /DEF = Type III polyketide synthase; Naringenin-chalcone synthase AC146683.9.91 50180 48876 mth2-179n10 Jan. 13, 2005 | IMGAG|1115.m00010 | 247.7764 | 32.64647 | 1164.871 | 418.3995 | 0.019352 | 0 | 4.701298 |
| Mtr.42945.1.S1_x_at | Mtr.42945.1 | TC94166 /FEA = mRNA /DEF= iMsa.3084 /TID = Msa.3084.1 /CNT = 1 /FEA = mRNA /TIER = ConsEnd /STK = 0 /NOTE = sequence(s) not in UniGene /DEF= | TC94166 | 21.43954 | 12.09383 | 98.20516 | 9.756303 | 0.001024 | 0 | 4.580564 |
| Msa.3084.1.S1_at | Msa.3084.1 | | TC87 | 24.4536 | 3.089405 | 103.2631 | 35.34588 | 0.018346 | 0 | 4.222819 |
| Mtr.43960.1.S1_at | Mtr.43960.1 | TC96409 /FEA = mRNA /DEF = weakly similar to UP|Q6TDU2 (Q6TDU2) Coronatine-insensitive 1, partial (31%) | TC96409 | 8.572815 | 1.205952 | 35.28415 | 8.621999 | 0.006029 | 0 | 4.115818 |
| Mtr.33715.1.S1_at | Mtr.33715.1 | BI265542 /FEA = mRNA /DEF= | BI265542 | 10.36655 | 1.75463 | 41.11893 | 18.60234 | 0.046364 | 2.1E-202 | 3.966501 |
| Mtr.25016.1.S1_at | Mtr.25016.1 | 1785.m00050 /FEA = mRNA /DEF = AC155890.1 50797 51458 mth2-49p3 | 1785.m00050 | 35.53711 | 3.06294 | 140.4745 | 15.86264 | 0.000356 | 0 | 3.952895 |
| Mtr.14017.1.S1_at | Mtr.14017.1 | TC99980 /FEA = mRNA /DEF = weakly similar to UP|LDOX_ARATH (Q96323) Leucoanthocyanidin dioxygenase (LDOX) (Leucocyanidin oxygenase) (Leucoanthocyanidin hydroxylase) (Anthocyanidin synthase) (ANS), partial (19%) | TC99980 | 17.83044 | 0.618886 | 68.77901 | 9.081704 | 0.000634 | 0 | 3.857393 |
| Mtr.38212.1.S1_at | Mtr.38212.1 | TC102299 /FEA = mRNA /DEF = similar to UP|SOC1_ARATH (O64645) SUPPRESSOR OF CONSTANS OVEREXPRESSION 1 protein (Agamous-like MADS box protein AGL20), partial (84%) | TC102299 | 196.2747 | 110.7566 | 738.9281 | 77.19826 | 0.002237 | 0 | 3.764765 |
| Mtr.46868.1.S1_s_at | Mtr.46868.1 | 1721.m00028 /FEA = mRNA /DEF = AC149580.15 36711 40336 mth2-123f14 similar to UP|Q43817 (Q43817) Lipoxygenase (EC 1.13.11.12) | 1721.m00028 | 38.47225 | 31.34234 | 138.5788 | 39.3427 | 0.026125 | 3.16E-08 | 3.602047 |

TABLE 3-continued

List of probesets down- and up-regulated in transformed hairy roots by more than two-fold and also at a statistically significant level (p-value <5%). Probesets are found at Medicago truncatula Gene Expression Atlas ("MtGEA;" Benedito et al. 2008; He et al. 2009).

| Probesets | Transcript ID (Array Design) | Target Description | Representative Public ID | Ave OE-GUS | SD OE-GUS | Ave OE-PAR | SD OE-PAR | PTS | PTA | Ratio (OE-PAR:OE-GUS) |
|---|---|---|---|---|---|---|---|---|---|---|
| Mtr.10725.1.S1_at | Mtr.10725.1 | TC107714 /FEA = mRNA /DEF = similar to UP|Q9ZRV5 (Q9ZRV5) Basic blue copper protein, partial (98%) | TC107714 | 848.5854 | 50.51791 | 2933.289 | 161.1705 | 2.83E-05 | 0 | 3.456681 |
| Mtr.46870.1.S1_at | Mtr.46870.1 | 1721.m00025 /FEA = mRNA /DEF = AC149580.15 18018 21534 mth2-123f14 similar to UP|LOX1_LENCU (P38414) Lipoxygenase (EC 1.13.11.12) | 1721.m00025 | 24.82831 | 18.46775 | 84.59721 | 18.02103 | 0.01597 | 9.22E-09 | 3.407288 |
| Mtr.23228.1.S1_at | Mtr.23228.1 | 1661.m00045 /FEA = mRNA /DEF = AC145109.33 24251 23742 mth2-25f20 | 1661.m00045 | 481.0663 | 167.7122 | 1608.402 | 289.3998 | 0.004292 | 2.5E-31 | 3.343411 |
| Mtr.10812.1.S1_at | Mtr.10812.1 | TC107993 /FEA = mRNA /DEF = similar to UP|C7DA_SOYBN (O48923) Cytochrome P450 71D10, partial (71%) | TC107993 | 35.46236 | 27.08208 | 116.591 | 17.66899 | 0.0122 | 1.78E-15 | 3.287739 |
| Mtr.29429.1.S1_at | Mtr.29429.1 | CX532222 /FEA = mRNA /DEF = | CX532222 | 22.21847 | 2.858976 | 72.88519 | 6.525392 | 0.00025 | 0 | 3.280387 |
| Mtr.31339.1.S1_at | Mtr.31339.1 | AJ504073 /FEA = mRNA /DEF = similar to UP|Q801G7 (Q801G7) Ribosomal protein S3 (Fragment), partial (33%) | AJ504073 | 8.439299 | 1.466162 | 26.49642 | 3.058862 | 0.000769 | 0 | 3.139647 |
| Mtr.43282.1.S1_at | Mtr.43282.1 | TC94971 /FEA = mRNA /DEF = similar to UP|Q84KK6 (Q84KK6) S-adenosyl-L-methionine: 2,7,4'-trihydroxyisoflavanone 4'-O-methyltransferase, partial (97%) | TC94971 | 142.4577 | 48.42814 | 445.1406 | 64.56671 | 0.002897 | 2.6E-27 | 3.124721 |
| Mtr.37050.1.S1_at | Mtr.37050.1 | TC111252 /FEA = mRNA /DEF = UP|Q8J8G6 (Q8J8G6) Envelope glycoprotein (Fragment), partial (6%) | TC111252 | 42.01327 | 22.34994 | 129.683 | 25.65002 | 0.011132 | 1.09E-11 | 3.086716 |
| Mtr.38836.1.S1_at | Mtr.38836.1 | TC103638 /FEA = mRNA /DEF = weakly similar to UP|Q7XZC4 (Q7XZC4) Albumin 1 precursor, partial (38%) | TC103638 | 52.2156 | 42.01571 | 159.3873 | 42.96095 | 0.036607 | 9.96E-06 | 3.052485 |
| Mtr.16385.1.S1_s_at | Mtr.16385.1 | IMGAG|868.m00028 /FEA = mRNA /DEF = TIR AC135396.30.281 94888 94343 mth2-33o18 Jan. 13, 2005 | IMGAG|868.m00028 | 10.64898 | 1.522778 | 32.19086 | 5.725062 | 0.003248 | 1.4E-132 | 3.022904 |
| Mtr.33192.1.S1_at | Mtr.33192.1 | BF645922 /FEA = mRNA /DEF = weakly similar to UP|Q6SQJ0 (Q6SQJ0) NBS-LRR type disease resistance protein Hom-F, partial (2%) | BF645922 | 20.28828 | 10.87565 | 60.92976 | 7.18335 | 0.005689 | 0 | 3.0032 |
| Mtr.1157.1.S1_s_at | Mtr.1157.1 | 1544.m00032 /FEA = mRNA /DEF = AC149039.2 10370 11266 mth2-4g23 weakly similar to UP|Q6WAY3 (Q6WAY3) Gag/pol polyprotein | 1544.m00032 | 213.1824 | 87.58313 | 636.2443 | 10.6119 | 0.001148 | 0 | 2.984506 |
| Mtr.17967.1.S1_x_at | Mtr.17967.1 | IMGAG|930.m00018 /FEA = mRNA /DEF = protein T2E6.4 [imported] - Arabidopsis thaliana-related AC138015.24.171 100595 100984 mth2-34m6 Jan. 13, 2005 | IMGAG|930.m00018 | 20.25361 | 0.991312 | 59.70946 | 5.97694 | 0.000352 | 0 | 2.948089 |

TABLE 3-continued

List of probesets down- and up-regulated in transformed hairy roots by more than two-fold and also at a statistically significant level (p-value <5%). Probesets are found at *Medicago truncatula* Gene Expression Atlas ("MtGEA;" Benedito et al. 2008; He et al. 2009).

| Probesets | Transcript ID (Array Design) | Representative Public ID | Target Description | Ave OE-GUS | SD OE-GUS | Ave OE-PAR | SD OE-PAR | PTS | PTA | Ratio (OE-PAR:OE-GUS) |
|---|---|---|---|---|---|---|---|---|---|---|
| Msa.3055.1.S1_at | Msa.3055 | TC60 | iMsa.3055 /TID = Msa.3055.1 /CNT = 1 /FEA = mRNA /TIER = ConsEnd /STK = 0 /NOTE = sequence(s) not in UniGene /DEF= | 18.64459 | 13.70837 | 54.52178 | 17.48199 | 0.048953 | 5.81E-06 | 2.924268 |
| Mtr.8651.1.S1_at | Mtr.8651.1 | TC100921 | TC100921 /FEA = mRNA /DEF = homologue to UP|Q945Q7 (Q945Q7) Dehydrin-like protein, partial (72%) | 12.25328 | 3.563077 | 35.43201 | 13.17635 | 0.042337 | 1.9E-29 | 2.891635 |
| Mtr.148.1.S1_s_at | Mtr.148.1 | 1785.m00048 | 1785.m00048 /FEA = mRNA /DEF = AC155890.1 47822 48796 mth2-49p3 | 100.0611 | 28.76711 | 288.2107 | 25.54402 | 0.001064 | 0 | 2.880346 |
| Mtr.13746.1.S1_at | Mtr.13746.1 | TC99043 | TC99043 /FEA = mRNA /DEF = weakly similar to UP|Q9FI39 (Q9FI39) Cytochrome P450, partial (25%) | 50.91619 | 7.994512 | 146.3706 | 42.7455 | 0.019072 | 5.17E-95 | 2.874736 |
| Mtr.40156.1.S1_at | Mtr.40156.1 | TC106633 | TC106633 /FEA = mRNA /DEF = similar to UP|Q8W2E3 (Q8W2E3) 3-hydroxy-3-methylglutaryl coenzyme A, partial (83%) | 5.88781 | 1.253098 | 16.89492 | 2.715512 | 0.003106 | 2.85E-52 | 2.869474 |
| Mtr.4415.1.S1_s_at | Mtr.4415.1 | AJ501932 | AJ501932 /FEA = mRNA /DEF = weakly similar to UP|Q43373 (Q43373) Galactose-binding lectin precursor, partial (19%) | 691.9708 | 439.3457 | 1955.44 | 329.3917 | 0.016328 | 3.06E-11 | 2.8259 |
| Mtr.11000.1.S1_at | Mtr.11000.1 | TC108561 | TC108561 /FEA = mRNA /DEF= | 14.38511 | 1.402579 | 40.35665 | 12.81938 | 0.025163 | 1.1E-225 | 2.805447 |
| Mtr.12285.1.S1_at | Mtr.12285.1 | TC94253 | TC94253 /FEA = mRNA /DEF= | 416.0914 | 384.7539 | 1128.625 | 136.4191 | 0.03904 | 0 | 2.712445 |
| Mtr.48045.1.S1_at | Mtr.48045.1 | 1601.m00057 | 1601.m00057 /FEA = mRNA /DEF = AC134824.27 103986 104615 mth2-14a2 | 168.9576 | 22.01792 | 453.356 | 141.1259 | 0.026085 | 7.3E-111 | 2.683253 |
| Mtr.22080.1.S1_at | Mtr.22080.1 | 1582.m00056 | 1582.m00056 /FEA = mRNA /DEF = AC127018.22 115376 121759 mth2-8a13 | 5.811889 | 0.238395 | 15.34872 | 5.194527 | 0.033645 | 0 | 2.640918 |
| Mtr.6517.1.S1_at | Mtr.6517.1 | BQ147749 | BQ147749 /FEA = mRNA /DEF = similar to UP|Q84J65 (Q84J65) Gray pubescence flavonoid 3'-hydroxylase, partial (49%) | 199.134 | 68.14577 | 525.2062 | 26.42525 | 0.00151 | 0 | 2.637451 |
| Mtr.36073.1.S1_s_at | Mtr.36073.1 | AJ845987 | AJ845987 /FEA = mRNA /DEF = similar to GB|AAA80183.1|606720|RPU12784 lectin {*Robinia pseudoacacia*;}, partial (11%) | 2384.764 | 1247.153 | 6282.824 | 506.7705 | 0.007409 | 0 | 2.634569 |
| Mtr.5990.1.S1_s_at | Mtr.5990.1 | BG455728 | BG455728 /FEA = mRNA /DEF= | 13.1366 | 3.485436 | 34.51418 | 12.70297 | 0.048271 | 2.32E-26 | 2.62733 |
| Mtr.40319.1.S1_at | Mtr.40319.1 | TC107032 | TC107032 /FEA = mRNA /DEF = weakly similar to UP|Q9ZWP4 (Q9ZWP4) Lectin-related polypeptide, partial (49%) | 2514.163 | 1294.344 | 6595.446 | 267.2237 | 0.005891 | 0 | 2.623317 |
| Mtr.31903.1.S1_at | Mtr.31903.1 | AL385004 | AL385004 /FEA = mRNA /DEF = similar to UP|STEL_RHUVE (P00302) Stellacyanin, partial (14%) | 329.2612 | 76.9095 | 844.1129 | 62.52478 | 0.000845 | 0 | 2.563657 |
| Mtr.31215.1.S1_s_at | Mtr.31215.1 | AJ499431 | AJ499431 /FEA = mRNA /DEF= | 81.09492 | 37.10519 | 206.5585 | 52.22605 | 0.027479 | 4.73E-09 | 2.54712 |

TABLE 3-continued

List of probesets down- and up-regulated in transformed hairy roots by more than two-fold and also at a statistically significant level (p-value <5%). Probesets are found at *Medicago truncatula* Gene Expression Atlas ("MtGEA;" Benedito et al., 2008; He et al., 2009).

| Probesets | Transcript ID(Array Design) | Target Description | Representative Public ID | Ave OE-GUS | SD OE-GUS | Ave OE-PAR | SD OE-PAR | PTS | PTA | Ratio (OE-PAR:OE-GUS) |
|---|---|---|---|---|---|---|---|---|---|---|
| Mtr.12742.1.S1_at | Mtr.12742.1 | TC95807 /FEA = mRNA /DEF = similar to UP|O49134 (O49134) GAST-like gene product, partial (73%) | TC95807 | 13.3915 | 2.590072 | 33.85925 | 12.18706 | 0.046613 | 1.21E-42 | 2.528414 |
| Mtr.18705.1.S1_at | Mtr.18705.1 | IMGAG|960.m00016 /FEA = mRNA /DEF = Peptidase C1A, papain; Peptidase, eukaryotic cysteine peptidase active site AC139746.15.151 101606 103039 mth2-17b20 Jan. 13, 2005 | IMGAG|960.m00016 | 102.9695 | 49.4787 | 258.0454 | 47.81252 | 0.017486 | 1.93E-08 | 2.506039 |
| Mtr.17982.1.S1_s_at | Mtr.17982.1 | IMGAG|932.m00012 /FEA = mRNA /DEF = hypothetical protein AC138017.15.111 51242 50808 mth2-6i3 Jan. 13, 2005 | IMGAG|932.m00012 | 5.95394 | 0.965889 | 14.90417 | 3.109012 | 0.008894 | 5.76E-58 | 2.503244 |
| Mtr.51818.1.S1_at | Mtr.51818.1 | IMGAG|896.m00006 /FEA = mRNA /DEF = predicted protein AC136840.24.51 30231 32005 mth2-33n3 Jan. 13, 2005 | IMGAG|896.m000006 | 113.8143 | 38.82412 | 281.0649 | 78.87617 | 0.03007 | 8.55E-14 | 2.469505 |
| Mtr.44634.1.S1_at | Mtr.44634.1 | TC97763 /FEA = mRNA /DEF = weakly similar to UP|Q6NLR7 (Q6NLR7) At5g04070, partial (53%) | TC97763 | 36.4022 | 17.80958 | 89.61022 | 20.25625 | 0.026858 | 2.28E-07 | 2.46167 |
| Mtr.9765.1.S1_at Mtr.17787.1.S1_at | Mtr.9765.1 Mtr.17787.1 | TC104312 /FEA = mRNA /DEF= IMGAG|1015.m00001 /FEA = mRNA /DEF = Isopenicillin N synthase; 2OG-Fe(II) oxygenase AC142498.21.11 7699 4521 mth2-24a18 Jan. 13, 2005 | TC104312 IMGAG|1015.m00001 | 81.45997 10.06593 | 41.25091 2.903876 | 200.0031 24.64216 | 34.49291 1.36213 | 0.018804 0.001408 | 2.64E-09 0 | 2.455232 2.448075 |
| Mtr.37882.1.S1_at | Mtr.37882.1 | TC101626 /FEA = mRNA /DEF = similar to UP|Q687E1 (Q687E1) Nucleotide pyrophosphatase/phosphodiesterase (Fragment), complete | TC101626 | 310.6463 | 198.6411 | 746.3512 | 37.6148 | 0.020248 | 0 | 2.402575 |
| Mtr.4815.1.S1_at Mtr.15436.1.S1_at | Mtr.4815.1 Mtr.15436.1 | AL385005 /FEA = mRNA /DEF= IMGAG|786.m00019 /FEA = mRNA /DEF = 2OG-Fe(II) oxygenase; Immunoglobulin/major histocompatibility complex AC125478.13.191 98375 97104 mth2-31l19 Jan. 13, 2005 | AL385005 IMGAG|786.m00019 | 911.7991 254.5841 | 200.3234 98.97065 | 2188.037 600.6536 | 193.7633 30.63402 | 0.001368 0.004435 | 0 0 | 2.399692 2.359352 |
| Mtr.25672.1.S1_a_at | Mtr.25672.1 | 1446.m00048 /FEA = mRNA /DEF = AC146752.23 87430 86695 mth2-62d4 | 1446.m00048 | 113.0598 | 26.58139 | 266.0491 | 13.32507 | 0.000876 | 0 | 2.353172 |
| Mtr.43296.1.S1_at Mtr.32965.1.S1_at | Mtr.43296.1 Mtr.32965.1 | TC95005 /FEA = mRNA /DEF= BF635325 /FEA = mRNA /DEF = similar to UP|Q9ZSP7 (Q9ZSP7) Cytochrome b5 DIF-F, partial (36%) | TC95005 BF635325 | 13.34978 181.4723 | 7.401407 36.40511 | 31.26966 422.1875 | 4.316036 96.95071 | 0.022306 0.015786 | 6.41E-13 2.28E-30 | 2.342335 2.326457 |
| Mtr.41019.1.S1_at | Mtr.41019.1 | TC108557 /FEA = mRNA /DEF = similar to UP|Q39449 (Q39449) Specific tissue protein 1, partial (93%) | TC108557 | 422.5297 | 178.6819 | 981.0658 | 109.6544 | 0.009922 | 0 | 2.321886 |

TABLE 3-continued

List of probesets down- and up-regulated in transformed hairy roots by more than two-fold and also at a statistically significant level (p-value <5%). Probesets are found at Medicago truncatula Gene Expression Atlas ("MtGEA;" Benedito et al. 2008; He et al., 2009).

| Probesets | Transcript ID(Array Design) | Target Description | Representative Public ID | Ave OE-GUS | SD OE-GUS | Ave OE-PAR | SD OE-PAR | PTS | PTA | Ratio (OE-PAR:OE-GUS) |
|---|---|---|---|---|---|---|---|---|---|---|
| Mtr.48723.1.S1_at | Mtr.48723.1 | IMGAGI1156.m00003 /FEA = mRNA /DEF = NPH3; BTB/POZ AC147002.20.21 21589 19459 mth2-151m16 Jan. 13, 2005 | IMGAGI1156.m00003 | 114.5791 | 43.79727 | 265.6709 | 43.83067 | 0.01344 | 2.3E-09 | 2.318669 |
| Mtr.9894.1.S1_at | Mtr.9894.1 | TC104797 /FEA = mRNA /DEF = weakly similar to UP (Q9LQ75 (Q9LQ75) T1N6.22 protein, partial (48%) | TC104797 | 382.3435 | 89.5521 | 868.8384 | 157.6059 | 0.009672 | 4.99E-21 | 2.272403 |
| Mtr.3133.1.S1_at | Mtr.3133.1 | CX525345 /FEA = mRNA /DEF = | CX525345 | 55.87685 | 23.32709 | 126.4847 | 15.5516 | 0.012042 | 3.77E-15 | 2.263634 |
| Mtr.10630.1.S1_at | Mtr.10630.1 | TC107430 /FEA = mRNA /DEF = weakly similar to UP NLT2_PRUAR (P82353) Nonspecific lipid-transfer protein 2 (LTP 2), partial (97%) | TC107430 | 336.2662 | 105.3783 | 761.1442 | 59.20414 | 0.00368 | 0 | 2.263517 |
| Mtr.47758.1.S1_at | Mtr.47758.1 | 1631.m00034 /FEA = mRNA /DEF = AC138465.20 10086 8601 mth2-23h19 weakly similar to TAIR gene: 3437446-GOpep. 168409. m02443 bHLH protein family contains Pfam profile: PF00010 | 1631.m00034 | 46.18555 | 10.93704 | 104.5183 | 8.215752 | 0.001791 | 0 | 2.26301 |
| Mtr.29531.1.S1_at | Mtr.29531.1 | TC105266 /FEA = mRNA /DEF = | TC105266 | 65.9136 | 32.72179 | 148.0582 | 11.8568 | 0.014999 | 0 | 2.246247 |
| Mtr.14428.1.S1_x_at | Mtr.14428.1 | IMGAGI1115.m00011 /FEA = mRNA /DEF = Naringenin-chalcone synthase; Type III polyketide synthase AC146683.9.101 54170 52902 mth2-179n10 Jan. 13, 2005 | IMGAGI1115.m00011 | 54.98663 | 6.632739 | 122.9121 | 24.1427 | 0.009315 | 2.14E-70 | 2.235309 |
| Mtr.28737.1.S1_at | Mtr.28737.1 | BI312112 /FEA = mRNA /DEF = similar to UP Q8LJS8 (Q8LJS8) Homeodomain protein GhHOX1, partial (27%) | BI312112 | 174.1705 | 52.26805 | 385.1184 | 60.70735 | 0.010331 | 2.74E-12 | 2.211157 |
| Mtr.8790.1.S1_at | Mtr.8790.1 | TC101400 /FEA = mRNA /DEF = similar to UP Q6A151 (Q6A151) Peripheral-type benzodiazepine receptor, partial (25%) | TC101400 | 128.399 | 29.50636 | 283.73 | 22.6213 | 0.001935 | 0 | 2.209753 |
| Mtr.16601.1.S1_at | Mtr.16601.1 | IMGAGI831.m00012 /FEA = mRNA /DEF = Copper/Zinc superoxide dismutase AC130801.16.121 78670 77054 mth2-12p19 Jan. 13, 2005 | IMGAGI831.m00012 | 3596.316 | 251.4687 | 7918.753 | 746.7478 | 0.000685 | 0 | 2.201907 |
| Mtr.14760.1.S1_at | Mtr.14760.1 | IMGAGI762.m00015 /FEA = mRNA /DEF = Basic helix-loop-helix dimerisation region bHLH; Helix-loop-helix DNA-binding AC124214.8.141 73702 74845 mth2-36a23 Jan. 13, 2005 | IMGAGI762.m00015 | 73.3436 | 36.87561 | 161.3223 | 30.27665 | 0.033096 | 4.83E-07 | 2.199542 |
| Mtr.11011.1.S1_at | Mtr.11011.1 | TC108588 /FEA = mRNA /DEF = | TC108588 | 64.67045 | 12.32351 | 141.6272 | 17.2181 | 0.003254 | 2.89E-27 | 2.189983 |
| Mtr.20511.1.S1_s_at | Mtr.20511.1 | IMGAGI1220.m00020 /FEA = mRNA /DEF = hypothetical protein AC148758.19.191 94204 93893 mth2-50I17 Jan. 13, 2005 | IMGAGI1220.m00020 | 18.52573 | 5.592439 | 40.50186 | 3.917321 | 0.005075 | 0 | 2.186248 |
| Mtr.35669.1.S1_at | Mtr.35669.1 | TC110723 /FEA = mRNA /DEF = | TC110723 | 14.0884 | 7.023 | 30.73013 | 4.783246 | 0.027474 | 1.68E-09 | 2.181236 |

TABLE 3-continued

List of probesets down- and up-regulated in transformed hairy roots by more than two-fold and also at a statistically significant level (p-value <5%). Probesets are found at *Medicago truncatula* Gene Expression Atlas ("MtGEA;" Benedito et al. 2008; He et al. 2009).

| Probesets | Transcript ID(Array Design) | Target Description | Representative Public ID | Ave OE-GUS | SD OE-GUS | Ave OE-PAR | SD OE-PAR | PTS | PTA | Ratio (OE-PAR:OE-GUS) |
|---|---|---|---|---|---|---|---|---|---|---|
| Mtr.46188.1.S1_x_at | Mtr.46188.1 | IMGAG\|1140.m00023 /FEA = mRNA /DEF = hypothetical protein AC146793.7.221 111595 111440 mth2-10p9 Jan. 13, 2005 | IMGAG\|1140.m00023 | 10.61773 | 2.063498 | 23.15905 | 1.747313 | 0.001303 | 0 | 2.181168 |
| Mtr.38138.1.S1_at | Mtr.38138.1 | TC102170 /FEA = mRNA /DEF = weakly similar to UP\|Q9LH70 (Q9LH70) Gb\|AAD22996.1, partial (66%) | TC102170 | 23.32823 | 3.339804 | 50.80832 | 11.62925 | 0.017048 | 4.39E-46 | 2.177976 |
| Mtr.18535.1.S1_at | Mtr.18535.1 | IMGAG\|1954.m00017 /FEA = mRNA /DEF = conserved hypothetical protein AC139601.8.171 104858 102948 mth2-8h11 Jan. 13, 2005 | IMGAG\|1954.m00017 | 17.22274 | 3.896279 | 37.29194 | 8.072006 | 0.017869 | 4.6E-19 | 2.165274 |
| Mtr.43089.1.S1_at | Mtr.43089.1 | TC94508 /FEA = mRNA /DEF = similar to UP\|Q9FDY1 (Q9FDY1) Seed maturation protein LEA 4, partial (45%) | TC94508 | 472.5886 | 230.4404 | 1020.365 | 199.9903 | 0.035889 | 2.09E-06 | 2.159098 |
| Msa.1900.1.S1_at | Msa.1900.1 | iMsa.1900 /TID = Msa.1900.1 /CNT = 1 /FEA = mRNA /TIER = ConsEnd /STK = 0 /NOTE = sequence(s) not in UniGene /DEF= | TC336 | 2557.748 | 91.76779 | 5511.223 | 289.7219 | 7.3E-05 | 0 | 2.154717 |
| Mtr.35816.1.S1_at | Mtr.35816.1 | TC95830 /FEA = mRNA /DEF = homologue to UP\|MCT1_HUMAN (P23946) Chymase precursor (Mast cell protease I), partial (6%) | TC95830 | 1746.035 | 591.5726 | 3758.277 | 504.1642 | 0.010956 | 4.74E-12 | 2.152463 |
| Mtr.31448.1.S1_x_at | Mtr.31448.1 | AJ848642 /FEA = mRNA /DEF = similar to UP\|NIA_LOTJA (P39869) Nitrate reductase [NADH] (NR), partial (8%) | AJ848642 | 6.731572 | 1.044538 | 14.46105 | 4.050463 | 0.032883 | 1.32E-37 | 2.148243 |
| Mtr.43393.1.S1_at | Mtr.43393.1 | TC95204 /FEA = mRNA /DEF = weakly similar to UP\|NAS_LYCES (Q9XGI7) Nicotianamine synthase (S-adenosyl-L-methionine:S-adenosyl-L-methionine:S-adenosyl-methionine 3-amino-3-carboxypropyltransferase) (Chloronerva), partial (84%) | TC95204 | 1014.085 | 86.40734 | 2177.974 | 171.9263 | 0.000469 | 0 | 2.147724 |
| Mtr.8505.1.S1_at | Mtr.8505.1 | TC100418 /FEA = mRNA /DEF = similar to UP\|Q06765 (Q06765) ADR6 protein (Sali5-4a protein), partial (68%) | TC100418 | 3038.322 | 492.151 | 6501.841 | 560.1494 | 0.001296 | 0 | 2.139945 |
| Mtr.45103.1.S1_at | Mtr.45103.1 | TC98800 /FEA = mRNA /DEF = similar to UP\|Q8S3C2 (Q8S3C2) GTP cyclohydrolase I, partial (18%) | TC98800 | 75.21676 | 13.28341 | 160.2015 | 13.62552 | 0.001504 | 0 | 2.129864 |
| Mtr.5804.1.S1_at | Mtr.5804.1 | BF650415 /FEA = mRNA /DEF = weakly similar to GB\|AAO44030.1\|28466843\|BT004764 At3g56220 {*Arabidopsis thaliana*}, partial (47%) | BF650415 | 19.10882 | 6.124257 | 40.45365 | 4.844521 | 0.009074 | 2.33E-14 | 2.117015 |

TABLE 3-continued

List of probesets down- and up-regulated in transformed hairy roots by more than two-fold and also at a statistically significant level (p-value <5%). Probesets are found at *Medicago truncatula* Gene Expression Atlas ("MtGEA;" Benedito et al., 2008; He et al., 2009).

| Probesets | Transcript ID(Array Design) | Target Description | Representative Public ID | Ave OE-GUS | SD OE-GUS | Ave OE-PAR | SD OE-PAR | PTS | PTA | Ratio (OE-PAR:OE-GUS) |
|---|---|---|---|---|---|---|---|---|---|---|
| Mtr.27451.1.S1_at | Mtr.27451.1 | BE124481 /FEA = mRNA /DEF= | BE124481 | 43.56527 | 14.58105 | 92.0503 | 4.436768 | 0.005293 | 0 | 2.112928 |
| Mtr.16363.1.S1_s_at | Mtr.16363.1 | IMGAG|868.m00002 /FEA = mRNA /DEF = LQGC hypothetical protein AC135396.30.21 8440 9117 mth2-33o18 Jan. 13, 2005 | IMGAG|868.m00002 | 139.0985 | 67.29957 | 293.1822 | 5.736049 | 0.016801 | 0 | 2.107731 |
| Msa.2939.1.S1_at | Msa.2939.1 | iMsa.2939 /TID = Msa.2939.1 /CNT = 1 /FEA = mRNA /TIER = ConsEnd /STK = 0 /NOTE = sequence(s) not in UniGene /DEF= | TC109 | 119.868 | 36.61586 | 251.9845 | 21.27225 | 0.005678 | 0 | 2.102183 |
| Mtr.40711.1.S1_at | Mtr.40711.1 | TC107889 /FEA = mRNA /DEF = weakly similar to UP Q43583 (Q43583) Hsr201 protein, partial (75%) | TC107889 | 906.4601 | 70.64078 | 1891.396 | 100.0925 | 0.000154 | 0 | 2.086574 |
| Mtr.9728.1.S1_at | Mtr.9728.1 | TC104194 /FEA = mRNA /DEF = similar to GB|AAL10495.1|15983797|AY056804 AT5g39660/MIJ24_130 {*Arabidopsis thaliana*;}, partial (16%) | TC104194 | 47.34348 | 21.52288 | 98.76909 | 7.435708 | 0.01737 | 0 | 2.086224 |
| Mtr.32011.1.S1_at | Mtr.32011.1 | AL389071 /FEA = mRNA /DEF= | AL389071 | 52.39482 | 12.29109 | 109.1084 | 23.90432 | 0.021684 | 1.33E-15 | 2.082427 |
| Mtr.27024.1.S1_at | Mtr.27024.1 | AL389774 /FEA = mRNA /DEF= | AL389774 | 25.91605 | 5.150634 | 53.77898 | 8.085224 | 0.007312 | 7.28E-21 | 2.075123 |
| Mtr.23143.1.S1_at | Mtr.23143.1 | 1654.m00057 /FEA = mRNA /DEF = AC144730.17 96684 96091 mth2-5j23 weakly similar to UP|Q7XZC5 (Q7XZC5) Albumin 1 precursor | 1654.m00057 | 2611.659 | 849.4693 | 5398.906 | 611.11 | 0.00993 | 2.89E-15 | 2.067232 |
| Mtr.31070.1.S1_s_at | Mtr.31070.1 | AA660761 /FEA = mRNA /DEF = similar to GB|AAL05900.1|15777879|AY055100 AT3g15640/MSJ11_4 {*Arabidopsis thaliana*;}, partial (53%) | AA660761 | 347.1108 | 20.11124 | 716.2835 | 22.5441 | 2.95E-05 | 0 | 2.063559 |
| Mtr.39897.1.S1_at | Mtr.39897.1 | TC105988 /FEA = mRNA /DEF = similar to UP|P93697 (P93697) CPRD12 protein, partial (61%) | TC105988 | 12.76636 | 2.427718 | 26.33559 | 7.758552 | 0.044517 | 3.63E-22 | 2.06289 |
| Mtr.11130.1.S1_at | Mtr.11130.1 | TC108984 /FEA = mRNA /DEF= | TC108984 | 37.58262 | 19.77651 | 77.48235 | 10.32217 | 0.036295 | 2.15E-11 | 2.061654 |
| Mtr.12550.1.S1_at | Mtr.12550.1 | TC95205 /FEA = mRNA /DEF = weakly similar to UP|Q8L5A7 (Q8L5A7) Steroid sulfotransferase-like protein (At5g07010), partial (70%) | TC95205 | 860.1017 | 388.5234 | 1769.983 | 375.5879 | 0.043401 | 2.72E-05 | 2.057877 |
| Mtr.42071.1.S1_at | Mtr.42071.1 | TC110696 /FEA = mRNA /DEF = similar to UP|Q8VYU3 (Q8VYU3) GTP cyclohydrolase I, partial (47%) | TC110696 | 71.43369 | 14.03497 | 146.9395 | 30.793 | 0.018077 | 1.18E-20 | 2.057006 |
| Mtr.39846.1.S1_at | Mtr.39846.1 | TC105872 /FEA = mRNA /DEF = similar to UP|Q8W4Y8 (Q8W4Y8) Trypsin/chymotrypsin inhibitor (Fragment), partial (14%) | TC105872 | 23.815 | 9.487137 | 48.84013 | 5.45748 | 0.016674 | 2E-15 | 2.050814 |

TABLE 3-continued

List of probesets down- and up-regulated in transformed hairy roots by more than two-fold and also at a statistically significant level (p-value <5%). Probesets are found at Medicago truncatula Gene Expression Atlas ("MtGEA;" Benedito et al., 2008; He et al., 2009).

| Probesets | Transcript ID(Array Design) | Target Description | Representative Public ID | Ave OE-GUS | SD OE-GUS | Ave OE-PAR | SD OE-PAR | PTS | PTA | Ratio (OE-PAR:OE-GUS) |
|---|---|---|---|---|---|---|---|---|---|---|
| Mtr.40827.1.S1_at | Mtr.40827.1 | TC108133 /FEA = mRNA /DEF = weakly similar to GB|CAA66109.3|48426429|CANST2PRO specific tissue protein 2 {Cicer arietinum;}, partial (70%) | TC108133 | 747.7229 | 259.3841 | 1533.206 | 284.0401 | 0.02408 | 1.56E-07 | 2.0505 |
| Mtr.44300.1.S1_at | Mtr.44300.1 | TC97086 /FEA = mRNA /DEF = similar to UP|Q9ZR88 (Q9ZR88) Bifunctional nuclease (Fragment), partial (93%) | TC97086 | 75.54789 | 34.64619 | 154.9086 | 9.188523 | 0.018541 | 0 | 2.050469 |
| Mtr.37042.1.S1_at Mtr.22842.1.S1_s_at | Mtr.37042.1 Mtr.22842.1 | TC110897 /FEA = mRNA /DEF = 1631.m00057 /FEA = mRNA /DEF = AC138465.20 116022 117716 mth2-23h19 weakly similar to UP|Q8H612 (Q8H612) Pentatricopeptide (PPR) repeat-containing protein-like | TC110897 1631.m00057 | 20.83234 94.99832 | 5.381611 32.33108 | 42.64093 194.2188 | 1.777659 33.78853 | 0.002633 0.0213 | 0 1.06E-07 | 2.046862 2.044444 |
| Mtr.49527.1.S1_at | Mtr.49527.1 | IMGAG|1106.m00022 /FEA = mRNA /DEF = Lipolytic enzyme, G-D-S-L. AC146586.2.221 91053 88472 mth2-71m12 Jan. 13, 2005 | IMGAG|1106.m00022 | 10.90944 | 2.480131 | 22.12558 | 3.280984 | 0.009148 | 4.76E-15 | 2.028113 |
| Mtr.41946.1.S1_at | Mtr.41946.1 | TC110438 /FEA = mRNA /DEF = similar to GB|AAL05900.1|15777879|AY055100 AT3g15640/MSJ11_4 {Arabidopsis thaliana;}, partial (67%) | TC110438 | 614.7155 | 63.04668 | 1246.147 | 39.46543 | 0.000124 | 0 | 2.027193 |
| Mtr.11192.1.S1_at | Mtr.11192.1 | TC109165 /FEA = mRNA /DEF = similar to UP|Q9FUK3 (Q9FUK3) Cytokinin-regulated kinase 1, partial (29%) | TC109165 | 51.64972 | 15.81417 | 104.5602 | 15.95759 | 0.015109 | 6.83E-09 | 2.024409 |
| Mtr.24497.1.S1_at | Mtr.24497.1 | 1744.m00038 /FEA = mRNA /DEF = AC151668.21 49824 44618 mth2-6e22 weakly similar to TIGR_Ath1|At1g14570-GOpep.168408. m01564 expressed protein, partial (28%) | 1744.m00038 | 26.87012 | 7.203024 | 53.78477 | 6.803399 | 0.009274 | 7.28E-12 | 2.001657 |
| Mtr.28447.1.S1_at Mtr.41854.1.S1_s_at | Mtr.28447.1 Mtr.41854.1 | BG645848 /FEA = mRNA /DEF = TC110250 /FEA = mRNA /DEF = similar to UP|Q9MA26 (Q9MA26) T5E21.7, partial (14%) | BG645848 TC110250 | 29.61205 27.60078 | 2.906507 4.98102 | 59.24899 55.2228 | 11.91676 8.326096 | 0.013863 0.007867 | 8.33E-70 7.62E-22 | 2.000841 2.000769 |
| Mtr.23572.1.S1_at | Mtr.23572.1 | 1681.m00026 /FEA = mRNA /DEF = AC146750.20 21226 20705 mth2-16o6 similar to UP|P93713 (P93713) PEThy; ZPT2-5 | 1681.m00026 | 108.7813 | 33.28696 | 54.01083 | 6.087249 | 0.048641 | 9.32E-55 | 0.496508 |
| Mtr.45131.1.S1_at | Mtr.45131.1 | TC98879 /FEA = mRNA /DEF = similar to UP|Q9FKJ9 (Q9FKJ9) Gb|AAF24606.1, partial (17%) | TC98879 | 36.80421 | 7.765868 | 18.20608 | 3.79032 | 0.020337 | 1.92E-17 | 0.494674 |

TABLE 3-continued

List of probesets down- and up-regulated in transformed hairy roots by more than two-fold and also at a statistically significant level (p-value <5%). Probesets are found at Medicago truncatula Gene Expression Atlas ("MtGEA;" Benedito et al. 2008; He et al. 2009).

| Probesets | Transcript ID (Array Design) | Target Description | Representative Public ID | Ave OE-GUS | SD OE-GUS | Ave OE-PAR | SD OE-PAR | PTS | PTA | Ratio (OE-PAR:OE-GUS) |
|---|---|---|---|---|---|---|---|---|---|---|
| Mtr.33150.1.S1_s_at | Mtr.33150.1 | BF644297 /FEA = mRNA /DEF = similar to UP|Q8S902 (Q8S902) Syringolide-induced protein 19-1-5, partial (25%) | BF644297 | 212.6908 | 66.46657 | 105.0397 | 9.379603 | 0.049933 | 6.19E-88 | 0.493861 |
| Mtr.33148.1.S1_at | Mtr.33148.1 | BF644261 /FEA = mRNA /DEF = homologue to UP|O22247 (O22247) Small nuclear ribonucleoprotein-like protein (At2g47640), partial (87%) | BF644261 | 74.39456 | 10.79339 | 36.49784 | 4.716791 | 0.005082 | 5.06E-44 | 0.490598 |
| Mtr.42263.1.S1_at | Mtr.42263.1 | TC111084 /FEA = mRNA /DEF = similar to UP|Q9ZTM8 (Q9ZTM8) PGPS/D12, partial (47%) | TC111084 | 345.4222 | 71.55666 | 169.1052 | 71.35791 | 0.039087 | 1.87E-05 | 0.489561 |
| Mtr.6648.1.S1_s_at | Mtr.6648.1 | BQ153446 /FEA = mRNA /DEF = similar to UP|Q8GTJ0 (Q8GTJ0) Xyloglucan endotransglycosylase, partial (30%) | BQ153446 | 481.3641 | 109.1397 | 234.7549 | 21.66545 | 0.018479 | 1.6E-86 | 0.487687 |
| Msa.1604.1.S1_at | Msa.1604.1 | iMsa.1604 /TID = Msa.1604.1 /CNT = 1 /FEA = mRNA /TIER = ConsEnd /STK = 0 /NOTE = sequence(s) not in UniGene /DEF= | TC151 | 1184.941 | 367.0642 | 576.7456 | 91.10772 | 0.049547 | 6.39E-31 | 0.48673 |
| Mtr.48557.1.S1_at | Mtr.48557.1 | IMGAG|1164.m00004 /FEA = mRNA /DEF = Protein of unknown function DUF588; Plant integral membrane protein AC147364.7.31 14158 12772 mth2-68g24 Jan. 13, 2005 | IMGAG|1164.m00004 | 323.4778 | 16.86926 | 156.4709 | 21.13107 | 0.000433 | 0 | 0.483715 |
| Mtr.12560.1.S1_at | Mtr.12560.1 | TC95232 /FEA = mRNA /DEF = similar to UP|GTX6_SOYBN (P32110) Probable glutathione S-transferase (Heat shock protein 26A) (G2-4), complete | TC95232 | 467.0138 | 89.42901 | 225.3946 | 7.236743 | 0.009558 | 0 | 0.482629 |
| Mtr.42263.1.S1_s_at | Mtr.42263.1 | TC111084 /FEA = mRNA /DEF = similar to UP|Q9ZTM8 (Q9ZTM8) PGPS/D12, partial (47%) | TC111084 | 245.3696 | 27.9992 | 118.1749 | 33.31503 | 0.007168 | 3.55E-15 | 0.48162 |
| Mtr.10522.1.S1_s_at | Mtr.10522.1 | TC107029 /FEA = mRNA /DEF = similar to PIR|D96538|D96538 cytosolic tRNA-Ala synthetase [imported] - Arabidopsis thaliana {Arabidopsis thaliana;}, partial (33%) | TC107029 | 98.24196 | 20.28132 | 47.11848 | 5.335859 | 0.013452 | 7.58E-62 | 0.479617 |
| Mtr.48743.1.S1_at | Mtr.48743.1 | IMGAG|1155.m00004 /FEA = mRNA /DEF = Ribonuclease T2 AC146971.12.41 23294 21472 mth2-128d1 Jan. 13, 2005 | IMGAG|1155.m00004 | 35.44762 | 9.171154 | 16.60698 | 3.220422 | 0.028377 | 3.94E-24 | 0.468494 |
| Mtr.8517.1.S1_at | Mtr.8517.1 | TC100462 /FEA = mRNA /DEF = similar to UP|MTD_FRAAN (Q9ZRF1) Probable mannitol dehydrogenase (NAD-dependent mannitol dehydrogenase), partial (98%) | TC100462 | 514.6957 | 128.2066 | 240.2763 | 6.400827 | 0.020785 | 0 | 0.466832 |
| Mtr.19456.1.S1_s_at | Mtr.19456.1 | IMGAG|1178.m00016 /FEA = mRNA /DEF = AAA ATPase, central region | IMGAG|1178.m00016 | 93.59327 | 25.71178 | 43.12689 | 4.928968 | 0.028867 | 2.29E-70 | 0.460791 |

TABLE 3-continued

List of probesets down- and up-regulated in transformed hairy roots by more than two-fold and also at a statistically significant level (p-value <5%). Probesets are found at *Medicago truncatula* Gene Expression Atlas ("MtGEA;" Benedito et al. 2008; He et al. 2009).

| Probesets | Transcript ID (Array Design) | Target Description | Representative Public ID | Ave OE-GUS | SD OE-GUS | Ave OE-PAR | SD OE-PAR | PTS | PTA | Ratio (OE-PAR:OE-GUS) |
|---|---|---|---|---|---|---|---|---|---|---|
| Mtr.26842.1.S1_at Msa.509.1.S1_at | Mtr.26842.1 Msa.509.1 | AC147498.14.151 61265 62827 mth2-6f18 Jan. 13, 2005 AJ845621 /FEA = mRNA /DEF= iMsa.509 /TID = Msa.509.1 /CNT = 1 /FEA = mRNA /TIER = ConsEnd /STK = 0 /NOTE = sequence(s) not in UniGene /DEF= | AJ845621 50319249 | 539.8633 262.3813 | 134.4481 50.30794 | 247.4114 120.2051 | 77.44588 2.851212 | 0.030944 0.008119 | 6.13E-11 0 | 0.458285 0.458131 |
| Mtr.4438.1.S1_at | Mtr.4438.1 | AJ503481 /FEA = mRNA /DEF = similar to UP|Q6RVV4 (Q6RVV4) Short-chain dehydrogenase Ttc32, partial (26%) /DEF= | AJ503481 | 30.73882 | 6.215417 | 13.94658 | 5.988667 | 0.028049 | 1.19E-06 | 0.453712 |
| Mtr.10758.1.S1_at Mtr.34114.1.S1_s_at | Mtr.10758.1 Mtr.34114.1 | TC107813 /FEA = mRNA /DEF= BQ138448 /FEA = mRNA /DEF = similar to UP|Q39450 (Q39450) Pathogenesis related protein, complete | TC107813 BQ138448 | 735.6056 766.457 | 154.1225 236.75850 | 327.7808 339.3063 | 76.00594 34.32268 | 0.014726 0.036483 | 1.49E-20 4.7E-103 | 0.445593 0.442695 |
| Mtr.45232.1.S1_at | Mtr.45232.1 | TC99118 /FEA = mRNA /DEF = similar to UP|DR2A_ARATH (O82132) Dehydration responsive element binding protein 2A (DREB2A protein), partial (23%) | TC99118 | 34.86944 | 10.9945 | 15.08662 | 3.861679 | 0.042371 | 7.12E-19 | 0.43266 |
| Mtr.50075.1.S1_s_at | Mtr.50075.1 | IMGAG|986.m00012 /FEA = mRNA /DEF = RmlC-like cupin; Germin; Cupin; Cupin region AC140721.15.111 62212 61323 mth2-16c16 Jan. 13, 2005 | IMGAG|986.m00012 | 77.37295 | 26.95238 | 33.08377 | 2.74053 | 0.04727 | 2.1E-172 | 0.427588 |
| Mtr.8990.1.S1_at | Mtr.8990.1 | TC102027 /FEA = mRNA /DEF = homologue to UP|Q9AUH7 (Q9AUH7) UVI1, partial (79%) | TC102027 | 2077.807 | 721.2363 | 883.6478 | 53.60517 | 0.045935 | 0 | 0.425279 |
| Mtr.37415.1.S1_s_at | Mtr.37415.1 | TC100611 /FEA = mRNA /DEF = similar to UP|Q9SE03 (Q9SE03) Copper chaperone homolog CCH, partial (82%) | TC100611 | 9217.674 | 691.6444 | 3862.131 | 227.2631 | 0.000219 | 0 | 0.418992 |
| Mtr.14224.1.S1_at | Mtr.14224.1 | IMGAG|1216.m00002 /FEA = mRNA /DEF = Proteinase inhibitor I13, potato inhibitor I AC148487.14.21 8524 8228 mth2-57f20 Jan. 13, 2005 | IMGAG|1216.m00002 | 1888.532 | 386.4314 | 786.7926 | 169.0794 | 0.010625 | 1.53E-29 | 0.416616 |
| Mtr.44470.1.S1_at | Mtr.44470.1 | TC97425 /FEA = mRNA /DEF = weakly similar to UP|Q9LIR0 (Q9LIR0) *Arabidopsis thaliana* genomic DNA, chromosome 3, BAC clone: F14O13, partial (7%) | TC97425 | 67.81564 | 22.79712 | 28.13261 | 5.262464 | 0.042485 | 5.5E-39 | 0.41484 |
| Mtr.26833.1.S1_at Msa.2910.1.S1_at | Mtr.26833.1 Msa.2910.1 | AJ503813 /FEA = mRNA /DEF= iMsa.2910 /TID = Msa.2910.1 /CNT = 1 /FEA = mRNA /TIER = ConsEnd /STK = 0 /NOTE = sequence(s) not in UniGene /DEF= | AJ503813 gi|535355|gb|U13709.1| MSU13709 | 124.3928 2750.135 | 7.436086 921.0257 | 49.61036 1090.065 | 9.613204 190.4528 | 0.000439 0.037762 | 0 1.69E-51 | 0.39882 0.396368 |
| Mtr.23272.1.S1_at | Mtr.23272.1 | 1663.m00036 /FEA = mRNA /DEF = AC145202.17 61879 62690 mth2-15e9 weakly similar to UP|Q8LNY0 | 1663.m00036 | 632.6005 | 198.7635 | 243.1869 | 48.40887 | 0.030017 | 3.99E-44 | 0.384424 |

TABLE 3-continued

List of probesets down- and up-regulated in transformed hairy roots by more than two-fold and also at a statistically significant level (p-value <5%). Probesets are found at *Medicago truncatula* Gene Expression Atlas ("MtGEA;" Benedito et al. 2008; He et al. 2009).

| Probesets | Transcript ID(Array Design) | Target Description | Representative Public ID | Ave OE-GUS | SD OE-GUS | Ave OE-PAR | SD OE-PAR | PTS | PTA | Ratio (OE-PAR:OE-GUS) |
|---|---|---|---|---|---|---|---|---|---|---|
| Mtr.43157.1.S1_at | Mtr.43157.1 | (Q8LNY0) Protease inhibitor 2 (Fragment) TC94674 /FEA = mRNA /DEF = homologue to GB|AAB49302.1|1872517|ATU85244 alternative oxidase {*Arabidopsis thaliana*;}, partial (90%) | TC94674 | 1247.775 | 434.8176 | 472.6399 | 175.6558 | 0.045796 | 2.12E-14 | 0.378786 |
| Mtr.40504.1.S1_at | Mtr.40504.1 | TC107427 /FEA = mRNA /DEF = weakly similar to UP|Q6Y195 (Q6Y195) O-methyltransferase, partial (79%) | TC107427 | 1179.124 | 406.0342 | 440.4643 | 207.0652 | 0.048464 | 6.46E-10 | 0.373552 |
| Mtr.14430.1.S1_at | Mtr.14430.1 | IMGAG|1004.m00003 /FEA = mRNA /DEF = Oligopeptide transporter OPT superfamily AC141323.7.31 12365 8745 mth2-6a23 Jan. 13, 2005 | IMGAG|1004.m00003 | 120.4673 | 21.97937 | 44.64807 | 5.612255 | 0.004425 | 4.3E-121 | 0.370624 |
| Mtr.50074.1.S1_at | Mtr.50074.1 | IMGAG|986.m00013 /FEA = mRNA /DEF = RmlC-like cupin; Germin; Cupin; Cupin region AC140721.15.121 64859 65757 mth2-16c16 Jan. 13, 2005 | IMGAG|986.m00013 | 16.04955 | 4.865213 | 5.848582 | 2.286598 | 0.030309 | 1.1E-14 | 0.364408 |
| Mtr.32209.1.S1_at | Mtr.32209.1 | AW684842 /FEA = mRNA /DEF = homologue to UP|Q7KRX2 (Q7KRX2) CG33103-PA isoform A, partial (0%) | AW684842 | 37.41163 | 4.765853 | 13.37813 | 4.336354 | 0.002956 | 0 | 0.357593 |
| Mtr.10662.1.S1_at | Mtr.10662.1 | TC107529 /FEA = mRNA /DEF = similar to UP|HS2M_PEA (P46254) Heat shock 22 kDa protein, mitochondrial precursor, partial (95%) | TC107529 | 1199.274 | 467.3532 | 395.7445 | 17.54732 | 0.040906 | 0 | 0.329987 |
| Mtr.43158.1.S1_s_at | Mtr.43158.1 | TC94675 /FEA = mRNA /DEF = similar to UP|AOX1_TOBAC (Q41224) Alternative oxidase 1, mitochondrial precursor, partial (32%) | TC94675 | 419.3234 | 130.9232 | 137.0082 | 30.37405 | 0.021998 | 2.6E-58 | 0.326736 |
| Mtr.8550.1.S1_s_at | Mtr.8550.1 | TC100587 /FEA = mRNA /DEF = similar to UP|LGB2_VICFA (P93848) Leghemoglobin 29 (VfLb29), complete | TC100587 | 32.55662 | 5.816939 | 10.20394 | 1.414009 | 0.002944 | 4.7E-165 | 0.313421 |
| Mtr.13532.1.S1_at | Mtr.13532.1 | TC98300 /FEA = mRNA /DEF = similar to UP|Q9XFX1 (Q9XFX1) Cytochrome P450, partial (46%) | TC98300 | 133.1686 | 55.58377 | 39.35262 | 8.602147 | 0.044607 | 1.38E-79 | 0.29551 |
| Mtr.8284.1.S1_s_at | Mtr.8284.1 | MTUCP49TVB /FEA = mRNA /DEF = similar to UP|LGB4_MEDSA (P28010) Leghemoglobin, partial (42%) | MTUCP49TVB | 65.59502 | 2.387178 | 19.35398 | 4.369956 | 8.74E-05 | 0 | 0.295053 |
| Mtr.14692.1.S1_at | Mtr.14692.1 | IMGAG|758.m00012 /FEA = mRNA /DEF = Helix-turn-helix, Fis-type; Transcription factor, K-box AC123898.40.121 63530 62038 mth2-31m6 Jan. 13, 2005 | IMGAG|758.m00012 | 295.5592 | 119.5951 | 86.20861 | 15.39617 | 0.039662 | 1.2E-122 | 0.29168 |
| Mtr.25451.1.S1_at | Mtr.25451.1 | 1417.m00057 /FEA = mRNA /DEF = AC125476.30 106640 113980 | 1417.m00057 | 329.7007 | 119.1834 | 95.56038 | 8.914978 | 0.027449 | 0 | 0.28984 |

TABLE 3-continued

List of probesets down- and up-regulated in transformed hairy roots by more than two-fold and also at a statistically significant level (p-value <5%). Probesets are found at *Medicago truncatula* Gene Expression Atlas ("MtGEA;" Benedito et al. 2008; He et al. 2009).

| Probesets | Transcript ID (Array Design) | Target Description | Representative Public ID | Ave OE-GUS | SD OE-GUS | Ave OE-PAR | SD OE-PAR | PTS | PTA | Ratio (OE-PAR:OE-GUS) |
|---|---|---|---|---|---|---|---|---|---|---|
| Mtr.43877.1.S1_at | Mtr.43877.1 | mth2-10e13 similar to TIGR_Ath1|At1g50200-GOpep.168408.m05157 alanine--tRNA ligase-related similar to alanine--tRNA ligase, partial (39%) | TC96232 | 211.2336 | 40.95913 | 59.3035 | 18.96201 | 0.004312 | 8.64E-44 | 0.280748 |
| Mtr.29279.1.S1_at | Mtr.29279.1 | TC96232 /FEA = mRNA /DEF = similar to PIR|T48875|T48875 copper transport protein [imported] - *Arabidopsis thaliana* {*Arabidopsis thaliana*;}, partial (46%) | CB892810 | 64.71457 | 26.70458 | 18.15443 | 10.06084 | 0.047539 | 1.1E-15 | 0.280531 |
| Mtr.37751.1.S1_at | Mtr.37751.1 | CB892810 /FEA = mRNA /DEF = similar to UP|Q96573 (Q96573) Lipoxygenase, partial (30%) | TC101337 | 301.8951 | 88.13819 | 83.13192 | 12.38967 | 0.013083 | 2.1E-205 | 0.275367 |
| Mtr.44545.1.S1_at Mtr.34591.1.S1_s_at | Mtr.44545.1 Mtr.34591.1 | TC101337 /FEA = mRNA /DEF = similar to UP|7MT9_MEDSA (O22309) Isoflavone-7-O-methyltransferase 9 (Isoflavone-O-methyltransferase 9) (7 IOMT-9), partial (37%) TC97577 /FEA = mRNA /DEF = BQ152604 /FEA = mRNA /DEF = similar to UP|Q8LNY0 (Q8LNY0) Protease inhibitor 2 (Fragment), partial (75%) | TC97577 BQ152604 | 410.4233 994.945 | 56.30856 465.0277 | 111.1992 243.6699 | 8.089142 6.926287 | 0.000805 0.048916 | 0 0 | 0.270938 0.244908 |
| Mtr.8297.1.S1_at Mtr.24451.1.S1_at | Mtr.8297.1 Mtr.24451.1 | MTVAU52TV /FEA = mRNA /DEF = 1741.m00060 /FEA = mRNA /DEF = AC151525.10 132154 132664 mth2-77j8 | MTVAU52TV 1741.m00060 | 86.00236 166.1294 | 32.18278 32.39907 | 20.82475 39.748 | 2.808697 26.18176 | 0.02502 0.006276 | 0 6.23E-17 | 0.242142 0.239259 |
| Mtr.43609.1.S1_at | Mtr.43609.1 | TC95697 /FEA = mRNA /DEF = weakly similar to UP|Q6K3E9 (Q6K3E9) F-box family protein-like, partial (35%) | TC95697 | 255.4591 | 118.2874 | 56.74687 | 6.308619 | 0.043873 | 0 | 0.222137 |
| Mtr.51040.1.S1_s_at | Mtr.51040.1 | IMGAG|729.m00012 /FEA = mRNA /DEF = Cytochrome b-245, heavy chain; Phenol hydroxylase reductase; Ferric reductase-like transmembrane component AC121237.19.111 36606 39780 mth2-22g11 Jan. 13, 2005 | IMGAG|729.m00012 | 389.5528 | 56.34564 | 84.55705 | 9.993006 | 0.000765 | 0 | 0.217062 |
| Mtr.13623.1.S1_at Mtr.25451.1.S1_s_at | Mtr.13623.1 Mtr.25451.1 | TC98573 /FEA = mRNA /DEF = 1417.m00057 /FEA = mRNA /DEF = AC125476.30 106640 113980 mth2-10e13 similar to TIGR_Ath1|At1g50200-GOpep.168408.m05157 alanine--tRNA ligase-related similar to alanine--tRNA ligase, partial (39%) | TC98573 1417.m00057 | 77.63739 151.5841 | 11.60822 61.32089 | 16.31947 31.20105 | 2.136159 4.668218 | 0.000845 0.027518 | 0 0 | 0.210201 0.205833 |

TABLE 3-continued

List of probesets down- and up-regulated in transformed hairy roots by more than two-fold and also at a statistically significant level (p-value <5%). Probesets are found at *Medicago truncatula* Gene Expression Atlas ("MtGEA;" Benedito et al. 2008; He et al. 2009).

| Probesets | Transcript ID (Array Design) | Target Description | Representative Public ID | Ave OE-GUS | SD OE-GUS | Ave OE-PAR | SD OE-PAR | PTS | PTA | Ratio (OE-PAR:OE-GUS) |
|---|---|---|---|---|---|---|---|---|---|---|
| Mtr.27753.1.S1_at | Mtr.27753.1 | BE998400 /FEA = mRNA /DEF = similar to UP|Q96569 (Q96569) L-lactate dehydrogenase, partial (62%) | BE998400 | 195.7362 | 72.49264 | 39.69109 | 0.06186 | 0.020326 | 0 | 0.202778 |
| Mtr.44349.1.S1_at | Mtr.44349.1 | TC97188 /FEA = mRNA /DEF = UP|Q9AWG7 (Q9AWG7) Zinc transporter, partial (96%) | TC97188 | 1115.947 | 89.81108 | 219.0508 | 4.170486 | 6.58E-05 | 0 | 0.196291 |
| Mtr.23266.1.S1_at | Mtr.23266.1 | 1663.m00030 /FEA = mRNA /DEF = AC145202.17_44559_44888 mth2-15e9 weakly similar to UP|Q6YEY6 (Q6YEY6) Protease inhibitor | 1663.m00030 | 438.6837 | 214.4506 | 79.15013 | 2.30515 | 0.043956 | 0 | 0.180426 |
| Mtr.28310.1.S1_at | Mtr.28310.1 | BG588509 /FEA = mRNA /DEF = similar to PDB|1SCH_A|16331301|SCH_A Chain A, Peanut Peroxidase. {*Arachis hypogaea*}, partial (68%) | BG588509 | 152.8108 | 25.76567 | 27.07278 | 1.12482 | 0.001077 | 0 | 0.177165 |
| Mtr.38954.1.S1_at | Mtr.38954.1 | TC103902 /FEA = mRNA /DEF = weakly similar to UP|Q6EMC0 (Q6EMC0) Ferric-chelate reductase, partial (23%) | TC103902 | 885.9769 | 136.5601 | 125.1288 | 19.31496 | 0.00067 | 0 | 0.141233 |

Figure 10:
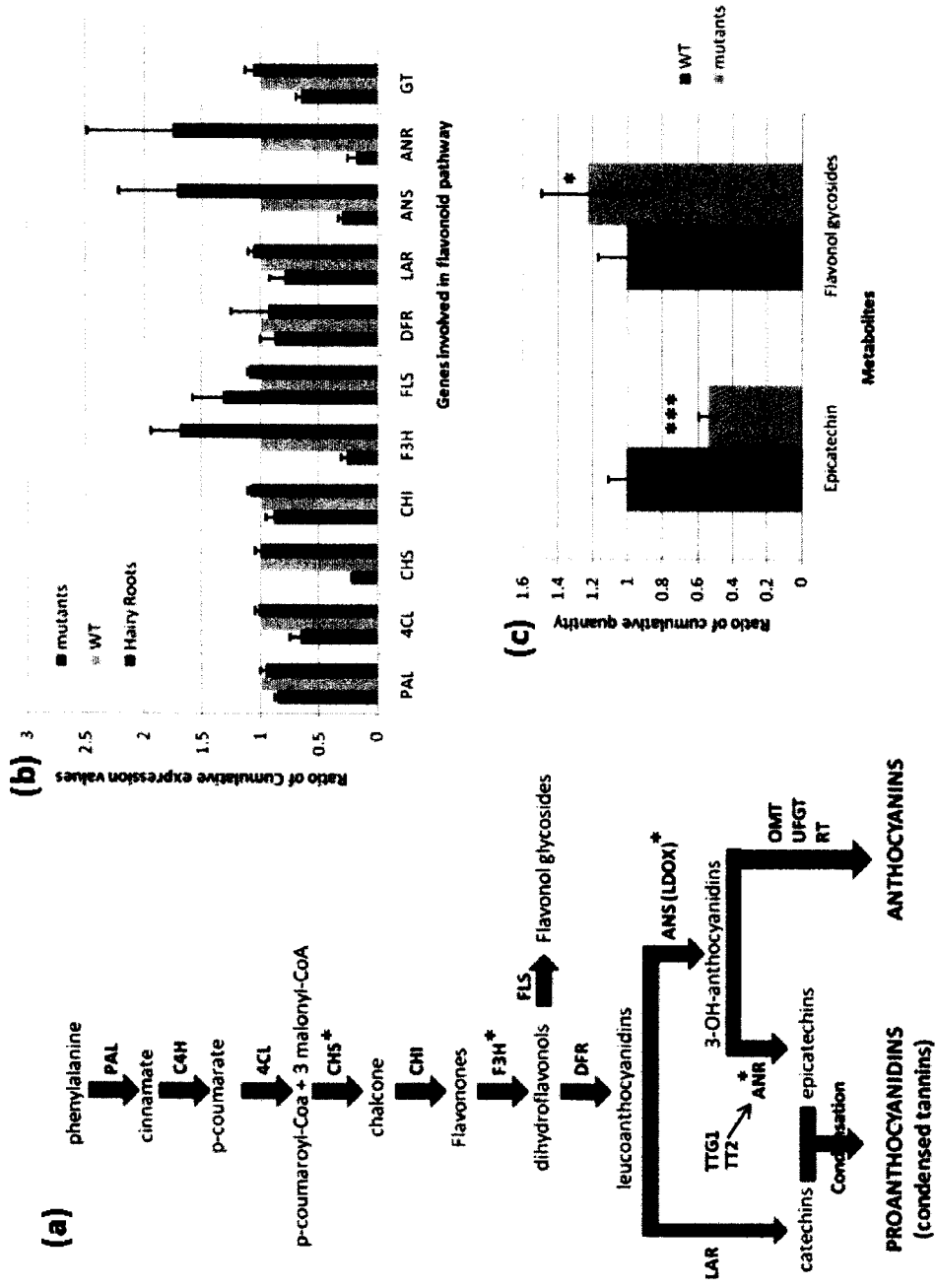
FIG. 10: (a) Schematic representation of the flavonoid biosynthetic pathway leading to PAs and anthocyanins. * represents enzymes for which transcript levels are significantly affected in both mutant lines and over-expressing transformants. PAL, phenylalanine ammonia-lyase; C4H, cinnamate 4-hydroxylase; 4CL, 4-coumarate CoA ligase; CHS, chalcone synthase; CHI, chalcone isomerase; F3H, flavanone 3-hydroxylase; FLS, flavonol synthase; DFR, dihydroflavonol 4-reductase; LAR, leucoanthocyanidin reductase; ANS, anthocyanidin synthase; ANR, anthocyanidin reductase; OMT, o-methyltransferase; UFGT, UDP flavonoid glucosyl transferase; RT, rhamnosyl transferase; GT, glucosyl transferase; TT2, transparent testa2; TT8, transparent testa8; TTG1, transparent testa glabral. (b) Cumulative expression values of different probesets encoding putative genes involved in flavonoid biosynthesis. Averages of the three biological replicates are indicated with their respective SD. PAL gene expression is constituted by cumulative expression of 8 different probesets encoding for putative PAL enzyme; 4CL by 17 probesets; CHS, 31 probesets; CHI, 10 probesets; F3H, 12 probesets; FLS, 3 probesets; DFR, 4 probesets; JAR, 1 probeset; ANS, 3 probesets; ANR, 2 probesets; GT, 6 probesets; TT2-like, 1 probeset; TT8-like, 2 probesets; TTG1-like, 2 probesets. Different probeset IDs for each gene are indicated in supplementary material S6. Expression values for WT were normalized against respective control lines and adjusted to 1. (c) Statistically significant changes in flavonoid content in par mutants with respect to their segregant WT lines. All other flavonoid content changes are indicated in Table 5. Averages of the three biological replicates are indicated with their respective SD.
Figure 11:
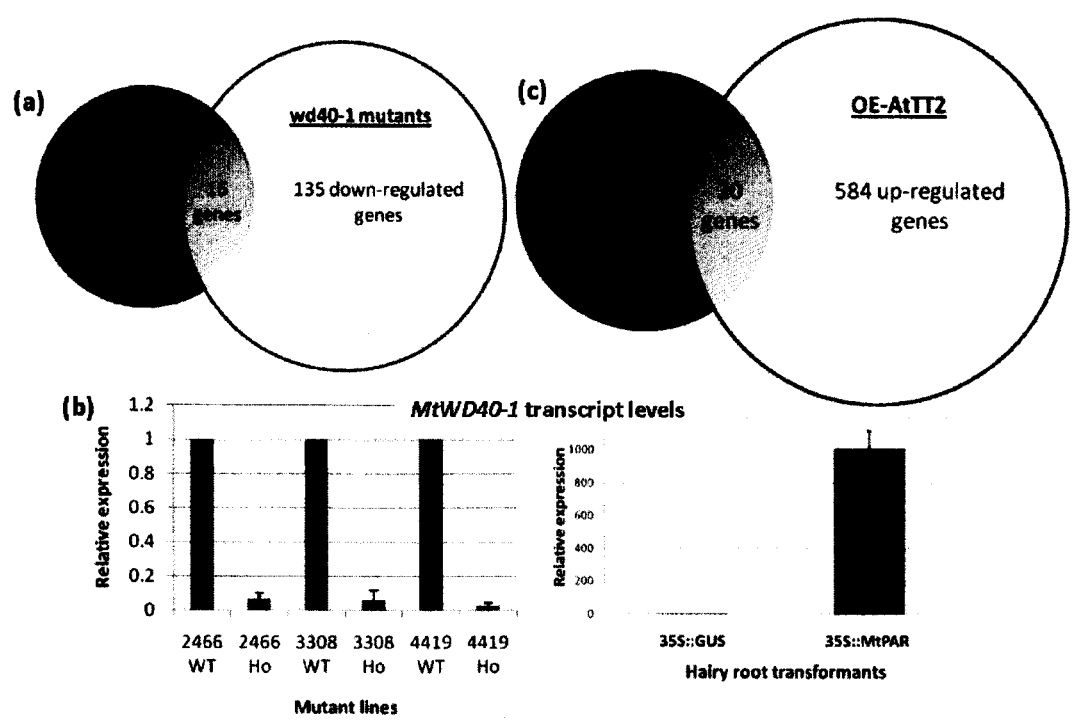
FIG. 11: a) Venn diagram for genes affected in par and ttg1 mutants in *M. truncatula*. A complete list of common probesets down-regulated in par and ttg1 mutant lines is given in Table 6. (b) Transcript levels of MtWD40-1 in different par lines and in hairy roots transformants. Relative expression was calculated from qRT-PCR data with respect to transcript levels of two housekeeping genes MSC27 and PDF2. (c) Venn diagram for genes affected by over-expression of MtPAR and AtTT2 in *M. truncatula* hairy roots. A complete list of common probesets up-regulated in hairy root transformants over-expressing PAR and TT2 is given in Table 7.

To identify genes that might be regulated directly by MtPAR, genes that were 'repressed' in the par mutants were compared with those induced in p35S::MtPAR lines relative to their appropriate controls (FIG. 9a). Twelve genes satisfied both criteria and 8 of these encode enzymes involved in PA and anthocyanin biosynthesis (FIG. 9a, FIG. 10a). Amongst these were genes encoding ANS and ANR, which carry out the last two steps in the synthesis of epicatechin, which is the building block for PAs in *Medicago* (FIG. 10b). MtGEA probeset IDs for enzymes shown in FIG. 10b are listed in Table 4.

TABLE 4

List of probeset IDs for enzymes of FIG. 10b.

| Probesets | Name | BINS | Target Description |
|---|---|---|---|
| Mtr.12556.1.S1_at | 4CL | 16.2.1.3 | TC95226/FEA = mRNA/DEF = similar to UP \| Q9SMT7 (Q9SMT7) 4-coumarate-CoA ligase-like protein (Adenosine monophosphate binding protein 3 AMPBP3), partial (82%) |
| Mtr.13904.1.S1_at | 4CL | 16.2.1.3 | TC99584/FEA = mRNA/DEF = similar to UP \| Q9M0X9 (Q9M0X9) 4-coumarate-CoA ligase-like protein, partial (29%) |
| Mtr.2048.1.S1_at | 4CL | 16.2.1.3 | BF004585/FEA = mRNA/DEF = similar to UP \| 4CL1_SOYBN (P31686) 4-coumarate--CoA ligase 1 (4CL 1) (4-coumaroyl-CoA synthetase 1) (Clone 4CL14) (Fragment), partial (25%) |
| Mtr.25611.1.S1_at | 4CL | 16.2.1.3 | 1438.m00031/FEA = mRNA/DEF = AC144503.17 28902 32269 mth2-13f22 similar to UP \| Q8W558 (Q8W558) 4-coumarate: CoA ligase (EC 6.2.1.12) |
| Mtr.32034.1.S1_at | 4CL | 16.2.1.3 | AL389862/FEA = mRNA/DEF = similar to UP \| Q9M0X9 (Q9M0X9) 4-coumarate-CoA ligase-like protein, partial (31%) |
| Mtr.32035.1.S1_at | 4CL | 16.2.1.3 | AL389863/FEA = mRNA/DEF = similar to UP \| Q42880 (Q42880) 4-coumarate: CoA ligase, partial (4%) |
| Mtr.33696.1.S1_at | 4CL | 16.2.1.3 | BI264867/FEA = mRNA/DEF = similar to UP \| Q84P23 (Q84P23) 4-coumarate-CoA ligase-like protein, partial (13%) |
| Mtr.36885.1.S1_at | 4CL | 16.2.1.3 | CX540116/FEA = mRNA/DEF = similar to UP \| Q9M0X9 (Q9M0X9) 4-coumarate-CoA ligase-like protein, partial (2%) |
| Mtr.41031.1.S1_at | 4CL | 16.2.1.3 | TC108579/FEA = mRNA/DEF = homologue to PIR \| PQ0772 \| PQ0772 4-coumarate-CoA ligase (clone GM4CL1B) - soybean (fragment) {*Glycine max*;}, partial (62%) |
| Mtr.42330.1.S1_at | 4CL | 16.2.1.3 | TC111254/FEA = mRNA/DEF = weakly similar to UP \| O49414 (O49414) 4-coumarate-CoA ligase-like (4-coumarate CoA ligase isoform 7), partial (37%) |
| Mtr.42337.1.S1_at | 4CL | 16.2.1.3 | TC111271/FEA = mRNA/DEF = similar to UP \| Q8S5C1 (Q8S5C1) 4-coumarate: CoA ligase isoenzyme 2, partial (48%) |
| Mtr.43335.1.S1_at | 4CL | 16.2.1.3 | TC95093/FEA = mRNA/DEF = similar to UP \| Q8S564 (Q8S564) 4-coumarate: coenzyme A ligase, partial (95%) |
| Mtr.44778.1.S1_at | 4CL | 16.2.1.3 | TC98074/FEA = mRNA/DEF = similar to UP \| Q84P23 (Q84P23) 4-coumarate-CoA ligase-like protein, partial (26%) |
| Mtr.45561.1.S1_at | 4CL | 16.2.1.3 | TC99926/FEA = mRNA/DEF = similar to UP \| Q9FGW4 (Q9FGW4) 4-coumarate-CoA ligase-like protein (4-coumarate CoA ligase isoform 4) (At5g63380), partial (35%) |
| Mtr.4878.1.S1_at | 4CL | 16.2.1.3 | AL388151/FEA = mRNA/DEF = similar to UP \| Q84P23 (Q84P23) 4-coumarate-CoA ligase-like protein, partial (2%) |
| Mtr.9435.1.S1_at | 4CL | 16.2.1.3 | TC103345/FEA = mRNA/DEF = weakly similar to UP \| Q9M0X9 (Q9M0X9) 4-coumarate-CoA ligase-like protein, partial (40%) |
| Mtr.9793.1.S1_at | 4CL | 16.2.1.3 | TC104410/FEA = mRNA/DEF = similar to UP \| Q84P21 (Q84P21) 4-coumarate-CoA ligase-like protein, partial (41%) |
| Mtr.44985.1.S1_at | ANR | NA | TC98546/FEA = mRNA/DEF = UP \| Q84XT1 (Q84XT1) Anthocyanidin reductase, complete |
| Mtr.7129.1.S1_at | ANR | NA | CX542303/FEA = mRNA/DEF = UP \| Q84XT1 (Q84XT1) Anthocyanidin reductase, partial (13%) |
| Mtr.14017.1.S1_at | ANS | NA | TC99980/FEA = mRNA/DEF = weakly similar to UP \| LDOX_ARATH (Q96323) Leucoanthocyanidin dioxygenase (LDOX) (Leucocyanidin oxygenase) (Leucoanthocyanidin hydroxylase) (Anthocyanidin synthase) (ANS), partial (19%) |
| Mtr.28774.1.S1_at | ANS | 16.8.1.1001 | BM812824/FEA = mRNA/DEF = similar to UP \| Q6PTC5 (Q6PTC5) Anthocyanidin synthase, partial (53%) |
| Mtr.38650.1.S1_at | ANS | NA | TC103244/FEA = mRNA/DEF = weakly similar to UP \| Q5UL08 (Q5UL08) Anthocyanidin synthase, partial (25%) |
| Mtr.10779.1.S1_at | CHI | 16.8.2 | TC107882/FEA = mRNA/DEF = similar to UP \| CFI_VITVI (P51117) Chalcone--flavonone isomerase (Chalcone isomerase), partial (90%) |
| Mtr.37080.1.S1_at | CHI | 16.8.2 | TC112171/FEA = mRNA/DEF = similar to UP \| Q9FUH5 (Q9FUH5) Chalcone isomerase 1 (Fragment), partial (20%) |
| Mtr.37412.1.S1_at | CHI | 16.8.2 | TC100603/FEA = mRNA/DEF = similar to UP \| Q9FLC7 (Q9FLC7) Similarity to chalcone-flavonone isomerase, partial (69%) |
| Mtr.37412.1.S1_s_at | CHI | 16.8.2 | TC100603/FEA = mRNA/DEF = similar to UP \| Q9FLC7 (Q9FLC7) Similarity to chalcone-flavonone isomerase, partial (69%) |
| Mtr.37413.1.S1_s_at | CHI | 16.8.2 | TC100605/FEA = mRNA/DEF = similar to UP \| Q9FLC7 (Q9FLC7) Similarity to chalcone-flavonone isomerase, partial (52%) |
| Mtr.40331.1.S1_at | CHI | 16.8.2 | TC107065/FEA = mRNA/DEF = weakly similar to UP \| CFI_PHAVU (P14298) Chalcone--flavonone isomerase (Chalcone isomerase), partial (94%) |
| Mtr.4347.1.S1_s_at | CHI | 16.8.2 | AJ497605/FEA = mRNA/DEF = similar to UP \| CFI_IPOPU (O22604) Chalcone--flavonone isomerase (Chalcone isomerase), partial (24%) |
| Mtr.6282.1.S1_at | CHI | 16.8.2 | BQ137326/FEA = mRNA/DEF = similar to UP \| Q9FLC7 (Q9FLC7) Similarity to chalcone-flavonone isomerase, partial (9%) |
| Mtr.8531.1.S1_at | CHI | 16.8.2 | TC100522/FEA = mRNA/DEF = homologue to UP \| CFI1_MEDSA (P28012) Chalcone--flavonone isomerase 1 (Chalcone isomerase 1), complete |
| Mtr.8555.1.S1_at | CHI | 16.8.2 | TC100604/FEA = mRNA/DEF = similar to UP \| Q9FLC7 (Q9FLC7) Similarity to chalcone-flavonone isomerase, partial (58%) |
| Mtr.10368.1.S1_at | CHS | 16.8.2 | TC106536/FEA = mRNA/DEF = homologue to UP \| CHS8_MEDSA (P30076) Chalcone synthase 8 (Naringenin-chalcone synthase 8), complete |
| Mtr.10369.1.S1_at | CHS | 16.8.2 | TC106538/FEA = mRNA/DEF = similar to UP \| Q5WM49 (Q5WM49) Chalcone synthase, complete |

TABLE 4-continued

List of probeset IDs for enzymes of FIG. 10b.

| Probesets | Name | BINS | Target Description |
|---|---|---|---|
| Mtr.14428.1.S1_at | CHS | 16.8.2.1 | IMGAG | 1115.m00011/FEA = mRNA/DEF = Naringenin-chalcone synthase; Type III polyketide synthase AC146683.9.101 54170 52902 mth2-179n10 Jan. 13, 2005 |
| Mtr.14428.1.S1_x_at | CHS | 16.8.2.1 | IMGAG | 1115.m00011/FEA = mRNA/DEF = Naringenin-chalcone synthase; Type III polyketide synthase AC146683.9.101 54170 52902 mth2-179n10 Jan. 13, 2005 |
| Mtr.17612.1.S1_x_at | CHS | 16.8.2.1 | IMGAG | 918.m00012/FEA = mRNA/DEF = Naringenin-chalcone synthase; Type III polyketide synthase AC137823.43.121 61682 60352 mth2-14c17 Jan. 13, 2005 |
| Mtr.17616.1.S1_x_at | CHS | 16.8.2.1 | IMGAG | 918.m00018/FEA = mRNA/DEF = Naringenin-chalcone synthase; Type III polyketide synthase AC137823.43.181 72290 73620 mth2-14c17 Jan. 13, 2005 |
| Mtr.17621.1.S1_x_at | CHS | 16.8.2.1 | IMGAG | 918.m00021/FEA = mRNA/DEF = Naringenin-chalcone synthase; Type III polyketide synthase AC137823.43.211 79927 81521 mth2-14c17 Jan. 13, 2005 |
| Mtr.20185.1.S1_at | CHS | 16.8.2.1 | IMGAG | 1104.m00013/FEA = mRNA/DEF = Naringenin-chalcone synthase; Type III polyketide synthase AC146575.3.131 82667 81204 mth2-145m4 Jan. 13, 2005 |
| Mtr.20185.1.S1_x_at | CHS | 16.8.2.1 | IMGAG | 1104.m00013/FEA = mRNA/DEF = Naringenin-chalcone synthase; Type III polyketide synthase AC146575.3.131 82667 81204 mth2-145m4 Jan. 13, 2005 |
| Mtr.20187.1.S1_at | CHS | 16.8.2.1 | IMGAG | 1104.m00017/FEA = mRNA/DEF = Naringenin-chalcone synthase; Type III polyketide synthase AC146575.3.171 96668 95373 mth2-145m4 Jan. 13, 2005 |
| Mtr.20187.1.S1_x_at | CHS | 16.8.2.1 | IMGAG | 1104.m00017/FEA = mRNA/DEF = Naringenin-chalcone synthase; Type III polyketide synthase AC146575.3.171 96668 95373 mth2-145m4 Jan. 13, 2005 |
| Mtr.20464.1.S1_x_at | CHS | 16.8.2.1 | IMGAG | 1111.m00013/FEA = mRNA/DEF = Naringenin-chalcone synthase; Type III polyketide synthase AC146650.13.121 79531 80861 mth2-14j5 Jan. 13, 2005 |
| Mtr.20567.1.S1_at | CHS | 16.2.99 | IMGAG | 1115.m00010/FEA = mRNA/DEF = Type III polyketide synthase; Naringenin-chalcone synthase AC146683.9.91 50180 48876 mth2-179n10 Jan. 13, 2005 |
| Mtr.28714.1.S1_at | CHS | 16.8.2 | BI311259/FEA = mRNA/DEF = homologue to PRF | 1609233A | 226868 | 1609233A chalcone synthase 3. {Sinapis alba;}, partial (12%) |
| Mtr.31570.1.S1_at | CHS | 16.8.2 | AL370397/FEA = mRNA/DEF = weakly similar to UP | CFI_PUELO (Q43056) Chalcone--flavonone isomerase (Chalcone isomerase), partial (64%) |
| Mtr.32188.1.S1_x_at | CHS | 16.8.2 | AW684295/FEA = mRNA/DEF = homologue to UP | CHS9_MEDSA (P30077) Chalcone synthase 9 (Naringenin-chalcone synthase 9), partial (24%) |
| Mtr.33961.1.S1_at | CHS | 16.8.2 | BQ135500/FEA = mRNA/DEF = similar to UP | Q5XVS6 (Q5XVS6) Chalcone synthase, partial (11%) |
| Mtr.33982.1.S1_at | CHS | 16.8.2 | BQ135569/FEA = mRNA/DEF = weakly similar to UP | CHS3_PEA (O23883) Chalcone synthase 3 (Naregenin-chalcone synthase 3), partial (10%) |
| Mtr.36618.1.S1_at | CHS | 16.8.2 | BQ143805/FEA = mRNA/DEF = similar to UP | Q9SLY0 (Q9SLY0) Chalcone synthase, partial (3%) |
| Mtr.40122.1.S1_s_at | CHS | 16.8.2 | TC106554/FEA = mRNA/DEF = homologue to UP | CHS4_MEDSA (P30075) Chalcone synthase 4 (Naringenin-chalcone synthase 4) (CHS12-1), partial (82%) |
| Mtr.40123.1.S1_at | CHS | 16.8.2 | TC106555/FEA = mRNA/DEF = homologue to UP | CHS4_MEDSA (P30075) Chalcone synthase 4 (Naringenin-chalcone synthase 4) (CHS12-1), partial (34%) |
| Mtr.43713.1.S1_at | CHS | 16.8.2 | TC95902/FEA = mRNA/DEF = similar to UP | O80407 (O80407) Chalcone synthase, partial (95%) |
| Mtr.44617.1.S1_at | CHS | 16.8.2 | TC97724/FEA = mRNA/DEF = weakly similar to GB | AAB35812.1 | 1246019 | S80554 chalcone synthase {Arabidopsis;}, partial (31%) |
| Mtr.44844.1.S1_at | CHS | 16.8.2 | TC98216/FEA = mRNA/DEF = homologue to UP | Q41399 (Q41399) Chalcone reductase, partial (69%) |
| Mtr.45667.1.S1_x_at | CHS | 16.2.99 | IMGAG | 918.m00023/FEA = mRNA/DEF = Type III polyketide synthase; Naringenin-chalcone synthase AC137823.43.231 84744 86235 mth2-14c17 Jan. 13, 2005 |
| Mtr.49572.1.S1_s_at | CHS | 16.8.2.1 | IMGAG | 1104.m00016/FEA = mRNA/DEF = Naringenin-chalcone synthase; Type III polyketide synthase AC146575.3.161 92557 91179 mth2-145m4 Jan. 13, 2005 |
| Mtr.49572.1.S1_x_at | CHS | 16.8.2.1 | IMGAG | 1104.m00016/FEA = mRNA/DEF = Naringenin-chalcone synthase; Type III polyketide synthase AC146575.3.161 92557 91179 mth2-145m4 Jan. 13, 2005 |
| Mtr.49576.1.S1_at | CHS | 16.2.99 | IMGAG | 1104.m00010/FEA = mRNA/DEF = Ankyrin; Naringenin-chalcone synthase AC146575.3.101 65210 64569 mth2-145m4 Jan. 13, 2005 |
| Mtr.52044.1.S1_s_at | CHS | 16.8.2.1 | IMGAG | 848.m00025/FEA = mRNA/DEF = Naringenin-chalcone synthase AC134242.17.251 108327 109841 mth2-10p20 Jan. 13, 2005 |
| Mtr.6212.1.S1_at | CHS | 16.8.2 | BQ135426/FEA = mRNA/DEF = weakly similar to UP | CHS3_PEA (O23883) Chalcone synthase 3 (Naregenin-chalcone synthase 3), partial (9%) |
| Mtr.6221.1.S1_at | CHS | 16.8.2 | BQ135487/FEA = mRNA/DEF = similar to GB | BAA01513.1 | 391783 | PEACHS2 chalcone synthase {Pisum sativum;}, partial (39%) |
| Mtr.38073.1.S1_at | DFR | 16.8.4 | TC102034/FEA = mRNA/DEF = UP | Q6TQT1 (Q6TQT1) Dihydroflavanol-4-reductase 1, complete |
| Mtr.38756.1.S1_at | DFR | 16.8.4 | TC103465/FEA = mRNA/DEF = UP | Q6TQT0 (Q6TQT0) Dihydroflavonal-4-reductase 2, complete |
| Mtr.4272.1.S1_at | DFR | 16.8.4 | AA660236/FEA = mRNA/DEF = similar to UP | Q9FS36 (Q9FS36) Dihydroflavonol 4-reductase, partial (9%) |
| Mtr.4272.1.S1_s_at | DFR | 16.8.4 | AA660236/FEA = mRNA/DEF = similar to UP | Q9FS36 (Q9FS36) Dihydroflavonol 4-reductase, partial (9%) |
| Mtr.13960.1.S1_at | F3H | 16.8.4 | TC99759/FEA = mRNA/DEF = similar to UP | Q84JJ4 (Q84JJ4) Flavonoid 3'-hydroxylase (Fragment), partial (63%) |
| Mtr.32642.1.S1_at | F3H | 16.8.4 | BE248260/FEA = mRNA/DEF = similar to UP | C755_EUSGR (Q96418) Flavonoid 3',5'-hydroxylase (F3'5'H) (Cytochrome P450 75A5), partial (18%) |
| Mtr.35691.1.S1_at | F3H | 16.8.4 | TC111173/FEA = mRNA/DEF = weakly similar to UP | Q9STI0 (Q9STI0) Flavonoid 3',5'-hydroxylase-like protein (At4g12310), partial (9%) |
| Mtr.36333.1.S1_at | F3H | 16.8.4 | BE248436/FEA = mRNA/DEF = similar to UP | Q84JJ4 (Q84JJ4) Flavonoid 3'-hydroxylase (Fragment), partial (21%) |
| Mtr.38450.1.S1_at | F3H | 16.8.3 | TC102835/FEA = mRNA/DEF = weakly similar to GB | AAT44124.1 | 48431269 | AY550120 F3H-like protein {Saussurea medusa;}, partial (27%) |

TABLE 4-continued

List of probeset IDs for enzymes of FIG. 10b.

| Probesets | Name | BINS | Target Description |
|---|---|---|---|
| Mtr.38814.1.S1_at | F3H | 16.8.4 | TC103590/FEA = mRNA/DEF = weakly similar to UP | Q9STH8 (Q9STH8) Flavonoid 3',5'-hydroxylase like protein (Flavonoid 3,5-hydroxylase like protein), partial (33%) |
| Mtr.42668.1.S1_at | F3H | 16.8.3 | TC112116/FEA = mRNA/DEF = weakly similar to GB | AAT44124.1 | 48431269 | AY550120 F3H-like protein {Saussurea medusa;}, partial (32%) |
| Mtr.45258.1.S1_at | F3H | 16.8.4 | TC99191/FEA = mRNA/DEF = similar to UP | Q76LL4 (Q76LL4) Flavonoid 3',5'-hydroxylase, partial (53%) |
| Mtr.6409.1.S1_at | F3H | 16.8.4 | BQ141925/FEA = mRNA/DEF = similar to UP | Q6J210 (Q6J210) Flavonoid 3' 5'-hydroxylase, partial (2%) |
| Mtr.7094.1.S1_at | F3H | 16.8.4 | CX540205/FEA = mRNA/DEF = homologue to UP | Q9FPN3 (Q9FPN3) Flavonoid 3',5'-hydroxylase, partial (13%) |
| Mtr.9446.1.S1_at | F3H | 16.8.3 | TC103378/FEA = mRNA/DEF = weakly similar to UP | Q9FLV0 (Q9FLV0) Flavanone 3-hydroxylase-like protein, partial (28%) |
| Mtr.9867.1.S1_at | F3H | 16.8.3 | TC104677/FEA = mRNA/DEF = weakly similar to GB | AAT44124.1 | 48431269 | AY550120 F3H-like protein {Saussurea medusa;}, partial (24%) |
| Mtr.24709.1.S1_at | FLS | NA | 1761.m00046/FEA = mRNA/DEF = AC152349.3 81074 80260 mth2-52p10 weakly similar to TAIR | gene: 1005714550-GOpep .2 68410.m02179 flavonol synthase family contains similarity to flavonol synthase |
| Mtr.38256.1.S1_s_at | FLS | 16.8.4 | TC102386/FEA = mRNA/DEF = weakly similar to UP | Q84UT8 (Q84UT8) Flavonol synthase, partial (25%) |
| Mtr.44957.1.S1_at | FLS | 16.8.4 | TC98484/FEA = mRNA/DEF = weakly similar to UP | FLS_EUSGR (Q9M547) Flavonol synthase (FLS), partial (50%) |
| Mtr.10553.1.S1_at | GT | 26.2 | TC107173/FEA = mRNA/DEF = weakly similar to UP | Q6VAB3 (Q6VAB3) UDP-glycosyltransferase 85A8, partial (27%) |
| Mtr.21996.1.S1_x_at | GT | NA | 1578.m00031/FEA = mRNA/DEF = AC124966.27 4823 6271 mth2-8i15 weakly similar to UP | Q8S996 (Q8S996) Glucosyltransferase-13 (Fragment) |
| Mtr.24410.1.S1_at | GT | NA | 1739.m00044/FEA = mRNA/DEF = AC151424.10 31908 29993 mth2-101c17 similar to UP | Q8S996 (Q8S996) Glucosyltransferase-13 (Fragment) |
| Mtr.31819.1.S1_at | GT | NA | AL381855/FEA = mRNA/DEF = weakly similar to UP | Q9T081 (Q9T081) UDP rhamnose--anthocyanidin-3-glucoside rhamnosyltransferase-like protein (At4g27570), partial (17%) |
| Mtr.44505.1.S1_at | GT | 26.2 | TC97488/FEA = mRNA/DEF = similar to UP | Q8S9A0 (Q8S9A0) Glucosyltransferase-9, partial (70%) |
| Mtr.45072.1.S1_at | GT | NA | TC98718/FEA = mRNA/DEF = weakly similar to UP | LGT_CITUN (Q9MB73) Limonoid UDP-glucosyltransferase (Limonoid glucosyltransferase) (Limonoid GTase) (LGTase), partial (32%) |
| Mtr.20055.1.S1_at | LAR | NA | IMGAG | 1099.m00001/FEA = mRNA/DEF = leucoanthocyanidin reductase (ec 1.17.1.3) (leucocyanidin reductase) AC146570.4.1 1634 5066 mth2-103j7 Jan. 13, 2005 |
| Mtr.10404.1.S1_at | PAL | 16.2.1.1 | TC106670/FEA = mRNA/DEF = homologue to UP | PALY_MEDSA (P27990) Phenylalanine ammonia-lyase, partial (19%) |
| Mtr.38612.1.S1_at | PAL | 16.2.1.1 | TC103174/FEA = mRNA/DEF = similar to PRF | 1807329B | 228615 | 1807329B Phe ammonia lyase. {Phaseolus vulgaris;}, partial (28%) |
| Mtr.40166.1.S1_s_at | PAL | 16.2.1.1 | TC106668/FEA = mRNA/DEF = homologue to UP | PALY_MEDSA (P27990) Phenylalanine ammonia-lyase, partial (28%) |
| Mtr.40167.1.S1_s_at | PAL | 16.2.1.1 | TC106669/FEA = mRNA/DEF = homologue to UP | PALY_MEDSA (P27990) Phenylalanine ammonia-lyase, complete |
| Mtr.40168.1.S1_at | PAL | 16.2.1.1 | TC106671/FEA = mRNA/DEF = similar to UP | Q9M567 (Q9M567) Phenylalanine ammonia-lyase 2, partial (15%) |
| Mtr.50478.1.S1_at | PAL | 16.2.1.1 | IMGAG | 968.m00002/FEA = mRNA/DEF = Phenylalanine/histidine ammonia-lyase; L-Aspartase-like; Phenylalanine ammonia-lyase AC140028.21.21 6624 2477 mth2-7e24 Jan. 13, 2005 |
| Mtr.51909.1.S1_at | PAL | 16.2.1.1 | IMGAG | 843.m00022/FEA = mRNA/DEF = Phenylalanine/histidine ammonia-lyase; L-Aspartase-like; Phenylalanine ammonia-lyase AC133709.10.211 119802 113450 mth2-7b3 Jan. 13, 2005 |
| Mtr.9254.1.S1_at | PAL | 16.2.1.1 | TC102823/FEA = mRNA/DEF = similar to PRF | 1807329B | 228615 | 1807329B Phe ammonia lyase. {Phaseolus vulgaris;}, partial (47%) |
| Mtr.20924.1.S1_at | TT2 | 27.3.32.1 | IMGAG | 1132.m00008/FEA = mRNA/DEF = Myb, DNA-binding; Homeodomain-like AC146760.13.71 50869 52550 mth2-174d3 Jan. 13, 2005 |
| Mtr.22479.1.S1_at | TT8 | 16.8.1.1001 | 1606.m00039/FEA = mRNA/DEF = AC135317.10 9174 16609 mth2-10p4 weakly similar to UP | Q9FEA1 (Q9FEA1) Anthocyanin 1 |
| Mtr.253.1.S1_at | TT8 | 27.3.10 | 1802.m00045/FEA = mRNA/DEF = CR932963.1 77295 81200 mth2-115p22 weakly similar to UP | O81348 (O81348) Symbiotic ammonium transporter |
| Mtr.31614.1.S1_at | TTG1 | NA | AL372205/FEA = mRNA/DEF = similar to UP | Q8L5J3 (Q8L5J3) WD-repeat protein GhTTG1, partial (8%) |
| Mtr.39774.1.S1_at | TTG1 | NA | TC105711/FEA = mRNA/DEF = homologue to UP | Q9M610 (Q9M610) Ttg1-like protein, partial (46%) |

To assess the impact of the par mutation on the flavonoid pathway as a whole, we performed metabolite profiling using ultra-performance liquid chromatography coupled to electro-spray ionization quadrupole time of flight mass spectometry (HPLC-ESI-QTOF-MS). Out of 74 secondary metabolites identified in mature seeds, 22 were altered significantly in amount in par mutants compared to wild-type controls (See Table 5).

TABLE 5

UPLC Mass spectrometry results.

| Field Name | Field Name | AVR WT | SD WT | AVR Mut | SD Mut | T-Test | |
|---|---|---|---|---|---|---|---|
| 163.0385 | p-Coumaric acid (Aut_DH) | 0.414033 | 0.032933 | 0.353565 | 0.066928 | | coumaric product |
| 161.0239 | umbelliferone (Aut_DH)) | 98.90151 | 1.901535 | 100.5152 | 1.20757 | | coumaric product |
| | | 99.31554 | 1.890719 | 100.8688 | 1.228534 | 0.039054093 | |
| | | 1 | 0.019037 | 1.015639 | 0.01237 | | |
| 451.1235 | EpicatechinGlucoside (Aut_DH) | 2.170932 | 0.229599 | 1.211214 | 0.123314 | | Epicatechin |
| 289.0726 | Epicatechin (Aut_DH)) | 0.649441 | 0.081218 | 0.314479 | 0.042761 | | Epicatechin |
| | | 2.820373 | 0.303687 | 1.525693 | 0.143791 | 3.67702E−08 | |
| | | 1 | 0.107676 | 0.540954 | 0.050983 | | |
| 609.1505 | luteolin-3-7-di-O-glu (Aut_DH) | 0.338314 | 0.144366 | 0.815536 | 0.229098 | | Flavonol gycosides |
| 609.1476 | luteolin-3,7-O-glu (Aut_DH)") | 0.344542 | 0.146416 | 0.819365 | 0.227313 | | Flavonol gycosides |
| 607.1331 | Rutin(AUT_DH) | 1.065182 | 0.464067 | 2.687139 | 0.875834 | | Flavonol gycosides |
| 607.1297 | Kaempferol Glucuronide Rhamnose (Put_YDS) | 1.057552 | 0.469356 | 2.705964 | 0.892704 | | Flavonol gycosides |
| 593.1505 | kempferol-3-O-rutinoside (Aut_DH) | 0.649113 | 0.124604 | 0.505343 | 0.025441 | | Flavonol gycosides |
| 271.0606 | Narigenin-7-O-glucoside-aglycone (Aut_DH) | 0.27681 | 0.053653 | 0.195376 | 0.048142 | | Flavonol gycosides |
| 431.0962 | apigenin-7-O-glu (Aut_DH) or | 6.948113 | 1.442785 | 5.433148 | 0.635942 | | Flavonol gycosides |
| | | 10.67962 | 1.827922 | 13.16187 | 2.811249 | 0.033908428 | |
| | | 1 | 0.17116 | 1.232428 | 0.263235 | | |
| 455.3538 | Soyasapogenol E | 2.853693 | 0.714358 | 1.503997 | 0.090121 | | Saponins |
| 663.3756 | Hex-Medicagenic Acid (Put_DH) | 1.567111 | 0.342674 | 1.046466 | 0.083917 | | Saponins |
| 793.4335 | HexA-Hex-Soyasapogenol E (Put_MB) | 1.118791 | 0.070432 | 0.937857 | 0.110712 | | Saponins |
| 793.4389 | HexA-Hex-Soy E (Put_DH) | 1.109246 | 0.061841 | 0.935179 | 0.113136 | | Saponins |
| 925.4822 | Hex-Hex-Rha-SoyE (Put_DH) | 0.632367 | 0.40404 | 1.040187 | 0.163535 | | Saponins |
| 501.3228 | Mediagenic Acid (Put_DH) | 0.522835 | 0.579536 | 0.075502 | 0.029033 | | Saponins |
| 957.506 | Hex-Hex-Hex-Hederagenin (Put_MB) | 0.388559 | 0.153379 | 0.93891 | 0.713847 | | Saponins |
| 957.5068 | Hex-Hex-Hex-Hederagenin (Put_DH) | 0.369966 | 0.173381 | 0.888785 | 0.749956 | | Saponins |
| | | 8.562569 | 1.230207 | 7.366883 | 1.493789 | 0.058799186 | |
| | | 1 | 0.143673 | 0.860359 | 0.174456 | | |

These metabolites belonged mainly to four classes of compounds: coumaric acid-related compounds (2 metabolites), triterpene saponins (8), epicatechins (2) and flavonol glycosides (7). Although the amount of individual saponins changed in the par mutants, the total amount of saponins was not significantly different between mutants and their wild-type siblings. The same was true of the coumaric acid-related compounds. In contrast, total epicatechin content was substantially lower by 45.9% and flavonol glycoside content higher by 23.2% in par mutants than in wild-type controls (FIG. 10c). The reduced amount of epicatechin in the par mutants mirrored the reduced level soluble PAs in these mutants (FIG. 10c).

Taken together, the results of genetic, transcriptomic and metabolomic analyses indicate that MtPAR plays a rather specific role as a positive regulator of PA biosynthesis in M. truncatula.

Example 4

MtPAR Acts Upstream of TTG1

Previously, a WD40 repeat protein, orthologous to Arabidopsis TTG1, was identified in M. truncatula and called MtWD40-1 (Pang et al., 2009). M. truncatula wd40-1 mutants displayed a drastic decrease of soluble and insoluble PA (Pang et al., 2009). However, over-expression of MtWD40-1 in M. truncatula hairy roots resulted in an increase of anthocyanin content without affecting PA content. Published transcriptome data of wd40-1 mutants (Pang et al.; 2009) were compared to those of par mutants. Of the 38 genes that were down-regulated in 20 DAP seeds of par mutants compared to wild-type controls, 16 were also down-regulated in wd40-1 mutant seeds collected at 16 DAP. Moreover, almost all (14/16) are related to flavonoid biosynthesis according to Genebins ontology (Goffard & Weiler, 2007); list and annotations are shown in Table 6 (list of probesets down-regulated in par and ttg1 mutant lines).

TABLE 6

Common probesets down-regulated in par and ttg1 mutant lines.

| Probesets | Target Description |
|---|---|
| Mtr.20567.1.S1_at | IMGAG | 1115.m00010/FEA = mRNA/DEF = Type III polyketide synthase; Naringenin-chalcone synthase AC146683.9.91 50180 48876 mth2-179n10 Jan. 13, 2005 |
| Mtr.36333.1.S1_at | BE248436/FEA = mRNA/DEF = similar to UP | Q84JJ4 (Q84JJ4) Flavonoid 3'-hydroxylase (Fragment), partial (21%) |
| Mtr.6517.1.S1_at | BQ147749/FEA = mRNA/DEF = similar to UP | Q84J65 (Q84J65) Gray pubescence flavonoid 3'-hydroxylase, partial (49%) |
| Mtr.49572.1.S1_s_at | IMGAG | 1104.m00016/FEA = mRNA/DEF = Naringenin-chalcone synthase; Type III polyketide synthase AC146575.3.161 92557 91179 mth2-145m4 Jan. 13, 2005 |
| Mtr.20187.1.S1_x_at | IMGAG | 1104.m00017/FEA = mRNA/DEF = Naringenin-chalcone synthase; Type III polyketide synthase AC146575.3.171 96668 95373 mth2-145m4 Jan. 13, 2005 |
| Mtr.20187.1.S1_at | IMGAG | 1104.m00017/FEA = mRNA/DEF = Naringenin-chalcone synthase; Type III polyketide synthase AC146575.3.171 96668 95373 mth2-145m4 Jan. 13, 2005 |
| Mtr.14017.1.S1_at | TC99980/FEA = mRNA/DEF = weakly similar to UP | LDOX_ARATH (Q96323) Leucoanthocyanidin dioxygenase (LDOX) (Leucocyanidin oxygenase) (Leucoanthocyanidin hydroxylase) (Anthocyanidin synthase) (ANS), partial (19%) |
| Mtr.39897.1.S1_at | TC105988/FEA = mRNA/DEF = similar to UP | P93697 (P93697) CPRD12 protein, partial (61%) |

TABLE 6-continued

Common probesets down-regulated in par and ttg1 mutant lines.

| Probesets | Target Description |
|---|---|
| Mtr.49572.1.S1_x_at | IMGAG \| 1104.m00016/FEA = mRNA/DEF = Naringenin-chalcone synthase; Type III polyketide synthase AC146575.3.161 92557 91179 mth2-145m4 Jan. 13, 2005 |
| Mtr.21996.1.S1_x_at | 1578.m00031/FEA = mRNA/DEF = AC124966.27 4823 6271 mth2-8i15 weakly similar to UP \| Q8S996 (Q8S996) Glucosyltransferase-13 (Fragment) |
| Mtr.44985.1.S1_at | TC98546/FEA = mRNA/DEF = UP \| Q84XT1 (Q84XT1) Anthocyanidin reductase, complete |
| Mtr.28714.1.S1_at | BI311259/FEA = mRNA/DEF = homologue to PRF \| 1609233A \| 226868 \| 1609233A chalcone synthase 3. {*Sinapis alba*;}, partial (12%) |
| Mtr.16432.1.S1_at | IMGAG \| 824.m00011/FEA = mRNA/DEF = Myb, DNA-binding; Homeodomain-like AC129092.13.101 59248 60901 mth2-17n16 Jan. 13, 2005 |
| Mtr.41031.1.S1_at | TC108579/FEA = mRNA/DEF = homologue to PIR \| PQ0772 \| PQ0772 4-coumarate-CoA ligase (clone GM4CL1B) - soybean (fragment) {*Glycine max*;}, partial (62%) |
| Mtr.10917.1.S1_at | TC108343/FEA = mRNA/DEF = similar to UP \| C773_SOYBN (O48928) Cytochrome P450 77A3, partial (95%) |
| Mtr.50478.1.S1_at | IMGAG \| 968. m00002/FEA = mRNA/DEF = Phenylalanine/histidine ammonia-lyase; L-Aspartase-like; Phenylalanine ammonia-lyase AC140028.21.21 6624 2477 mth2-7e24 Jan. 13, 2005 |

To test whether MtPAR and MtWD40-1 act via a common regulatory pathway to induce target genes, WD40-1 gene expression was measured in par mutants, by qRT-PCR. Significantly, WD40-1 transcript levels were between 15 and 50 times lower in par mutant seeds than in wild-type sibling seed controls at 20 DAP (FIG. 6c). In contrast, PAR transcript levels were unaffected by mutations in the WD40-1 gene in 16 DAP seeds (Pang et al., 2009). Conversely, MtPAR overexpression induced MtWD40-1 expression in *Medicago* hairy roots (FIG. 6b). A list of probesets up-regulated in hairy root transformants over-expressing PAR and 112 is given in Table 7.

experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are

TABLE 7

Probesets up-regulated in hairy root transformants over-expressing PAR and TT2.

| Probesets | Target Description |
|---|---|
| Mtr.47022.1.S1_s_at | 1705.m00036/FEA = mRNA/DEF = AC148359.19 17939 18394 mth2-22k11 weakly similar to TAIR \| gene: 2181071-GOpep .1 68412.m00083 expressed protein wound-inducible protein wun1 protein - *Solanum* |
| Mtr.20567.1.S1_at | IMGAG \| 1115.m00010/FEA = mRNA/DEF = Type III polyketide synthase; Naringenin-chalcone synthase AC146683.9.91 50180 48876 mth2-179n10 Jan. 13, 2005 |
| Mtr.33715.1.S1_at | BI265542/FEA = mRNA/DEF = |
| Mtr.25016.1.S1_at | 1785.m00050/FEA = mRNA/DEF = AC155890.1 50797 51458 mth2-49p3 |
| Mtr.14017.1.S1_at | TC99980/FEA = mRNA/DEF = weakly similar to UP \| LDOX_ARATH (Q96323) Leucoanthocyanidin dioxygenase (LDOX) (Leucocyanidin oxygenase) (Leucoanthocyanidin hydroxylase) (Anthocyanidin synthase) (ANS), partial (19%) |
| Mtr.1157.1.S1_s_at | 1544.m00032/FEA = mRNA/DEF = AC149039.2 10370 11266 mth2-4g23 weakly similar to UP \| Q6WAY3 (Q6WAY3) Gag/pol polyprotein |
| Mtr.148.1.S1_s_at | 1785.m00048/FEA = mRNA /DEF = AC155890.1 47822 48796 mth2-49p3 |
| Mtr.11000.1.S1_at | TC108561/FEA = mRNA/DEF = |
| Mtr.6517.1.S1_at | BQ147749/FEA = mRNA/DEF = similar to UP \| Q84J65 (Q84J65) Gray pubescence flavonoid 3'-hydroxylase, partial (49%) |
| Mtr.17982.1.S1_s_at | IMGAG \| 932.m00012/FEA = mRNA/DEF = hypothetical protein AC138017.15.111 51242 50808 mth2-6i3 Jan. 13, 2005 |
| Mtr.51818.1.S1_at | IMGAG \| 896.m00006/FEA = mRNA/DEF = predicted protein AC136840.24.51 30231 32005 mth2-33n3 Jan. 13, 2005 |
| Mtr.15436.1.S1_at | IMGAG \| 786.m00019/FEA = mRNA/DEF = 2OG-Fe(ll) oxygenase; Immunoglobulin/major histocompatibility complex AC125478.13.191 98375 97104 mth2-31i19 Jan. 13, 2005 |
| Mtr.25672.1.S1_a_at | 1446.m00048/FEA = mRNA/DEF = AC146752.23 87430 86695 mth2-62d4 |
| Mtr.32965.1.S1_at | BF635325/FEA = mRNA/DEF = similar to UP \| Q9ZSP7 (Q9ZSP7) Cytochrome b5 DIF-F, partial (36%) |
| Mtr.9894.1.S1_at | TC104797/FEA = mRNA/DEF = weakly similar to UP \| Q9LQ75 (Q9LQ75) T1N6.22 protein, partial (48%) |
| Mtr.28737.1.S1_at | BI312112/FEA = mRNA/DEF = similar to UP \| Q8LIS8 (Q8LIS8) Homeodomain protein GhHOX1, partial (27%) |
| Mtr.20511.1.S1_s_at | IMGAG \| 1220.m00020/FEA = mRNA/DEF = hypothetical protein AC148758.19.191 94204 93893 mth2-50l17 Jan. 13, 2005 |
| Mtr.27451.1.S1_at | BE124481/FEA = mRNA/DEF = |
| Mtr.16363.1.S1_s_at | IMGAG \| 868.m00002/FEA = mRNA/DEF = LQGC hypothetical protein AC135396.30.21 8440 9117 mth2-33o18 Jan. 13, 2005 |
| Mtr.44300.1.S1_at | TC97086/FEA = mRNA/DEF = similar to UP \| Q9ZR88 (Q9ZR88) Bifunctional nuclease (Fragment), partial (93%) |

All of the compositions and methods disclosed and claimed herein can be made and executed without undue deemed to be within the spirit, scope and concept of the invention as defined by the appended claims.

REFERENCES

The references listed below are incorporated herein by reference to the extent that they supplement, explain, provide a background for, or teach methodology, techniques, and/or compositions employed herein.

U.S. Pat. No. 5,508,184
U.S. Pat. No. 5,545,818
U.S. Pat. No. 5,610,042
U.S. Pat. No. 7,709,701
U.S. Patent Appl. Publ. 2005/0203033
PCT App. WO 94/09699
PCT App. WO 95/06128
Aasland et al. *Trends Biochem. Sci.* 21:87-88, 1996.
Abrahams et al. *Pl. Physiol.* 130:561-576, 2002.
Aerts R J, Barry T N, McNabb W C (1999) Polyphenols and agriculture: beneficial effects of proanthocyanidins in forages. Agriculture Ecosystems & Environment 75: 1-12.
Ahmad et al., *Arch. Biochem. Biophys.* 376:338-346, 2000.
Albert et al., *Plant J.*, February; 11(2):289-99, 1997.
Aziz et al., *Planta*, 221:28-38, 2005.
Bagchi et al., *Mutation Res.*, 523-524:87-97, 2003.
Bagchi et al., *Toxicology*, 148:187-97, 2000.
Barry and McNabb, *Brit. J. Nutr.* 81:263-72, 1999.
Bateman et al., *NAR* 30:276-280, 2002
Baudry et al., *Plant J.*, 39: 366-380, 2004.
Bavage et al., *Plant Mol. Biol.* 35:443-458, 1997.
Benedito et al., *Plant J.* 55:504-513, 2008.
Bevan et al., *Nucleic Acids Research*, 11(2):369-385, 1983.
Boisson-Dernier et al., *Mol. Plant-Microbe Interactions*, 14:695-700, 2001.
Borevitz et al., *Plant Cell*, 12:2383-2393, 2000.
Broeckling et al., *Anal. Chem.* 78:4334-4341, 2006.
Canon et al., *Theor. App. Genet.*, 87:1006-1015, 1994.
Chandler et al., *Plant Cell*, 1:1175-1183, 1989.
Cheng et al., *Methods Mol. Biol.* 678:179-190, 2011.
Chu et al., *Scientia Sinica*, 18:659-668, 1975.
Church and Gilbert, *Proc. Natl. Acad. Sci.* USA, 81:1991-1995, 11984.
Clough and Bent, *Plant J.*, 16:735-743, 1998.
Conkling et al., *Plant Physiol.*, 93:1203-1211, 1990.
Dalzell and Kerven, *J. Sci. Food Agric.*, 78:405-416, 1998.
Debeaujon et al., *Plant Cell*, 13:853-872, 2001.
Debeaujon et al., *Plant Cell*, 15:2514-2531, 2003.
Debeaujon et al., Seed Coat Development and Dormancy. pp. 25-43 in: *Seed Development, Dormancy and Germination*; eds. K. Bradford & H. Nonogaki; Blackwell 2007.
Dellaporta et al., In: *Chromosome Structure and Function: Impact of New Concepts*, 18th Stadler Genetics Symposium, 11:263-282, 1988.
Devic et al., *Plant J.*, 19:387-398, 1999.
Dixon et al., *New Phytologist* 165:9-28, 2005.
Dozmorov and Centola, *Bioinformatics* 19:204-211, 2003.
Ebert et al., *Proc. Natl. Acad. Sci. USA*, 84:5745-5749, 1987.
Foo et al., *Phytochemistry*, 54:173-81, 2000.
Gallie et al., *Plant Cell*, 1:301-311, 1989.
Gamborg et al., *Exp. Cell Res.*, 50, 151-158, 1968.
Gelvin et al., In: *Plant Molecular Biology Manual*, 1990.
Giner-Chavez et al., *J. Sci. Food Agric.*, 74:359-368, 1997.
Goffard and Weiller, *BMC Bioinformatics* 8:87, 2007
Gonzalez et al., *Plant J.* 53:814-827, 2008.
Hamilton et al., *Proc. Natl. Acad. Sci. USA*, 93(18):9975-9979, 1996.
He et al., *BMC Bioinformatics.* 10:441, 2009.
Hinchee et al., *Bio/technol.*, 6:915-922, 1988.
Howles, et al., *Plant Physiol.*, 112:1617-1624, 1996.
Hudspeth and Grula, *Plant Mol. Biol.*, 12:579-589, 1989.
Ikuta et al., *Bio/technol.*, 8:241-242, 1990.
Irizarry et al., *NAR* 31:E15, 2003.
Jefferson et al. *EMBO J.* 6:3901-3907, 1987.
Johnson et al., *Plant Cell* 14:1359-1375, 2002.
Kitamura et al., *Plant J.*, 37:104-114, 2004.
Koupai-Abyazani et al., *J. Agric. Food Chem.*, 41:565-569, 1993.
Kristensen and Aastrup, *Carlsberg Res. Commun.*, 51:509-513, 1986.
Kristiansen, *Carlsberg Res. Commun.*, 49:503-524, 1984.
Lawton et al., *Plant Mol. Biol.* 9:315-324, 1987.
Leek et al., *Bioinformatics* 22:507-508, 2005.
Lepiniec et al., *Annu Rev Plant Biol.* 57:405-30, 2006.
Li and Wong, *PNAS* 98:31-36, 2001.
Lin et al., *J. Nat. Prod.*, 65:505-8, 2002.
McKhann and Hirsch, *Plant Mol Biol.*, 24(5):767-77, 1994
Morris and Robbins, In: *Biotechnology and the Improvement of Forage Legumes*, McKersie and Brown (Eds.), CAB International, Wallingford, Conn., 147-173, 1997.
Murashige and Skoog, *Physiol. Plant.*, 15:473-497, 1962.
Nesi et al., *Plant Cell*, 12:1863-1878, 2000.
Nesi et al., *Plant Cell*, 14:2463-2479, 2002.
Nesi, et al., *Plant Cell*, 13:2099-2114, 2001.
Niwa et al., *Plant J.*, 18:445-463, 1999.
Noreen et al., *Planta Med* 64:520-524, 1998.
Odell et al., *Nature*, 313:810-812, 1985.
Ogawa et al., *Sci. Rep.*, 13:42-48, 1973.
Pang et al., *Pl. Physiol.* 145:601-615, 2007.
Pang et al. *PNAS* 105:14210-14215, 2008.
Pang et al., *Pl. Physiol.* 151:1114-1129, 2009.
Pataki et al., *Am. J. Clin. Nutr.*, 75:894-899, 2002.
Quandt et al., *Mol. Plant-Microbe Interactions*, 6:699-706, 1993.
Ramakers et al., *Neurosci. Lett.* 339:62-66, 2003.
Restrepo M A, Freed D D, Carrington J C (1990) Nuclear transport of plant potyviral proteins. Plant Cell 2: 987-998.
Roe, B. A., J. S. Crabtree, and A. S. Khan. 1996. DNA Isolation and Sequencing (Essential Techniques Series). New York: John Wiley & Sons. 176 pp.
Sagasser et al., *Genes Dev.*, 16:138-149, 2002.
Saito et al., *Plant J.*, 17:181-189, 1999.
Sambrook et al., In:: *Molecular Cloning-A Laboratory Manual* (second edition), Cold Spring Harbour Laboratory Press, 1989.
Serafini et al., *Nature* 424:1013, 2003.
Skadhauge et al., *Am. J. Bot.*, 84:494-502, 1997.
Stafford, H. A., Pathway to proanthocyanidins (condensed tannins), flavan-3-ols, and unsubstituted flavans. In: Flavonoid metabolism edited by Stafford, H. A., CRC Press. Inc., pp 63-99, 1990.
Stangeland B, Salehian Z (2002) An improved clearing method for GUS assay in *Arabidopsis* endosperm and seeds. Plant Molecular Biology Reporter 20: 107-114.
Stracke et al., *Curr. Opinion Pl. Biol.* 4:445-456, 2001.
Sullivan et al., *Mol. Gen. Genet.*, 215:431-440, 1989.
Sumner et al., *Pl. Sys. Biol.* 97:195-212, 2007.
Tadege et al. *Plant J.* 54:335-347, 2008.
Tanner et al., *Austr. J. Agric. Res.*, 46:1101-1109, 1995.
Vasil et al., *Plant Physiol.*, 91:1575-1579, 1989.
Verdier et al., *Plant Mol. Biol.* 67:567-580, 2008.
Walker et al. *Plant Cell*, 11:1337-1350, 1999.
Walker et al., *Proc. Natl. Acad. Sci. USA*, 84:6624-6628, 1987.
Wang et al., *Molecular and Cellular Biology*, 12(8):3399-3406, 1992.
Xie et al., *Plant J.* 45:895-907, 2004.
Yang and Russell, *Proc. Natl. Acad. Sci. USA*, 87:4144-4148, 1990.
Zhao and Dixon, *Trends Plant Sci.* 15:72-80, 2010.

The invention claimed is:

1. A DNA molecule comprising a DNA sequence selected from the group consisting of:
   (a) a sequence encoding the polypeptide sequence of SEQ ID NO:1;
   (b) a sequence comprising the sequence of SEQ ID NO:2;
   (c) a sequence that hybridizes to SEQ ID NO:2 under conditions of 1×SSC, and 65° C., wherein the sequence encodes a polypeptide that regulates flavonoid synthesis;
   (d) a sequence encoding a polypeptide with at least 85% amino acid identity to SEQ ID NO:1, wherein the polypeptide regulates flavonoid synthesis;
   (e) a sequence with at least 85% identity to SEQ ID NO:2, wherein the sequence encodes a polypeptide that regulates flavonoid synthesis; and
   (f) a complement of a sequence of any of (a)-(e), wherein the DNA sequence is operably linked to a heterologous promoter.

2. The DNA molecule of claim 1, wherein the sequence has at least 90 percent sequence identity to the amino acid sequence of SEQ ID NO:1 or to the DNA sequence of SEQ ID NO:2.

3. The DNA molecule of claim 1, wherein the sequence has at least 95 percent sequence identity to the amino acid sequence of SEQ ID NO:1 or to the DNA sequence of SEQ ID NO:2.

4. A recombinant vector comprising the DNA molecule of claim 1.

5. The recombinant vector of claim 4, further comprising at least one additional sequence chosen from the group consisting of: a selectable marker, a leader sequence, a sequence encoding a polypeptide that allows for anthocyanin or proanthocyanidin biosynthesis, and a terminator.

6. The recombinant vector of claim 5, wherein the polypeptide that allows for anthocyanin or proanthocyanidin biosynthesis is selected from the group consisting of: phenylalanine ammonia-lyase (PAL), cinnamate 4-hydroxylase (C4H), 4-coumarate:CoA ligase (4CL), chalcone synthase (CHS), chalcone isomerase (CHI), flavanone 3-hydroxylase (F3H), dihydroflavonol reductase (DFR), anthocyanidin synthase (ANS), leucoanthocyanidin reductase (LAR), anthocyanidin reductase (ANR), and a proanthocyanidin or anthocyanidin glucosyltransferase (GT).

7. The recombinant vector of claim 4, wherein the promoter is a plant developmentally-regulated, organelle-specific, inducible, tissue-specific, constitutive, or cell-specific promoter.

8. A transgenic plant cell or plant part comprising the DNA molecule of claim 1.

9. A transgenic plant comprising the DNA molecule of claim 1.

10. The transgenic plant of claim 9, wherein the plant is a *Medicago* plant.

11. The transgenic plant of claim 10, wherein the plant expresses the selected DNA and exhibits altered proanthocyanidin biosynthesis in selected tissues relative to those tissues in a second plant that differs from the transgenic plant only in that the selected DNA is absent.

12. The transgenic plant of claim 9, further defined as transformed with a selected DNA comprising a sequence encoding a proanthocyanidin regulatory polypeptide selected from the group consisting of SEQ ID NO:1, and a sequence with at least 90% sequence similarity to SEQ ID NO:1, having anthocyanin or proanthocyanidin biosynthesis regulatory activity.

13. The transgenic plant of claim 9, further defined as transformed with a selected DNA sequence complementary to at least 19 contiguous nucleotides of SEQ ID NO:2.

14. The transgenic plant of claim 13, further defined as transformed with a DNA sequence comprising at least 21 contiguous nucleotides complementary to SEQ ID NO: 2.

15. The transgenic plant of claim 13, wherein the selected DNA sequence comprises the complement of SEQ ID NO:2, or a fragment thereof.

16. The transgenic plant of claim 9, further defined as transformed with a DNA sequence encoding the polypeptide of SEQ ID NO:1.

17. The transgenic plant of claim 9, further defined as a forage crop.

18. The transgenic plant of claim 17, wherein the plant is a forage legume.

19. The transgenic plant of claim 18, wherein the forage legume is alfalfa (*Medicago sativa*).

20. The transgenic plant of claim 9, further defined as a fertile R0 transgenic plant.

21. The transgenic plant of claim 9, further defined as a progeny plant of any generation of a fertile R0 transgenic plant, wherein the transgenic plant comprises the selected DNA.

22. The transgenic plant of claim 9, wherein the plant is further defined as comprising a transgenic sequence that down-regulates proanthocyanidin biosynthesis.

23. A seed of the transgenic plant of claim 9, comprising the DNA molecule of claim 1.

24. A method of producing a plant with increased proanthocyanidin biosynthesis, comprising expressing in the plant the DNA molecule of claim 1.

25. The method of claim 24, wherein the plant further comprises a recombinant vector of claim 4.

26. The method of claim 24, wherein the DNA molecule is introduced into the plant by plant breeding.

27. The method of claim 24, wherein the DNA molecule is introduced into the plant by genetic transformation of the plant.

28. The method of claim 24, wherein the promoter is a constitutive or tissue specific promoter.

29. The method of claim 24, wherein the plant is a forage crop plant.

30. The method of claim 29, wherein the plant is a forage legume.

31. The method of claim 30, wherein the plant is alfalfa.

32. A method of making food or feed for human or animal consumption comprising:
   (a) obtaining the plant of claim 9;
   (b) growing the plant under plant growth conditions to produce plant tissue from the plant; and
   (c) preparing food or feed for human or animal consumption from the plant tissue.

33. The method of claim 32, wherein preparing food comprises harvesting the plant tissue.

34. The method of claim 32, wherein the food is hay, silage, starch, protein, meal, flour or grain.

* * * * *

SEQUENCE LISTING

<160> NUMBER OF SEQ ID NOS: 24

<210> SEQ ID NO 1
<211> LENGTH: 254
<212> TYPE: PRT
<213> ORGANISM: Medicago truncatula

<400> SEQUENCE: 1

Met Val Arg Ser Pro Lys Glu Val Asn Lys Gly Ala Trp Ser Arg Glu
1               5                   10                  15

Glu Asp Asp Ile Leu Ser Lys Tyr Val Val Ile His Gly Glu Gly Lys
            20                  25                  30

Trp Gln Lys Val Ala Gln Asn Ala Gly Leu Lys Arg Cys Gly Lys Ser
        35                  40                  45

Cys Arg Gln Arg Trp Leu Asn Tyr Leu Lys Pro Gly Ile Lys Arg Gly
    50                  55                  60

His Ile Ser Thr Asp Glu Glu Asp Met Ile Ile Arg Leu His Arg Leu
65                  70                  75                  80

Leu Gly Asn Arg Trp Ser Leu Ile Ala Lys Arg Leu Pro Gly Arg Thr
                85                  90                  95

Asp Asn Glu Ile Lys Asn Tyr Trp Asn Thr Asn Leu Ser Lys Lys Leu
            100                 105                 110

Gln Lys Gln Pro Thr Ser Ser Ser Leu Pro Ser Pro Ser Ser Val
        115                 120                 125

Ser Leu Arg His Asn His Gly Lys Cys Gly His Val Ala Pro Glu Ala
    130                 135                 140

Pro Lys Pro Arg Arg Leu Lys Ala Val His Gln Tyr Lys Ile Leu Glu
145                 150                 155                 160

Lys Asn Ser Gly Ser Glu Tyr Asp Gln Gly Ser Asp Glu Thr Ser Ile
                165                 170                 175

Ala Asp Phe Phe Ile Asp Phe Asp His Gln Asp Gln Leu Met Val Gly
            180                 185                 190

Asp Asp Glu Ser Asn Ser Lys Ile Pro Gln Met Glu Asp His Lys Val
        195                 200                 205

Ser Ser Thr Asn Ser Thr His Ser Ser Ser Pro Ser Asp His Cys
    210                 215                 220

His Leu Leu Ala Glu Lys Phe Asp Pro Gln Glu Ile Leu Leu Asp Val
225                 230                 235                 240

Glu Leu Lys Lys Met Ala Ser Phe Leu Gly Leu Glu Asn Asp
                245                 250

<210> SEQ ID NO 2
<211> LENGTH: 765
<212> TYPE: DNA
<213> ORGANISM: Medicago truncatula

<400> SEQUENCE: 2
atggttagaa gtcctaagga ggttaataaa ggtgcttggt ctcgtgaaga agatgatatc      60
ctctccaaat atgttgtcat tcatggagaa ggaaaatggc aaaaggttgc ccaaaatgca     120
ggtttaaagc ggtgtggaaa aagttgtaga caaagatggt tgaattatct caaaccaggt     180
ataaagagag gccatatctc taccgacgaa gaagacatga tcataagact tcatcgtctt     240
cttggtaaca gatggtcttt gatagctaag agactaccag gacgaacaga caatgaaatc     300
aagaactact ggaatactaa tctgtcaaag aagttacaaa aacagccaac atcatcatca     360
tcattgccat caccatcttc tgtttcactt cgacacaatc atggcaaatg tggacatgta     420

```
gcaccagaag ctccaaagcc taggagactg aaggctgttc atcaatacaa aattttggaa      480
aagaatagtg gaagtgagta tgatcaagga agtgatgaaa cttctattgc tgattttttc      540
attgactttg atcatcaaga tcaattgatg gttggtgatg atgagtctaa ttcaaagatt      600
ccacaaatgg aagatcacaa ggtgagttca acaaatagta ctcatagttc atcatcacct      660
tctgatcatt gtcatctttt agcagagaaa tttgaccctc aagagatcct tttggatgtg      720
gagcttaaga gatggcttc ctttcttgga cttgaaaatg attga                       765

<210> SEQ ID NO 3
<211> LENGTH: 2594
<212> TYPE: DNA
<213> ORGANISM: Medicago truncatula

<400> SEQUENCE: 3
tgttcacctc tcttagatta ctcaaaaaaa aaaaaaacta atttaaaatt ataaaagtat       60
ttttaaacaa attttcaaat gaagaacaa tattttaact taaaacttac ataatactat      120
ttttagaaac agacttacat aataagttat aaaaataaaa aataaaaact tataaactac      180
tgttgaagga acttaaagga gggtgaataa acattttagc tattgaacgt caatcaagtt      240
actctccatc aatcaattga attgattctt atgaatttgc atcgcgaaag ttgtaaataa      300
atttatagaa acatatccct tgagcttagt tcagttggta gggatattgc atattatatg      360
caggagccgg ggttcgaacc ccggacactc cacttctcca caattaaaac tcggctttga      420
cctgacaaat gatgaaaatt gaagaggtta agcatatgtt taatttcata gaataattta      480
tcattttgta atttggtgac aaattatcta acctctacaa ttgatatgat tcattaaact      540
taaagatttc ctaatgtggg ttttatgtct cacaacacaa aagtcatgaa acccatcaaa      600
aaggtttcca attccaatgc atgtgggaca aaatatgaag gaagccaaac tccatcagtt      660
gttggttggt cccctccct tgtgatgtcg acgtacgagg agtacgatac gcaatatttt       720
cacacccaat ttgctttaaa gtctttcatg ttttcttgtc ttgttttca ttttttataat      780 ttttttcttg tattaactaa tgaccctcat aacattgttg tccctttcct ctttgctata      840
tggatccatg gaaagtacgt acatttttct aagctactaa atatgtgtag taataaatta      900
aagccactat agtcattatt gttttttatga gtggcagtgg agtgttttt gtgtgaagaa      960 gaagaagaag aagaagaagc aaagtaacta agtaagtaac atggttagaa gtcctaagga     1020
ggttaataaa ggtgcttggt ctcgtgaaga agatgatatc ctctccaaat atgttgtcat     1080
tcatggagaa ggaaaatggc aaaaggttgc ccaaaatgca ggtgctaaat taattactga     1140
ttttctctaa tgcacaacta tattatagtt gccattcaat gtgttttcat gagacttgta     1200 tccttttcctg tctctccaaa caaatcttga tagttggatt aatttgaatg ccgagaggt     1260 ttgtctagag agactgtaga ggatacaaga ttgttccatg catgtcctta gattttgaat     1320
ccgatttggc cgtggcagaa gatcatgttg tctattataa ttttttcttaa atagttttcg     1380 attggtctct ttggtttata tggagtaggt ttaaagcggt gtggaaaaag ttgtagacaa     1440
agatggttga attatctcaa accaggtata aagagaggcc atatctctac cgacgaagaa     1500
gacatgatca taagacttca tcgtcttctt ggtaacaggt gattttattt tttattttg      1560 ttttaaatta gcctatgcta ctcgacacaa gtctgataat ggtgatctag agttcggtcg     1620
agagctaagt gagatttgac caatataatt ctagtcagga atcgaatcat cacaattcat     1680
tctccttcat tattataaat gactaaaatt tatgatattt gttctatata gatggtcttt     1740
```

```
gatagctaag agactaccag gacgaacaga caatgaaatc aagaactact ggaatactaa    1800
tctgtcaaag aagttacaaa aacagccaac atcatcatca tcattgccat caccatcttc    1860
tgtttcactt cgacacaatc atggcaaatg tggacatgta gcaccagaag ctccaaagcc    1920
taggagacta aaggctgttc atcaatacaa aattttggaa aagaatagtg gaagtgagta    1980
tgatcaagga agtgatgaaa cttctattgc tgatttttttc attgactttg atcatcaaga    2040
tcaattgatg gttggtgatg atgagtctaa ttcaaagatt ccacaaatgg aagatcacaa    2100
ggtgagttca acaaatagta ctcatagttc atcatcacct tctgatcatt gtcatctttt    2160
agcagagaaa tttgaccctc aagagatcct tttggatgtg gagcttaaga agatggcttc    2220 cttctcttgga cttgaaaatg attgaagtga tttattccaa tgaggggacc aagagaaaaa    2280
ggtcaagtga attgggaatc atatagcctt tgctatatgc catttttata tgtatttcct    2340
aactaaacat gtaactagat gaacaagttc ttggcttctt ctttatgtca cttgatcacc    2400
aatcctttat accaaaaaag tttgaatata gtgacggaaa attagagacc gaaaaacatg    2460 aaaattcgtct ttgattttgt ctctaattga tacaaaatta tagacgctaa agtagaagat    2520
tattctcttt ttctatcact aatttccgtc gataatttca cttttttctag tagatattat    2580 gccacaataa ttta                                                      2594

<210> SEQ ID NO 4
<211> LENGTH: 1029
<212> TYPE: DNA
<213> ORGANISM: Medicago truncatula

<400> SEQUENCE: 4
atggataatt caacacaaga atcccatctc cgatccgata caactccgt aacatacgat       60 tccccatacc cactctacgc catgtccatc tctcccaaca caattcccc acaacaacgt      120 atcgccgtcg gaagcttcat cgaagaatac acaaaccgca tcgatattct caatttcaac     180 cccgatacccc tctcactcaa acctcaacct tcactctcct tcgatcaccc ttacccacca     240
accaaactca tgttccatcc cgccacacat tcttctctcc agaaaacctc ctccgacctc     300
cttgctacct ccggtgacta tctccgtctc tgggaagttc gtgaaaattc cgttgaagct     360 cttttctcttt tcaacaatag caaaaccagt gagttttgtg ctcctttaac atcatttgat     420
tggaatgaaa ttgagcccaa acgaattgga acttcaagta ttgacactac ttgtactatc     480
tgggacattg aaagaggcgt tgttgaaacg cagttaattg cgcatgataa agaggtttat     540
gatattgctt gggggaaatc aagggttttt gcttcggttt ctgctgatgg gtctgttagg     600 attttgatt aagggataa agagcattca acaattatct atgaaagtcc gcaacctgat     660 accccctttgc ttcgtttagc ttggaacaag aaggatttga ggtatatggc cacgattttg     720
atggatagta ataaagttgt gattttggat attagatcac caactacacc ggtcgcggaa     780
ttggagagac atcgcgctgg tgttaatgct attgcttggg ctccaagaag ttcaaagcat     840
atttgttccg gtggggatga tgcacaggct cttatttggg agttgccggc tgtagctggt     900
ccgaatggga ttgatccgat gactacgtat tctgctggtt gtgaaattaa tcagcttcag     960
tggtctgctg ctcagcctga ttggattgct attgcttttg ctaataaaat gcagcttttg    1020
agggtttga                                                             1029

<210> SEQ ID NO 5
<211> LENGTH: 20
<212> TYPE: DNA
<213> ORGANISM: Artificial Sequence
```

```
<220> FEATURE:
<223> OTHER INFORMATION: primer

<400> SEQUENCE: 5
tgagtggcag tggagtgttt                                              20

<210> SEQ ID NO 6
<211> LENGTH: 22
<212> TYPE: DNA
<213> ORGANISM: Artificial sequence
<220> FEATURE:
<223> OTHER INFORMATION: Synthetic primer

<400> SEQUENCE: 6
taaaggtgct tggtctcgtg aa                                           22

<210> SEQ ID NO 7
<211> LENGTH: 20
<212> TYPE: DNA
<213> ORGANISM: Artificial sequence
<220> FEATURE:
<223> OTHER INFORMATION: Synthetic primer

<400> SEQUENCE: 7
ggtctctaat tttccgtcac                                              20

<210> SEQ ID NO 8
<211> LENGTH: 22
<212> TYPE: DNA
<213> ORGANISM: Artificial Sequence
<220> FEATURE:
<223> OTHER INFORMATION: Synthetic primer

<400> SEQUENCE: 8
ggtcccctca ttggaataaa tc                                           22

<210> SEQ ID NO 9
<211> LENGTH: 24
<212> TYPE: DNA
<213> ORGANISM: Artificial Sequence
<220> FEATURE:
<223> OTHER INFORMATION: Synthetic primer

<400> SEQUENCE: 9
atggttagaa gtcctaagga ggtt                                         24

<210> SEQ ID NO 10
<211> LENGTH: 25
<212> TYPE: DNA
<213> ORGANISM: Artificial Sequence
<220> FEATURE:
<223> OTHER INFORMATION: Synthetic primer

<400> SEQUENCE: 10
tcaatcattt tcaagtccaa gaaag                                        25

<210> SEQ ID NO 11
<211> LENGTH: 25
<212> TYPE: DNA
<213> ORGANISM: Artificial Sequence
<220> FEATURE:
<223> OTHER INFORMATION: Synthetic primer

<400> SEQUENCE: 11
gttgaagtag acattggtgc taacg                                        25
```

<210> SEQ ID NO 12
<211> LENGTH: 23
<212> TYPE: DNA
<213> ORGANISM: Artificial sequence
<220> FEATURE:
<223> OTHER INFORMATION: Synthetic primer

<400> SEQUENCE: 12
agctgagtca tcaacaccct cat                                           23

<210> SEQ ID NO 13
<211> LENGTH: 19
<212> TYPE: DNA
<213> ORGANISM: Artificial Sequence
<220> FEATURE:
<223> OTHER INFORMATION: Synthetic primer

<400> SEQUENCE: 13
gtgttttgct tccgccgtt                                                19

<210> SEQ ID NO 14
<211> LENGTH: 22
<212> TYPE: DNA
<213> ORGANISM: Artificial Sequence
<220> FEATURE:
<223> OTHER INFORMATION: Synthetic primer

<400> SEQUENCE: 14
ccaaatcttg ctccctcatc tg                                            22

<210> SEQ ID NO 15
<211> LENGTH: 20
<212> TYPE: DNA
<213> ORGANISM: Artificial Sequence
<220> FEATURE:
<223> OTHER INFORMATION: Synthetic primer

<400> SEQUENCE: 15
accaactaca ccggtcgcgg                                               20

<210> SEQ ID NO 16
<211> LENGTH: 20
<212> TYPE: DNA
<213> ORGANISM: Artificial Sequence
<220> FEATURE:
<223> OTHER INFORMATION: Synthetic primer

<400> SEQUENCE: 16
gctacagccg gcaactccca                                               20

<210> SEQ ID NO 17
<211> LENGTH: 20
<212> TYPE: DNA
<213> ORGANISM: Artificial Sequence
<220> FEATURE:
<223> OTHER INFORMATION: Synthetic primer

<400> SEQUENCE: 17
cgtccatccg tcaaacgcgg                                               20

<210> SEQ ID NO 18
<211> LENGTH: 20
<212> TYPE: DNA
<213> ORGANISM: Artificial Sequence
<220> FEATURE:
<223> OTHER INFORMATION: Synthetic primer

```
<400> SEQUENCE: 18
acggtggagg cggaggatga                                              20

<210> SEQ ID NO 19
<211> LENGTH: 22
<212> TYPE: DNA
<213> ORGANISM: Artificial Sequence
<220> FEATURE:
<223> OTHER INFORMATION: Synthetic primer

<400> SEQUENCE: 19
gcaaagccac ccacttgggg tt                                           22

<210> SEQ ID NO 20
<211> LENGTH: 22
<212> TYPE: DNA
<213> ORGANISM: Artificial Sequence
<220> FEATURE:
<223> OTHER INFORMATION: Synthetic primer

<400> SEQUENCE: 20
tcagcaaatt tccacgcagc ct                                           22

<210> SEQ ID NO 21
<211> LENGTH: 23
<212> TYPE: DNA
<213> ORGANISM: Artificial Sequence
<220> FEATURE:
<223> OTHER INFORMATION: Synthetic primer

<400> SEQUENCE: 21
acgacgatgc atttgctgca cac                                          23

<210> SEQ ID NO 22
<211> LENGTH: 20
<212> TYPE: DNA
<213> ORGANISM: Artificial Sequence
<220> FEATURE:
<223> OTHER INFORMATION: Synthetic primer

<400> SEQUENCE: 22
ggcggcgatt cccacagagc                                              20

<210> SEQ ID NO 23
<211> LENGTH: 26
<212> TYPE: DNA
<213> ORGANISM: Artificial Sequence
<220> FEATURE:
<223> OTHER INFORMATION: Synthetic primer

<400> SEQUENCE: 23
agccaacatc atcatcatca ttgcca                                       26

<210> SEQ ID NO 24
<211> LENGTH: 22
<212> TYPE: DNA
<213> ORGANISM: Artificial Sequence
<220> FEATURE:
<223> OTHER INFORMATION: Synthetic primer

<400> SEQUENCE: 24
aggctttgga gcttctggtg ct                                           22
```